US008093265B2

(12) United States Patent
Kelly et al.

(10) Patent No.: US 8,093,265 B2
(45) Date of Patent: *Jan. 10, 2012

(54) BICYCLOHETEROARYL COMPOUNDS AS P2X7 MODULATORS AND USES THEREOF

(75) Inventors: Michael G. Kelly, Thousand Oaks, CA (US); John Kincaid, San Francisco, CA (US); Yunfeng Fang, Foster City, CA (US); Yeyu Cao, Foster City, CA (US); Carl Kaub, San Mateo, CA (US); Sumithra Gowlugari, San Mateo, CA (US); Zhan Wang, Palo Alto, CA (US)

(73) Assignee: Renovis, Inc., South San Francisco, CA (US)

( * ) Notice: Subject to any disclaimer, the term of this patent is extended or adjusted under 35 U.S.C. 154(b) by 694 days.

This patent is subject to a terminal disclaimer.

(21) Appl. No.: 12/075,111

(22) Filed: Mar. 7, 2008

(65) Prior Publication Data
US 2008/0287415 A1 Nov. 20, 2008

Related U.S. Application Data

(60) Provisional application No. 60/906,049, filed on Mar. 9, 2007, provisional application No. 60/918,261, filed on Mar. 15, 2007, provisional application No. 60/918,123, filed on Mar. 15, 2007, provisional application No. 60/918,260, filed on Mar. 15, 2007, provisional application No. 60/918,086, filed on Mar. 15, 2007, provisional application No. 61/008,370, filed on Dec. 20, 2007, provisional application No. 61/008,385, filed on Dec. 20, 2007, provisional application No. 61/008,386, filed on Dec. 20, 2007, provisional application No. 61/010,672, filed on Jan. 10, 2008.

(51) Int. Cl.
C07D 217/22 (2006.01)
A61K 31/4704 (2006.01)

(52) U.S. Cl. ........................................ 514/309; 546/143

(58) Field of Classification Search ............................. None
See application file for complete search history.

(56) References Cited

U.S. PATENT DOCUMENTS

| | | | |
|---|---|---|---|
| 3,900,477 A | 8/1975 | Philipp et al. |
| 3,950,343 A | 4/1976 | Philipp et al. |
| 4,897,391 A | 1/1990 | Friary |
| 5,491,148 A | 2/1996 | Berger et al. |
| 5,631,280 A | 5/1997 | Ciccarone et al. |
| 5,723,411 A | 3/1998 | Stevenson |
| 5,968,946 A | 10/1999 | Maryanoff et al. |
| 6,034,107 A | 3/2000 | Hirai et al. |
| 6,083,987 A | 7/2000 | Nishino et al. |
| 6,262,068 B1 | 7/2001 | Atwal et al. |
| 6,492,378 B1 | 12/2002 | Harling et al. |
| 6,603,013 B2 | 8/2003 | Sun et al. |
| 6,812,226 B2 | 11/2004 | Baxter et al. |

| | | | |
|---|---|---|---|
| 2001/0034346 A1 | 10/2001 | Milton et al. |
| 2004/0180894 A1 | 9/2004 | Dombroski |
| 2005/0009900 A1 | 1/2005 | Dombroski et al. |
| 2005/0049253 A1 | 3/2005 | Tegley |
| 2005/0165028 A1 | 7/2005 | Norman et al. |
| 2005/0215572 A1 | 9/2005 | Kelly et al. |
| 2005/0222200 A1 | 10/2005 | Kelly |
| 2005/0267018 A1 | 12/2005 | Blatt et al. |
| 2006/0135557 A1 | 6/2006 | Nan et al. |
| 2006/0194801 A1 | 8/2006 | Kelly et al. |
| 2008/0214524 A1 | 9/2008 | Lee et al. |

FOREIGN PATENT DOCUMENTS

| | | |
|---|---|---|
| CA | 2068255 | 5/1991 |
| DE | 2343984 | 3/1975 |
| DE | 4333761 | 4/1995 |
| DE | 19650975 | 12/1996 |
| DE | 19653647 | 12/1996 |
| DE | 19653645 | 6/1998 |
| DE | 10238865 | 3/2004 |
| EP | 00093488 | 11/1983 |

(Continued)

OTHER PUBLICATIONS

West, Anthony R., Solid State Chemistry and its Applications, Wiley, New York, 1988, pp. 358 & 365.*
Wu et al., Toxicology, 236, pp. 1-6, 2007.*
U.S. Appl. No. 05/588,736, filed Jun. 19, 1975, United States Dept. of the Air Force.
Archiv der Pharmazie (1990), 323(3), 145-55.
Zhurnal Obshchei Khimii (1989), 59(6), 1385-90.
Teoreticheskaya I Eksperimental'naya Khimiya (1988), 24(4), 474-9.
J. Gen. Chem. USSR (Engl. Transl.) (1989), 59(6), 1229-1233.
Yagupol'skii et al., 1961, Zhurnal Obshchei Khimii, 31:3586-3593 (non-patent entry 2).
Surprenant et al, Science, vol. 272, (1996), 735-738.

Primary Examiner — Zinna Northington Davis
(74) Attorney, Agent, or Firm — Klauber & Jackson LLC

(57) ABSTRACT

Compounds are disclosed that have a formula represented by the following:

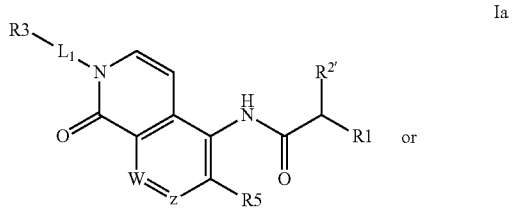

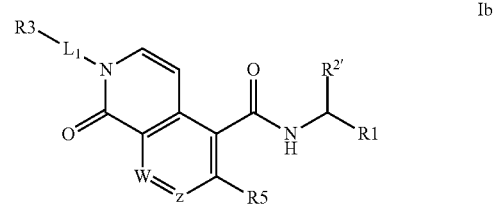

The compounds may be prepared as pharmaceutical compositions, and may be used for the prevention and treatment of a variety of conditions in mammals including humans, including by way of non-limiting example, pain, inflammation, traumatic injury, and others.

28 Claims, No Drawings

FOREIGN PATENT DOCUMENTS

| | | |
|---|---|---|
| EP | 0095262 A1 | 11/1983 |
| EP | 101641 A2 | 2/1984 |
| EP | 0326106 A2 | 8/1989 |
| EP | 0454121 A2 | 10/1991 |
| EP | 0471358 A1 | 2/1992 |
| EP | 0482939 A1 | 4/1992 |
| EP | 0502575 A1 | 9/1992 |
| EP | 540334 A1 | 5/1993 |
| EP | 799826 A1 | 10/1997 |
| EP | 877019 A1 | 5/1998 |
| EP | 1200086 A | 5/2002 |
| EP | 1208085 A2 | 5/2002 |
| FR | M2450 | 5/1964 |
| GB | 2044254 A | 10/1980 |
| JP | 62258462 | 11/1987 |
| JP | 06295078 | 10/1994 |
| JP | 11171774 | 6/1999 |
| JP | 2001 172258 | 6/2001 |
| JP | 2002 338837 | 11/2002 |
| JP | 2004 203813 | 7/2004 |
| JP | 2005 232175 | 9/2005 |
| SU | 749832 A1 | 7/1980 |
| SU | 1776659 A1 | 11/1992 |
| WO | WO 91/08205 | 6/1991 |
| WO | WO 92/14730 | 9/1992 |
| WO | WO 92/18115 | 10/1992 |
| WO | WO 93/09136 | 5/1993 |
| WO | WO 94/02482 | 2/1994 |
| WO | WO 94/13667 | 6/1994 |
| WO | WO 94/29273 | 12/1994 |
| WO | WO 95/11680 | 5/1995 |
| WO | WO 95/18097 | 7/1995 |
| WO | WO 95/21168 | 8/1995 |
| WO | WO 95/30647 | 11/1995 |
| WO | WO 95/34556 | 12/1995 |
| WO | WO 96/30014 | 10/1996 |
| WO | WO 97/01275 | 1/1997 |
| WO | WO 97/47601 | 12/1997 |
| WO | WO 98/04247 | 2/1998 |
| WO | WO 98/07421 | 2/1998 |
| WO | WO 99/02497 | 1/1999 |
| WO | WO 99/21836 | 5/1999 |
| WO | WO 99/38850 | 8/1999 |
| WO | WO 99/59975 | 11/1999 |
| WO | WO 01/04086 | 1/2001 |
| WO | WO 01/10380 | 2/2001 |
| WO | WO 01/10381 | 2/2001 |
| WO | WO 01/12187 | 2/2001 |
| WO | WO 01/21615 | 3/2001 |
| WO | WO 01/51456 | 7/2001 |
| WO | WO 01/72712 | 10/2001 |
| WO | WO 02/06240 | 1/2002 |
| WO | WO 02/062816 | 8/2002 |
| WO | WO 02/094790 | 11/2002 |
| WO | WO 03/011285 | 2/2003 |
| WO | WO 03/070247 | 8/2003 |
| WO | WO 03/080578 | 10/2003 |
| WO | WO 03/080582 | 10/2003 |
| WO | WO 03/082827 | 10/2003 |
| WO | WO 03/093249 | 11/2003 |
| WO | WO 2004/009555 | 1/2004 |
| WO | WO 2004/062601 | 7/2004 |
| WO | WO 2004/065351 | 8/2004 |
| WO | WO 2004/069792 | 8/2004 |
| WO | WO 2004/096807 | 11/2004 |
| WO | WO 2004/111010 | 12/2004 |
| WO | WO 2004/113345 | 12/2004 |
| WO | WO 2005/035526 | 4/2005 |
| WO | WO 2005/046683 | 5/2005 |
| WO | WO 2005/051300 | 6/2005 |
| WO | WO 2005/065702 | 7/2005 |
| WO | WO 2005/108389 | 11/2005 |
| WO | WO 2006/030032 | 3/2006 |
| WO | WO 2006/043490 | 4/2006 |
| WO | WO 2006/048727 | 5/2006 |
| WO | WO 2006/050998 | 5/2006 |
| WO | WO 2006/057270 | 6/2006 |
| WO | WO 2006/066950 | 6/2006 |
| WO | WO 2006/069132 | 6/2006 |
| WO | WO 2006/076442 | 7/2006 |
| WO | WO 2006/093832 | 9/2006 |
| WO | WO 2006/102588 | 9/2006 |
| WO | WO 2006/108714 | 10/2006 |
| WO | WO 2006/119542 | 11/2006 |
| WO | WO 2007/012421 | 2/2007 |
| WO | WO 2007/012422 | 2/2007 |
| WO | WO 2007/030693 | 3/2007 |
| WO | WO 2007/109154 | 9/2007 |
| WO | WO 2007/109160 | 9/2007 |
| WO | WO 2007/109192 | 9/2007 |

* cited by examiner

BICYCLOHETEROARYL COMPOUNDS AS P2X7 MODULATORS AND USES THEREOF

RELATED APPLICATIONS

The present application claims the priority of co-pending provisional applications U.S. Ser. No. 60/906,049, filed on Mar. 9, 2007; U.S. Ser. No. 60/918,261, filed on Mar. 15, 2007; U.S. Ser. No. 60/918,123, filed on Mar. 15, 2007; U.S. Ser. No. 60/918,260, filed on Mar. 15, 2007; U.S. Ser. No. 60/918,086, filed on Mar. 15, 2007; U.S. Ser. No. 61/008,370, filed on Dec. 20, 2007; U.S. Ser. No. 61/008,385, filed on Dec. 20, 2007; U.S. Ser. No. 61/008,386, filed on Dec. 20, 2007; and U.S. Ser. No. 61/010,672, filed on Jan. 10, 2008. The disclosures of all of the aforementioned applications are incorporated by reference herein in their entireties. Applicants claim the benefits of these applications under 35 U.S.C. §119(e).

FIELD OF THE INVENTION

This invention relates to novel compounds including compounds of the class bicycloheteroaryl that are capable of modulating $P2X_7$ receptor activity, and to pharmaceutical compositions containing such compounds. This invention also relates to methods for preventing and/or treating conditions that are causally related to aberrant $P2X_7$ activity, such as inflammation-related conditions in mammals, comprising (but not limited to) rheumatoid arthritis, osteoarthritis, Parkinson's disease, uveitis, asthma, cardiovascular conditions including myocardial infarction, the treatment and prophylaxis of pain syndromes (acute and chronic or neuropathic), traumatic brain injury, acute spinal cord injury, neurodegenerative disorders, inflammatory bowel disease and autoimmune disorders, using the compounds and pharmaceutical compositions of the invention.

BACKGROUND OF THE INVENTION

Cell surface receptors for ATP can be divided into metabotropic (P2Y/P2U) and ionotropic (P2X) classes. The metabotropic class belongs to the superfamily of G protein-coupled receptors, with seven transmembrane segments. The ionotropic class members ($P2X_1$-$P2X_6$) are ligand-gated ion channels, currently thought to be multisubunit proteins with two transmembrane domains per subunit (Buell et al, Europ. J. Neurosci. 8:2221 (1996)). P2Z receptors have been distinguished from other P2 receptors in three primary ways (Buisman et al, Proc. Natl. Acad. Sci. USA 85:7988 (1988); Cockcroft et al, Nature 279:541 (1979); Steinberg et al, J. Biol. Chem. 262:3118 (1987)). First, activation of P2Z receptors leads not only to an inward ionic current, but also to cell permeabilization. Second, 3'-O-(4-benzoyl)benzoyl ATP (BZATP) is the most effective agonist, and ATP itself is of rather low potency. Third, responses are strongly inhibited by extracellular magnesium ions, that has been interpreted to indicate that $ATP^{4-}$ is the active agonist (DiVirgilio, Immunol. Today 16:524 (1995)).

A seventh member of the P2X receptor family has been isolated from a rat cDNA library and, when expressed in human embryonic kidney (HEK293) cells, exhibits the above three properties (Surprenant et al, Science 272:735 (1996)). This receptor ($rP2X_7$) thus corresponds to the P2Z receptor. $rP2X_7$ is structurally related to other members of the P2X family but it has a longer cytoplasmic C-terminus domain (there is 35-40% amino acid identity in the corresponding region of homology, but the C-terminus is 239 amino acids long in the $rP2X_7$ receptor compared with 27-20 amino acids in the others). The $rP2X_7$ receptor functions both as a channel permeable to small cations and as a cytolytic pore. Brief applications of ATP (1-2s) transiently open the channel, as is the case of other P2X receptors. Repeated or prolonged applications of agonist cause cell permeabilization reducing the extracellular magnesium concentration potentiates this effect. The unique C-terminal domain of $rP2X_7$ is required for cell permeabilization and the lytic actions of ATP (Suprenant et al, Science 272:735 (1996)).

The $P2Z/rP2X_7$ receptor has been implicated in lysis of antigen-presenting cells by cytotoxic T lymphocytes, in the mitogenic stimulation of human T lymphocytes, as well as in the formation of multinucleated giant cells (Blanchard et al, Blood 85:3173 (1995); Falzoni et al, J. Clin. Invest. 95:1207 (1995); Baricolrdi et al, Blood 87:682 (1996)). Certain functional differences exist between rodent and man (Hickman et al, Blood 84:2452 (1994)). The human macrophage $P2X_7$ receptor ($P2X_7$) has now been cloned and its functional properties determined (Rassendren et al, J. Biol. Chem. 272:5482 (1997). When compared with the rat $P2X_7$ receptor, elicited cation-selective currents in the human $P2X_7$ receptor required higher concentrations of agonists, were more potentiated by removal of extracellular magnesium ions, and revised more rapidly on agonist removal. Expression of chimeric molecules indicated that some of the differences between rat and human $P2X_7$ receptors could be revised by exchanging the respective C-terminal domains of the receptor proteins.

It has been reported that certain compounds act as $P2X_7$ antagonists. For example, WO99/29660 and WO99/29661 disclose that certain adamantane derivatives exhibit $P2X_7$ antagonistic activity having therapeutic efficacy in the treatment of rheumatoid arthritis and psoriasis. Similarly, WO99/29686 discloses that certain heterocyclic derivatives are $P2X_7$ receptor antagonists and are useful as immunosuppressive agents and treating rheumatoid arthritis, asthma, septic shock and atheroscelerosis. Finally, WO00/71529 discloses certain substituted phenyl compounds exhibiting immunosuppressing activity. All of the references described herein are incorporated herein by reference in their entirety.

A need therefore exists for therapeutic agents, and corresponding pharmaceutical compositions and related methods of treatment, that address the conditions causally related to aberrant $P2X_7$ activity, and it is toward the fulfillment and satisfaction of that need, that the present invention is directed.

SUMMARY OF THE INVENTION

Compounds of formulae I-XIj, and their pharmaceutical compositions are disclosed as therapeutic agents useful for the treatment of conditions in mammals associated with abnormal or aberrant activity of the $P2X_7$ receptor, including inflammatory-mediated conditions such as (but not limited to) arthritis, myocardial infarction, the treatment and prophylaxis of pain syndromes (acute and chronic [neuropathic]), traumatic brain injury, acute spinal cord injury, neurodegenerative disorders, inflammatory bowel disease and immune dysfunctions such as autoimmune disorders.

It has now been found that the present compounds are capable of mediating the activity of the $P2X_7$ receptor. This finding leads to novel compounds having therapeutic value. It also leads to pharmaceutical compositions having the compounds of the present invention as active ingredients and to their use to treat, prevent or ameliorate a range of conditions in mammals such as but not limited to inflammation of various genesis or etiology, for example rheumatoid arthritis, cardiovascular disease, inflammatory bowel disease, acute, chronic, inflammatory and neuropathic pain, dental pain and headache (such as migraine, cluster headache and tension headache) and other conditions causally related to inflammation or immune dysfunction.

The compounds of the present invention are also useful for the treatment of inflammatory pain and associated hyperalgesia and allodynia. They are also useful for the treatment of neuropathic pain and associated hyperalgesis and allodynia (e.g. trigeminal or herpetic neuralgia, diabetic neuropathy, causalgia, sympathetically maintained pain and deafferentation syndromes such as brachial plexus avulsion). The compounds of the present invention are also useful as anti-inflammatory agents for the treatment of arthritis, and as agents to treat Parkinson's Disease, uveitis, asthma, myocardial infarction, traumatic brain injury, spinal cord injury, neurodegenerative disorders, inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

In one aspect, this invention provides compounds which may be bicycloheteroaryl and which are capable of modulating the activity of the $P2X_7$ receptor, in vivo. In a further aspect, the compounds of the invention are capable of antagonizing (suppressing or inhibiting) the activity of the $P2X_7$ receptor, and thereby treating those conditions, representative ones of which are causally related to aberrant $P2X_7$ activity.

The compounds of the present invention may show low toxicity, good absorption, good half-life, good solubility, low protein binding affinity, low drug-drug interaction, low inhibitory activity at the HERG channel, low QT prolongation and good metabolic stability.

Accordingly, in a first aspect of the invention, compounds that are capable of capable of modulating the activity of the $P2X_7$ receptor in vivo, are disclosed having a formulae Ia or Ib:

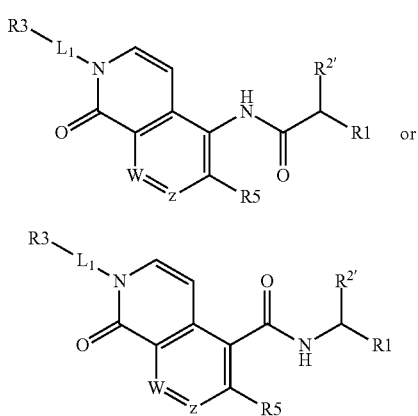

wherein
W is $CR^4$; Z is $CR^4$;
$L^1$ is a single bond, or $C_1$-$C_2$ alkylene, unsubstituted or substituted with alkyl, oxo, or hydroxyalkyl;
$R^1$ is selected from a substituted or unsubstituted 3-13 membered cycloalkyl, and substituted or unsubstituted aryl;
$R^{2'}$ is H or Me;
$R^3$ is selected from hydroxy, amino, alkylamino, and substituted or unsubstituted heterocycloalkyl; provided that when $R^3$ is hydroxy, amino or alkylamino then $L^1$ is other than a bond;

each $R^4$ is independently selected from H, substituted or unsubstituted alkyl, substituted or unsubstituted alkoxy, cyano, substituted or unsubstituted cycloalkyl, substituted or unsubstituted cycloheteroalkyl, halo, and hydroxy;
$R^5$ is selected from substituted or unsubstituted alkyl, substituted or unsubstituted alkoxy, cyano, substituted or unsubstituted cycloalkyl, substituted or unsubstituted cycloheteroalkyl, halo, and hydroxy;
or a pharmaceutically acceptable salt, solvate or prodrug thereof;
and stereoisomers, isotopic variants and tautomers thereof.

In a further embodiment, with respect to compounds of formula I, $L^1$ is —$CH_2CH_2$—.

In a further embodiment, with respect to compounds of formula I, $L^1$ is $C_2$ alkylene substituted with a group selected from Me, i-Bu and hydroxymethyl.

In a further embodiment, with respect to compounds of formula I, $R^1$ is substituted or unsubstituted aryl. In one particular embodiment, $R^1$ is substituted phenyl.

In a further embodiment, with respect to compounds of formula I, $R^1$ is substituted or unsubstituted adamantyl.

In a further embodiment, with respect to compounds of formula I, $R^1$ is substituted or unsubstituted cyclopropyl, cyclopentyl, cyclohexyl or cycloheptyl.

In one embodiment, with respect to compounds of formula I, $R^{2'}$ is H or Me. In another embodiment, $R^{2'}$ is H.

In a further embodiment, with respect to compounds of formula I, $R^3$ is —OH. In another embodiment, $R^3$ is $NH_2$. In yet another embodiment, $R^3$ is substituted amino.

In a further aspect, the present invention provides pharmaceutical compositions comprising a compound of the invention, and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

In a further aspect of the invention, this invention provides a method of treating a mammal susceptible to or afflicted with a condition from among those listed herein, and particularly, such condition as may be associated with e.g. inflammation, such as rheumatoid arthritis, osteoarthritis, uveitis, asthma, myocardial infarction, traumatic brain injury; septic shock, atherosclerosis, chronic pulmonary obstructive disease (COPD), acute spinal cord injury, inflammatory bowel disease and immune dysfunction, including autoimmune disorders, which method comprises administering an effective amount of one or more of the pharmaceutical compositions just described.

In yet another method of treatment aspect, this invention provides a method of treating a mammal susceptible to or afflicted with a condition that is causally related to aberrant $P2X_7$ receptor activity, and that for example, gives rise to pain responses or that relates to imbalances in the maintenance of basal activity of sensory nerves. The amine compounds of the invention have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with conditions that are causally related to abnormal activity of the $P2X_7$ receptor, such as neurodegenerative diseases and disorders including, for example, Parkinson's disease, multiple sclerosis; diseases and disorders which are mediated by or result in neuroinflammation such as, for example traumatic brain injury and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; obesity; lipid disorders; cancer; blood pressure; spinal cord injury; and cardiovascular and renal disorders method comprises administering an effective condition-treating or condition-preventing amount of one or more of the pharmaceutical compositions just described.

In additional aspects, this invention provides methods for synthesizing the compounds of the invention, with representative synthetic protocols and pathways disclosed later on herein.

Accordingly, it is a principal object of this invention to provide a novel series of compounds, which can modify the activity of the $P2X_7$ receptor and thus avert or treat any maladies that may be causally related thereto.

It is further an object of this invention to provide a series of compounds that can treat or alleviate maladies or symptoms of same, such as pain and inflammation, that may be causally related to the activation of the $P2X_7$ receptor.

A still further object of this invention is to provide pharmaceutical compositions that are effective in the treatment or prevention of a variety of disease states, including the diseases associated with the central nervous system, cardiovascular conditions, chronic pulmonary obstructive disease COPD), inflammatory bowel disease, rheumatoid arthritis, osteoarthritis, and other diseases where an inflammatory component is present.

In addition to the methods of treatment set forth above, the present invention extends to the use of any of the compounds of the invention for the preparation of medicaments or as medicaments, that may be administered for such treatments, as well as to such compounds for the treatments disclosed and specified.

Other objects and advantages will become apparent to those skilled in the art from a consideration of the ensuing detailed description.

DETAILED DESCRIPTION OF THE INVENTION

Definitions

The following terms are intended to have the meanings presented therewith below and are useful in understanding the description and intended scope of the present invention.

When describing the compounds, pharmaceutical compositions containing such compounds and methods of using such compounds and compositions, the following terms have the following meanings unless otherwise indicated. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

"Acyl" refers to a radical —C(O)$R^{20}$, where $R^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a radical —$NR^{21}$C(O)$R^{22}$, where $R^{21}$ is hydrogen, alkyl, cycloalkyl, cycloheteroalkyl, aryl, arylalkyl, heteroalkyl, heteroaryl, heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)$R^{23}$ where $R^{23}$ is hydrogen, alkyl, aryl or cycloalkyl.

"Substituted alkenyl" refers to those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —O$R^{24}$ where $R^{24}$ is alkyl Exemplary alkoxy includes methoxy, ethoxy, n-propoxy, i-propoxy, n-butoxy, and heptoxy. Particular alkoxy groups are lower alkoxy, i.e. with between 1 and 6 carbon atoms.

"Substituted alkoxy" refers to those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —$NR^{25}$C(O)O$R^{26}$, where $R^{25}$ is hydrogen, alkyl, aryl or cycloalkyl, and $R^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, iso-propyl, n-butyl, iso-butyl, tert-butyl, n-hexyl, n-octyl, tert-octyl and the like. The term "lower alkyl" refers to alkyl groups having 1 to 6 carbon atoms.

"Substituted alkyl" refers to those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$— , and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" refers to those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group $R^{27}$—C(O)—, where $R^{27}$ is hydrogen or alkyl as defined above.

"Aryl" refers to a monovalent aromatic hydrocarbon group derived by the removal of one hydrogen atom from a single carbon atom of a parent aromatic ring system. Aryl groups may be monocyclic or a bicyclic fused-ring structure where at least one of the rings is an aromatic ring structure that particularly contains 6 carbons. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta 2,4 diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms. Particularly, the aryl group may contain 6 carbon atoms. Exemplary aryl groups include phenyl and indan-1-one.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR$^{28}$R$^{29}$, wherein each of R$^{28}$ and R$^{29}$ are independently selected from hydrogen and alkyl.

"Arylamino" refers to the group aryl-NR$^{30}$R$^{31}$, wherein each of R$^{30}$ and R$^{31}$ are independently selected from hydrogen, aryl and heteroaryl.

"Alkoxyamino" refers to a radical —N(H)OR$^{32}$ where R$^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —NR$^{33}$R$^{34}$ where R$^{33}$ represents an alkyl or cycloalkyl group and R$^{34}$ is an aryl as defined herein.

"Alkylsulfonyl" refers to a radical —S(O)$_2$R$^{35}$ where R$^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R$^{35}$ where R$^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR$^{35}$ where R$^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" refers to those groups recited in the definition of "substituted" herein, and particularly refers to the group —N(R$^{36}$)$_2$ where each R$^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R$^{36}$)$_2$ is an amino group.

"Aminocarbonyl" refers to the group —C(O)NR$^{37}$R$^{37}$ where each R$^{37}$ is independently hydrogen, alkyl, aryl and cycloalkyl, or where the R$^{37}$ groups are joined to form an alkylene group.

"Aminocarbonylamino" refers to the group —NR$^{38}$C(O)NR$^{38}$R$^{38}$ where each R$^{38}$ is independently hydrogen, alkyl, aryl or cycloalkyl, or where two R groups are joined to form an alkylene group.

"Aminocarbonyloxy" refers to the group —OC(O)NR$^{39}$R$^{39}$ where each R$^{39}$ is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —NHR$^{40}$ where R$^{40}$ represents an aryl group as defined herein.

"Aryloxycarbonyl" refers to a radical —C(O)—O-aryl where aryl is as defined herein.

"Arylsulfonyl" refers to a radical —S(O)$_2$R$^{41}$ where R$^{4'}$ is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N(R$^{42}$)$_2$ where each R$^{42}$ group is independently hydrogen, alkyl, cycloalkyl or aryl, as defined herein, which may be optionally substituted as defined herein. In a specific embodiment, the term "carbamoyl" refers to —C(O)—NH$_2$. In an alternative embodiment "carbamoyl lower alkyl" means the radical NH$_2$CO-lower alkyl-. Particular carbamoyl lower alkyl groups include carbamoylethyl and carbamoylmethyl.

"Carboxy" refers to the radical —C(O)OH.

"Carboxyamino" refers to the radical —N(H)C(O)OH.

"Compounds of the present invention", and equivalent expressions, are meant to embrace the compounds as hereinbefore described, in particular compounds according to any of the formulae herein recited and/or described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

"Cycloalkylalkyl" refers to a radical in which a cycloalkyl group is substituted for a hydrogen atom of an alkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocycloalkylalkyl" refers to a radical in which a heterocycloalkyl group is substituted for a hydrogen atom of an alkyl group. Typical heterocycloalkylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Halo" or "halogen" means fluoro (F), chloro (Cl), bromo (Br), or iodo (I).

"Hydrogen" means in the context of a substituent that —H is present at the compound position and also includes its isotope, deuterium.

"Lower alkanoyl amino" means an amino group with an organic functional group R—CO—, where R represents a lower alkyl group.

"Lower alkoxy" means 1 to 6 carbon atoms in a linear alkyl chain that may be straight or branched, and that is bonded by an oxygen atom.

"Lower alkyl sulfonamide" refers to a lower alkyl amide of sulphonamide of the formula —SO$_2$NR*R*, where R* is hydrogen or lower alkyl, and at least one R* is lower alkyl.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like. Particular cycloalkyl groups have between 4 and 7 carbon ring members for example cyclopropyl, cyclobutyl, cyclopentyl, cyclohexyl and cycloheptyl.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR$^{43}$ where R$^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" refers to those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C═C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{46}$, —O$^-$, ═O, —OR$^{46}$, —SR$^{46}$, —S$^-$, ═S, —NR$^{46}$R$^{47}$, ═NR$^{46}$, —CX$_3$, —CF$_3$, —CN, —OCN, —SCN, —NO, —NO$_2$, ═N$_2$, —N$_3$, —S(O)$_2$O$^-$, —S(O)$_2$OH, —S(O)$_2$R$^{46}$, —OS(O$_2$)O$^-$, —OS(O)$_2$R$^{46}$, —P(O)(O$^-$)$_2$, —(O)(OR$^{46}$)(O$^-$), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O$^-$, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted aryl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted-heteroalkyl, heteroaryl, substituted heteroaryl, heteroarylalkyl or substituted heteroarylalkyl.

Examples of representative substituted aryls include the following

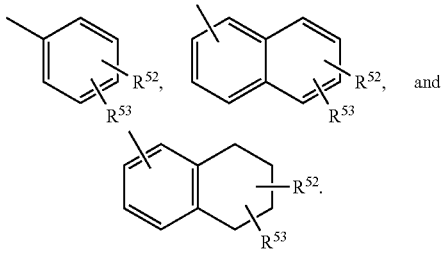

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^{55}$, NR$^{54}$SOR$^{55}$, NR$^{54}$SO2R$^{57}$, COO-alkyl, COO-aryl, CONR$^{54}$R$^{55}$, CONR$^{54}$OR$^{55}$, NR$^{54}$R$^{55}$, SO2NR$^{54}$R$^{55}$, S-alkyl, S-alkyl, SO$_2$-alkyl, S-aryl, SO-aryl, SO$_2$-aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, heterocycloalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. The heteroaryl group may be a monocyclic group (in which case it will typically be a 5 to 7, more typically a 5 or 6 membered ring), alternatively the heteroaryl group may be a bicycloheteroaryl group in particular a fused ring system comprising 2 fused 5-membered rings, a fused 5 and 6 membered ring or two fused 6 membered rings, where the heteroaryl group comprises fused rings at least one of said rings should contain a heteroatom and at least one said rings should be aromatic (both requirements may or may not be fulfilled in the same ring). The heteroaryl group can be, for example, a five membered or six membered monocyclic ring which may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Particularly, the heteroaryl group is between 5-15 membered heteroaryl, with 5-10 membered heteroaryl being particular groups. Particular heteroaryl groups are those derived from thiophene, pyrrole, benzothiophene, benzofuran, indole, pyridine, quinoline, imidazole, oxazole and pyrazine. Particularly, examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Particularly, examples of six membered heteroaryl groups include but are not limited to pyridine, pyrazine, pyridazine, pyrimidine and triazine.

Examples of representative heteroaryls include the following:

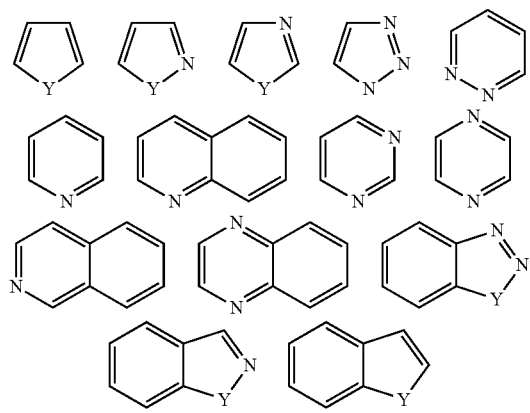

wherein each Y is selected from carbonyl, N, $NR^{58}$, O, and S; and $R^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

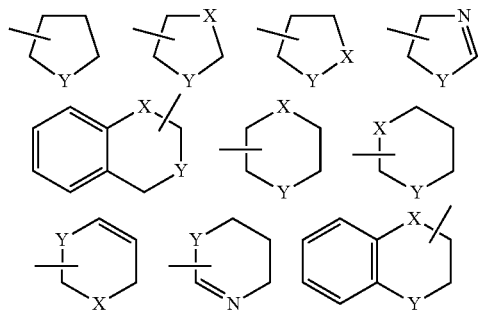

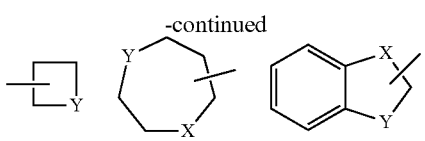

wherein each X is selected from $CR^{58}$, $CR^{58}_2$, $NR^{58}$, O and S; and each Y is selected from $NR^{58}$, O and S; and $R^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy; alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

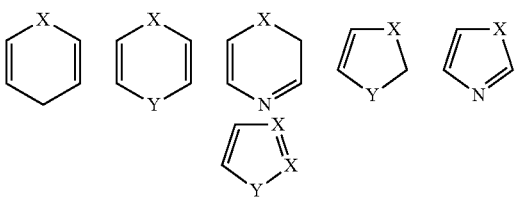

wherein each X is selected from $CR^{58}$, $CR^{58}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

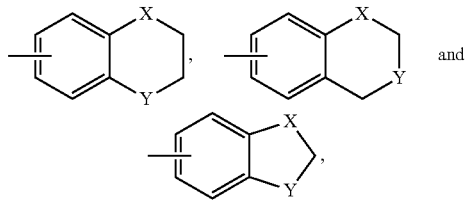

wherein each X is selected from $CR^{58}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an $R^4$ in a $R^4C$ group present as substituents directly on W or Z of the compounds provided herein or may be present as a substituent in the "substituted" aryl and aliphatic groups present in the compounds. Examples of hetero substituents include:

-halo,
—$NO_2$, —$NH_2$, —$N^{59}$, —$N(R^{59})_2$,
—NRCOR, —$NR^{59}SOR^{59}$, —$NR^{59}SO_2R^{59}$, OH, CN,
—$CO_2H$,
—$R^{59}$—OH, —O—$R^{59}$, —$COOR^{59}$, —CON(R$^{59}$)$_2$, —CONROR$^{59}$, —SO$_2$H, —R$^{59}$—S, —SO$_2$N(R$^{59}$)$_2$, —S(O)R$^{59}$, —S(O)$_2$R$^{59}$ wherein each R$^{59}$ is independently an aryl- or aliphatic, optionally with substitution. Among hetero substituents containing R$^{59}$ groups, preference is given to those materials having aryl and alkyl R$^{59}$ groups as defined herein. Preferred hetero substituents are those listed above.

"Hydrogen bond donor" group refers to a group containing O—H, or N—H functionality. Examples of "hydrogen bond donor" groups include —OH, —NH$_2$, and —NH—R$^{59a}$ and wherein R$^{59a}$ is alkyl, acyl, cycloalkyl, aryl, or heteroaryl.

"Dihydroxyphosphoryl" refers to the radical —PO(OH)$_2$.

"Substituted dihydroxyphosphoryl" refers to those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" refers to those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Nitrogen-Containing Heterocycloalkyl" group means a 4 to 7 membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Sulfanyl" refers to the radical HS—. "Substituted sulfanyl" refers to a radical such as RS— wherein R is any substituent described herein. In particular, R is substituted or unsubstituted alkyl substituted or unsubstituted aryl or substituted or unsubstituted heteroaryl.

"Sulfinyl" refers to the divalent radical —S(O)—. "Substituted sulfinyl" refers to a radical such as —SOR$^{61a}$, wherein R$^{61a}$ is any substituent described herein. In particular, R$^{61a}$ is substituted or unsubstituted alkyl, substituted or unsubstituted aryl or substituted or unsubstituted heteroaryl.

"Aminosulfonyl" or "Sulfonamide" refers to the radical H$_2$N(O$_2$)S—, and "substituted aminosulfonyl" or "substituted sulfonamide" refers to a radical such as R$^{62}$$_2$N(O$_2$)S— wherein each R$^{62}$ is independently any substituent described herein.

"Sulfonyl" refers to the divalent radical —S(O$_2$)—. "Substituted sulfonyl" refers to a radical such as —S(O$_2$)R$^{61}$, wherein R$^{61}$ is any substituent described herein. In particular, R$^{61}$ is substituted or unsubstituted alkyl or substituted or unsubstituted aryl.

"Aminosulfonyl" or "Sulfonamide" refers to the radical H$_2$N(O$_2$)S—, and "substituted aminosulfonyl" "substituted sulfonamide" refers to a radical such as R$^{62}$$_2$N(O$_2$)S— wherein each R$^{62}$ is independently any substituent described herein.

"Sulphonamide" refers to a group of compounds containing the chemical group —SO$_2$NH$_2$.

"Sulfone" refers to the group —SO$_2$R$^{63}$. In particular embodiments, R$^{63}$ is selected from lower alkyl, alkyl, aryl and heteroaryl.

"Sulfo" or "sulfonic acid" refers to a radical such as —SO$_3$H.

"Substituted Sulfo" or "sulfonic acid ester" refers to a radical such as —SO$_3$R$^{61b}$ wherein R$^{61b}$ is substituted or unsubstituted alkyl or substituted or unsubstituted aryl.

"Thioalkoxy" refers to the group —SR$^{60}$ where R$^{60}$ is alkyl.

"Substituted thioalkoxy" refers to those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Thioaryloxy" refers to the group —SR$^{64}$ where R$^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable vehicle" refers to a diluent, adjuvant, excipient or carrier with which a compound of the invention is administered.

"Pharmaceutically acceptable salt" refers to the non-toxic, inorganic and organic acid addition salts, and base addition salts, of compounds of the present invention, in particular they are pharmaceutically acceptable and possess the desired pharmacological activity of the parent compound. These salts can be prepared in situ during the final isolation and purification of compounds useful in the present invention. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. Conventional solvents include water, ethanol, acetic acid and the like, therefore, representative solvates include hydrates, ethanolates and methanolates.

"Subject" refers to humans and non-human mammals. The terms "human", "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

"Isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2H$ or D), carbon 13 ($^{13}C$), nitrogen-15 ($^{15}N$), or the like. It will be understood that, in a compound where such isotopic substitution is made, the following atoms, where present, may vary, so that for example, any hydrogen may be 2H/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy. All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

"Tautomers" refer to compounds that are interchangeable forms of a particular compound structure, and that vary in the displacement of hydrogen atoms and electrons. Thus, two structures may be in equilibrium through the movement of τ electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

"Prophylaxis" means a measure taken for the prevention of a disease.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means that amount of a drug or pharmaceutical agent that will elicit the biological or medical response of a subject that is being sought by a medical doctor or other clinician. The "therapeutically effective amount" can vary depending on the compound, the disease and its severity, and the age, weight, etc., of the subject to be treated.

The Compounds

The present invention provides compounds useful for preventing and/or treating a broad range of conditions, associated with abnormalities in the activity of the $P2X_7$ receptor, among them, rheumatoid arthritis, Parkinson's disease, uveitis, asthma, cardiovascular conditions such as myocardial infarction, the treatment and prophylaxis of pain syndromes (acute and chronic or neuropathic), traumatic brain injury, acute spinal cord injury, neurodegenerative disorders, inflammatory bowel disease and immune dysfunctions such as autoimmune disorders or conditions, in mammals.

In a first aspect of the invention, compounds are disclosed that are capable of capable of modulating the activity of the $P2X_7$ receptor in vivo, having a formulae Ia or Ib:

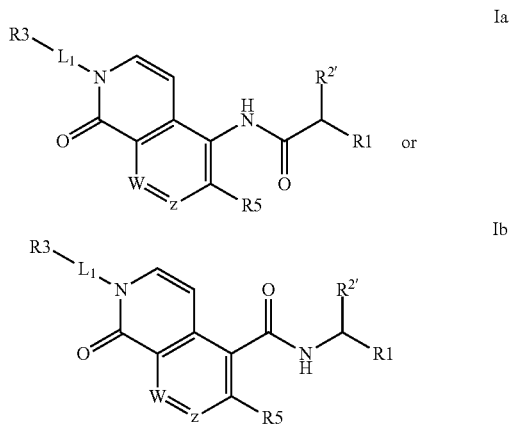

wherein

W is $CR^4$; Z is $CR^4$;

$L^1$ is a single bond, or $C_1$-$C_2$ alkylene, unsubstituted or substituted with alkyl, oxo, or hydroxyalkyl;

$R^1$ is selected from a substituted or unsubstituted 3-13 membered cycloalkyl, and substituted or unsubstituted aryl;

$R^{2'}$ is H or Me;

$R^3$ is selected from hydroxy, amino, alkylamino, and substituted or unsubstituted heterocycloalkyl; provided that when $R^3$ is hydroxy, amino or alkylamino then $L^1$ is other than a bond;

each $R^4$ is independently selected from H, substituted or unsubstituted alkyl, substituted or unsubstituted alkoxy, cyano, substituted or unsubstituted cycloalkyl, substituted or unsubstituted cycloheteroalkyl, halo, and hydroxy;

$R^5$ is selected from substituted or unsubstituted alkyl, substituted or unsubstituted alkoxy, cyano, substituted or unsubstituted cycloalkyl, substituted or unsubstituted cycloheteroalkyl, halo, and hydroxy;

or a pharmaceutically acceptable salt, solvate or prodrug thereof;
and stereoisomers, isotopic variants and tautomers thereof.

In one embodiment, the compound is according to formula Ia:

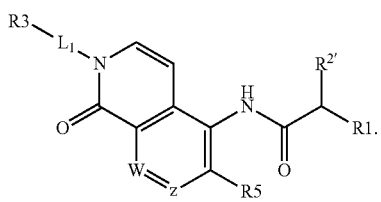

In another embodiment, the compound is according to formula Ib:

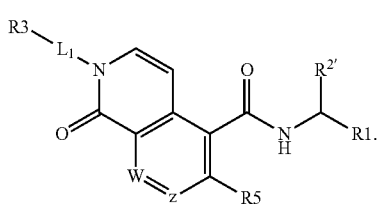

In one embodiment, with respect to formulae Ia-Ib, $R^5$ is selected from alkyl, substituted alkyl, cycloalkyl, substituted cycloalkyl and halo. In one particular embodiment, $R^5$ is selected from Me, cyclopropyl, Cl, F and $CF_3$.

In one embodiment, with respect to formulae Ia-Ib, $R^5$ is Me.

In one embodiment, with respect to formulae Ia-Ib, $R^5$ is $CF_3$.

In one embodiment, with respect to formulae Ia-Ib, $R^5$ is F.

In one embodiment, with respect to formulae Ia-Ib, $R^5$ is Cl.

In one embodiment, with respect to formulae Ia-Ib, $R^5$ is cyclopropyl.

In a further embodiment, with respect to compounds of formulae Ia or Ib, $L^1$ is —$CH_2CH_2$—.

In a further embodiment, with respect to compounds of formulae Ia or Ib, $L^1$ is $C_2$ alkylene substituted with a group selected from Me, i-Bu and hydroxymethyl.

In a further embodiment, with respect to compounds of formulae Ia or Ib, $L^1$ is —$CH_2C(Me)H$—, —$CH_2CMe_2$-, —$CH_2C(i\text{-}Pr)H$—, —$CH_2C(i\text{-}Bu)H$—, —$CH_2C(CH_2OH)H$—, or —$C(Me)HCH_2$—.

In a further embodiment, with respect to compounds of formulae Ia or Ib, $R^1$ is substituted or unsubstituted aryl. In one particular embodiment, $R^1$ is substituted phenyl.

In a further embodiment, with respect to compounds of formulae Ia or Ib, $R^1$ is substituted or unsubstituted adamantyl.

In a further embodiment, with respect to compounds of formulae Ia or Ib, $R^1$ is substituted or unsubstituted cyclopropyl, cyclopentyl, cyclohexyl or cycloheptyl.

In a further embodiment, with respect to compounds of formulae Ia or Ib, $R^1$ is substituted or unsubstituted spiro[2.5]octanyl, or spiro[3.5]nonanyl.

In a further embodiment, with respect to compounds of formulae Ia or Ib, $R^1$ is difluoro substituted spiro[2.5]octanyl, or difluoro substituted spiro[3.5]nonanyl.

In a further embodiment, with respect to compounds of formulae Ia or Ib, $R^1$ is

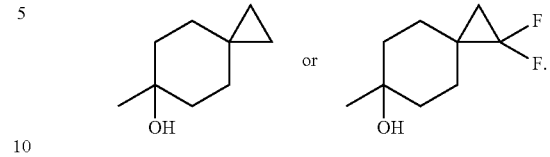

In one embodiment, with respect to compounds of formulae Ia or Ib, $R^{2'}$ is H or Me. In another embodiment, $R^{2'}$ is H.

In a further embodiment, with respect to compounds of formulae Ia or Ib, $L^1$ is other than a bond, and $R^3$ is —OH. In another embodiment, $L'$ is other than a bond, and $R^3$ is $NH_2$. In yet another embodiment, $L^1$ is other than a bond, and $R^3$ is substituted amino.

In one embodiment, with respect to formulae Ia-Ib, the compound is according to formulae IIa or IIb:

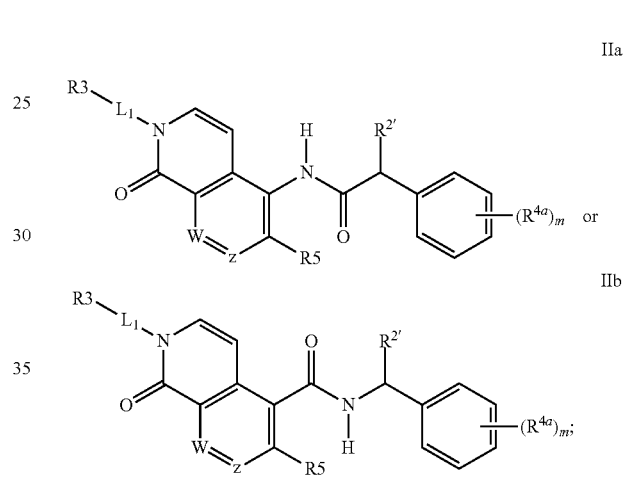

wherein
W, Z, $L^1$, $R^2$, $R^3$, $R^4$ and $R^5$ are as defined with respect to formulae Ia-Ib;
each $R^{4a}$ is independently selected from H, substituted or unsubstituted alkyl, substituted or unsubstituted acyl, substituted or unsubstituted acylamino, substituted or unsubstituted alkylamino, substituted or unsubstituted alkythio, substituted or unsubstituted alkoxy, substituted or unsubstituted alkoxycarbonyl, substituted or unsubstituted alkylarylamino, substituted or unsubstituted arylalkyloxy, substituted or unsubstituted amino, substituted or unsubstituted aryl, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol; and m is selected from 0-5;
or a pharmaceutically acceptable salt, solvate or prodrug thereof;
and stereoisomers, isotopic variants and tautomers thereof.

In one embodiment, with respect to formulae IIa or IIb, m is 1, 2 or 3.

In one embodiment, with respect to formulae IIa or IIb, m is 1.

In one embodiment, with respect to formulae IIa or IIb, m is 2.

In one embodiment, with respect to formulae IIa or IIb, each $R^{4a}$ is H.

In one embodiment, with respect to formulae IIa or IIb, each $R^{4a}$ is independently selected from substituted or unsubstituted alkyl, halo, CN, alkoxy, substituted sulfonyl, sulfo, substituted sulfo, substituted or unsubstituted phenyl, or substituted or unsubstituted heteroaryl.

In one embodiment, with respect to formulae IIa or IIb, each $R^{4a}$ is independently selected from substituted or unsubstituted alkyl, and halo.

In one embodiment, with respect to formulae IIa or IIb, m is 2; and each $R^{4a}$ is independently selected from substituted or unsubstituted alkyl, and halo.

In one embodiment, with respect to formulae IIa or IIb, each $R^{4a}$ is independently selected from Me, Et, Ph, Cl, F, Br, CN, OH, OMe, OEt, OPh, COPh, $CF_3$, $CHF_2$, $OCF_3$, i-Pr, i-Bu, t-Bu, SMe, CH=CH—$CO_2H$, SOMe, $SO_2Me$, $SO_3H$, $SO_3Me$, and pyridyl.

In one embodiment, with respect to formulae IIa or IIb, m is 2; and each $R^{4a}$ is independently selected from Me, Et, Ph, Cl, F, Br, CN, OH, OMe, OEt, OPh, COPh, $CF_3$, $CHF_2$, $OCF_3$, i-Pr, i-Bu, t-Bu, SMe, CH=CH—$CO_2H$, SOMe, $SO_2Me$, $SO_3H$, $SO_3Me$, and pyridyl.

In one embodiment, with respect to formulae IIa or IIb, m is 2; and each $R^{4a}$ is independently selected from Me, Et, Cl, F, $CF_3$; and $CHF_2$.

In one embodiment, with respect to formulae IIa or IIb, m is 2; and each $R^{4a}$ is independently selected from Me, Cl, F, and $CF_3$.

In one embodiment, with respect to formulae IIa or IIb, m is 2; and each $R^{4a}$ is independently selected from Cl, F, and $CF_3$.

In one embodiment, with respect to formulae Ia-Ib, the compound is according to formulae IIIa or IIIb:

IIIa

IIIb wherein
W, Z, $L^1$, $R^{2'}$, $R^3$, $R^4$ and $R^5$ are as defined with respect to formulae Ia-Ib;
Cy is adamantyl, cyclohexyl or cycloheptyl; m is 0, 1, 2 or 3; and each $R^{4b}$ is independently selected from H, $C_1$-$C_4$ alkyl, halo, and hydroxy; or when m is >2, and two of $R^{4b}$ are independently alkyl, then they may join together to form a cycloalkyl ring of 3-7 atoms;

or a pharmaceutically acceptable salt, solvate or prodrug thereof;

and stereoisomers, isotopic variants and tautomers thereof.

In one embodiment, with respect to formulae IIIa or IIIb, Cy is adamantyl.

In one embodiment, with respect to formulae IIIa or IIIb, Cy is cycloheptyl.

In one embodiment, with respect to formulae IIIa or IIIb, Cy is cyclohexyl.

In one embodiment, with respect to formulae IIIa or IIIb, m is 0, 1, 2 or 3.

In one embodiment, with respect to formulae IIIa or IIIb, m is 0.

In one embodiment, with respect to formulae IIIa or IIIb, m is 1.

In one embodiment, with respect to formulae IIIa or IIIb, each $R^{4b}$ is H.

In one embodiment, with respect to formulae IIIa or IIIb, each $R^{4b}$ is selected from selected from Me, Et, Cl, F, OH, $CF_3$, i-Pr, i-Bu and t-Bu.

In one embodiment, with respect to formulae IIIa or IIIb, m is 1; and $R^{4b}$ is selected from selected from $C_1$-$C_4$ alkyl, halo, and hydroxy.

In one embodiment, with respect to formulae IIIa or IIIb, m is 1; and $R^{4b}$ is Me, Et or $CF_3$.

In one embodiment, with respect to formulae IIIa or IIIb, m is 1; and $R^{4b}$ is Me, or Et.

In one embodiment, with respect to formulae IIIa or IIIb, m is 1; and $R^{4b}$ is Cl, or F.

In one embodiment, with respect to formulae IIIa or IIIb, m is 1; and $R^{4b}$ is OH.

In one embodiment, with respect to formulae Ia-IIIb, $R^1$ is selected from

In one embodiment, with respect to formulae Ia-IIIb, W is CH.

In one embodiment, with respect to formulae Ia-IIIb, Z is CH.

In one embodiment, with respect to formulae Ia-IIIb, each W and Z each CH.

In one embodiment, with respect to formulae Ia-IIIb, each $R^4$ is independently selected from Me, Et, Ph, Cl, F, Br, CN, OH, OMe, OEt, OPh, COPh, $CF_3$, $CHF_2$, $OCF_3$, i-Pr, i-Bu, t-Bu, SMe, CH=CH—$CO_2$H, SOMe, $SO_2$Me, $SO_3$H, $SO_3$Me, and pyridyl.

In one embodiment, with respect to formulae Ia-IIIb, each $R^4$ is independently selected from Me, Et, $CF_3$, $CHF_2$, i-Pr, i-Bu, and t-Bu.

In one embodiment, with respect to formulae Ia-IIIb, each $R^4$ is independently selected from Cl and F.

In one embodiment, with respect to formulae Ia-IIIb, each $R^4$ is independently selected from OH, OMe, OEt, OPh, and $OCF_3$.

In one embodiment, with respect to formulae Ia-IIIb, each $R^4$ is independently selected from SMe, SOMe, $SO_2$Me, $SO_3$H, and $SO_3$Me.

In one embodiment, with respect to formulae Ia-IIIb, W is $CR^4$ and $R^4$ is selected from Me, Et, Ph, Cl, F, Br, CN, OH, OMe, OEt, OPh, COPh, $CF_3$, $CHF_2$, $OCF_3$, i-Pr, i-Bu, t-Bu, SMe, CH=CH—$CO_2$H, SOMe, $SO_2$Me, $SO_3$H, $SO_3$Me, and pyridyl.

In one embodiment, with respect to formulae Ia-IIIb, Z is $CR^4$ and $R^4$ is selected from Me, Et, Ph, Cl, F, Br, CN, OH, OMe, OEt, OPh, COPh, $CF_3$, $CHF_2$, $OCF_3$, i-Pr, i-Bu, t-Bu, SMe, CH=CH—$CO_2$H, SOMe, $SO_2$Me, $SO_3$H, $SO_3$Me, and pyridyl.

In one embodiment, with respect to formulae Ia-IIIb, W is $CR^4$ and $R^4$ is selected from Me, Et, Ph, Cl, F, Br, CN, OH, OMe, OEt, OPh, COPh, $CF_3$, $CHF_2$, $OCF_3$, i-Pr, i-Bu, t-Bu, SMe, CH=CH—$CO_2$H, SOMe, $SO_2$Me, $SO_3$H, $SO_3$Me, and pyridyl; and Z is CH.

In one embodiment, with respect to formulae Ia-IIIb, Z is $CR^4$ and $R^4$ is selected from Me, Et, Ph, Cl, F, Br, CN, OH, OMe, OEt, OPh, COPh, $CF_3$, $CHF_2$, $OCF_3$, i-Pr, i-Bu, t-Bu, SMe, CH=CH—$CO_2$H, SOMe, $SO_2$Me, $SO_3$H, $SO_3$Me, and pyridyl; and W is CH.

In one embodiment, with respect to compounds of formulae Ia-IIIb, $R^{2'}$ is H or Me. In another embodiment, $R^{2'}$ is H. In another embodiment, $R^{2'}$ is Me.

In one embodiment, with respect to formulae Ia-IIIb, $R^3$ is selected from hydroxyl, amino, and alkylamino.

In one embodiment, with respect to formulae Ia-IIIb, $R^3$ is substituted or unsubstituted heterocycloalkyl.

In one embodiment, with respect to formulae Ia-IIIb, the group -$L_1$-$R^3$ is selected from

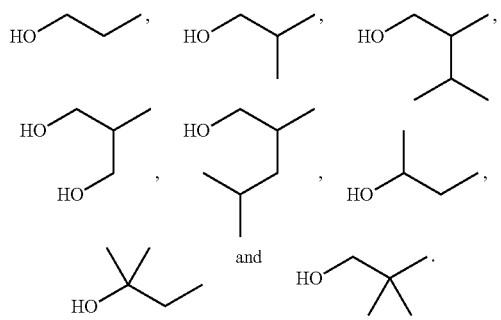

In one embodiment, with respect to formulae Ia-IIIb, the group -$L_1$-$R^3$ is selected from

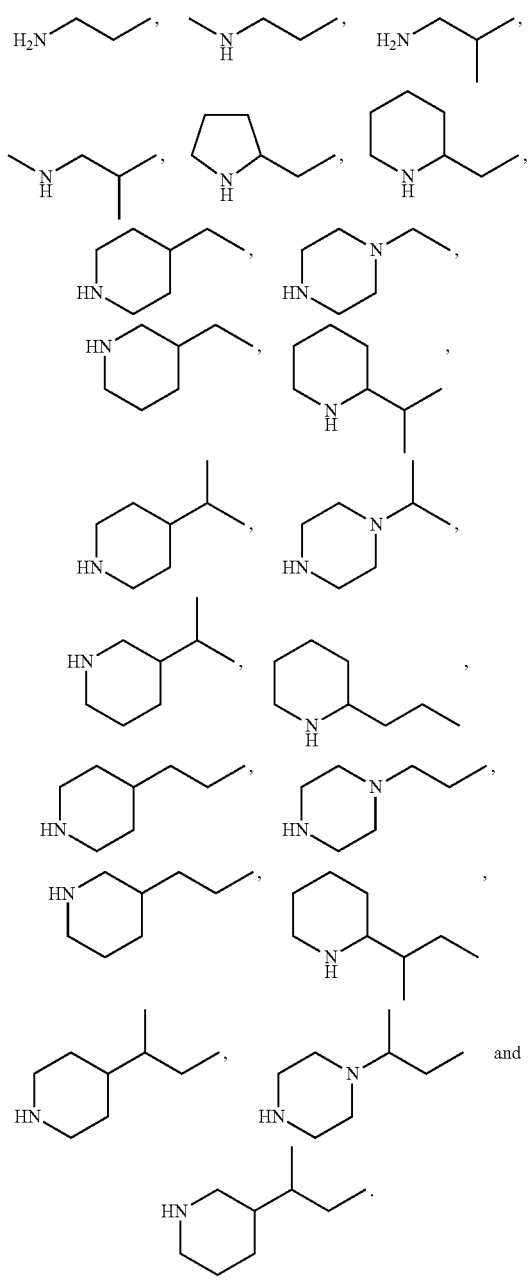

In one embodiment, with respect to formulae Ia-IIIb, the group -$L_1$-$R^3$ is selected from

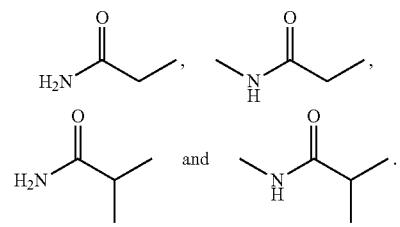

In one embodiment, with respect to formulae Ia-IIIb, the group -$L_1$-$R^3$ is selected from

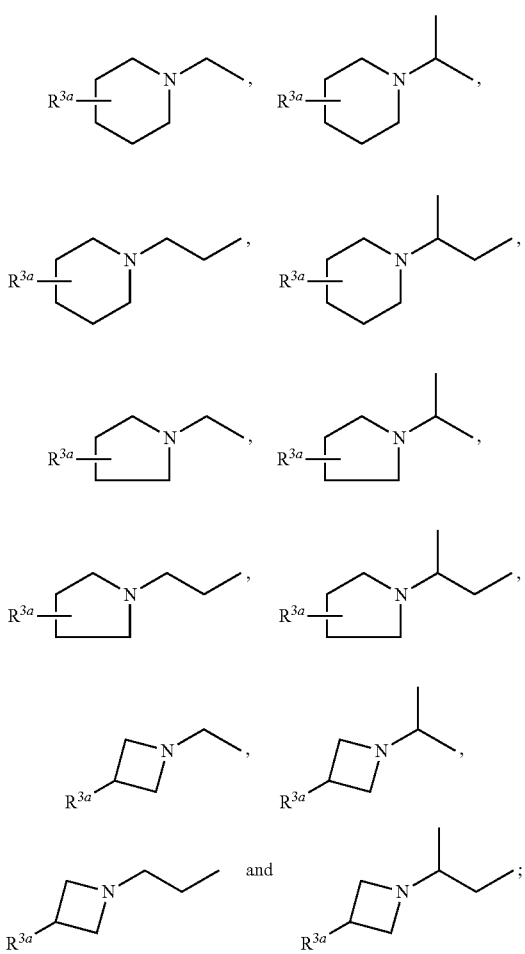

and wherein $R^{3a}$ is OH, NHMe or $NH_2$.

Where appearing herein, the group -$L^1$-$R^3$ may be depicted structurally. In such instance, the longer bond shown in the following drawing is intended to identify the bond between the $L^1$-$R^3$ group and the point of its attachment to the core structure. For example, when -$L^1$-$R^3$ is

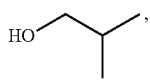

it is attached to a core structure via the longer bond, and the resulting structures would be as depicted below with respect to exemplary formulae Ic or Id:

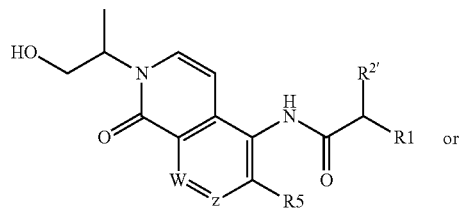

Ic

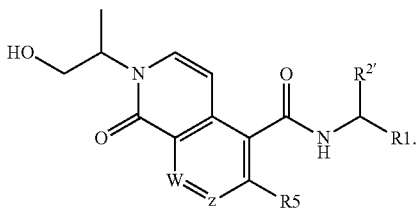

Id

The particular structure and conformation of a given molecule including the -$L^1$-$R^3$ group may vary, and the foregoing depiction is presented for purposes of illustration and not limitation, and in fulfillment of the best mode of practicing the invention.

In one embodiment, $R^{3a}$ is OH. In another embodiment, $R^{3a}$ is NHMe. In yet another embodiment, $R^{3a}$ is $NH_2$.

In one embodiment, with respect to formula Ia, the compound is according to formula IVa, IVb, IVc, IVd, IVe, IVf, IVg or IVh:

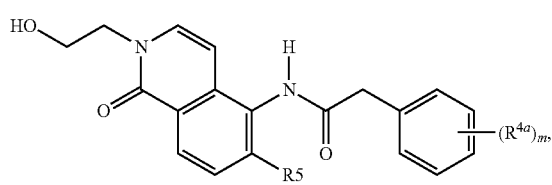

IVa

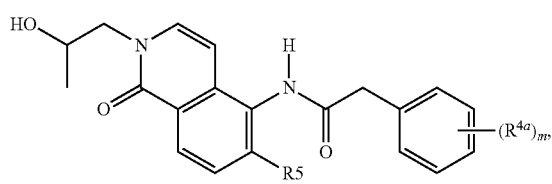

IVb

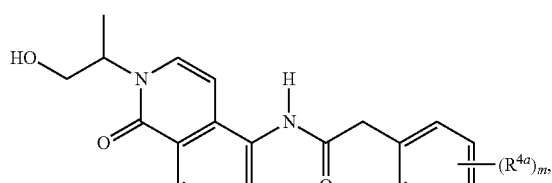

IVc

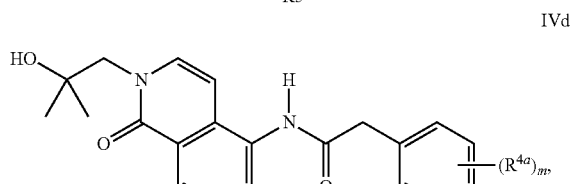

IVd

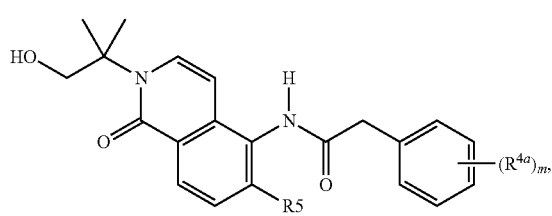

IVe

IVf

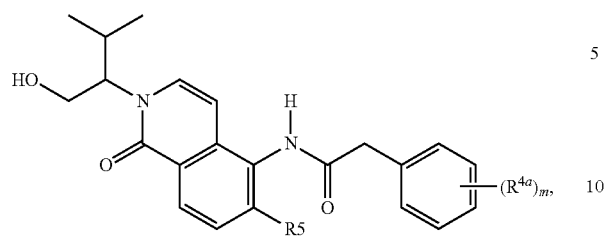

IVg

IVh

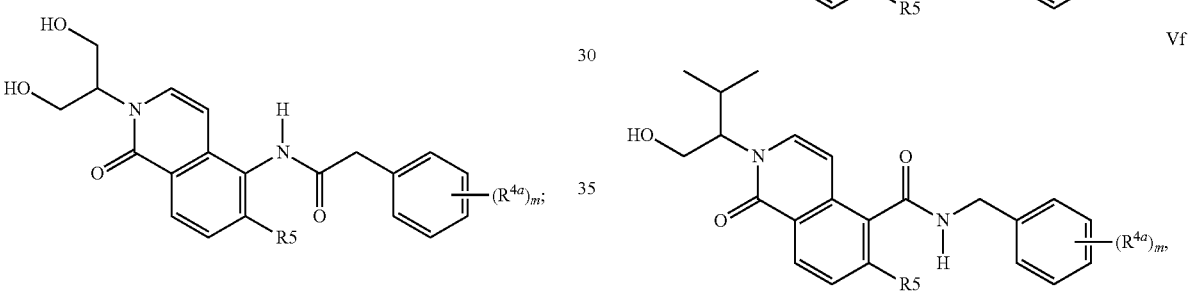

wherein each $R^{4a}$ is independently selected from hydrogen, alkyl, substituted alkyl, substituted or unsubstituted alkoxy, cyano, halo, and hydroxy; and m is selected from 0-5; and $R^5$ is selected from alkyl, cycloalkyl, or halo.

In one embodiment, with respect to formula Ib, the compound is according to formulae Va, Vb, Vc, Vd, Ve, Vf, Vg, Vh, Vi or Vi:

Va

Vb

Vc

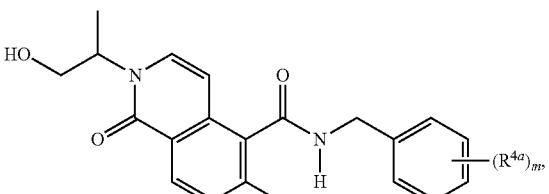

Vd

Ve

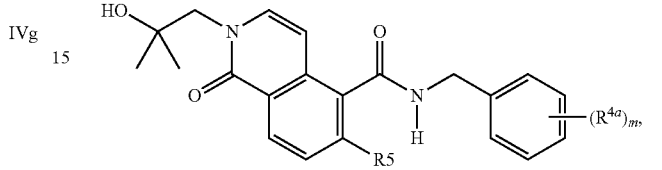

Vf

Vg

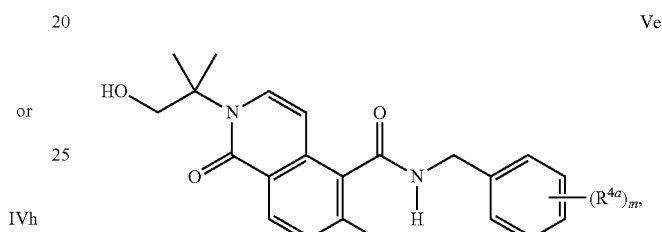

Vh

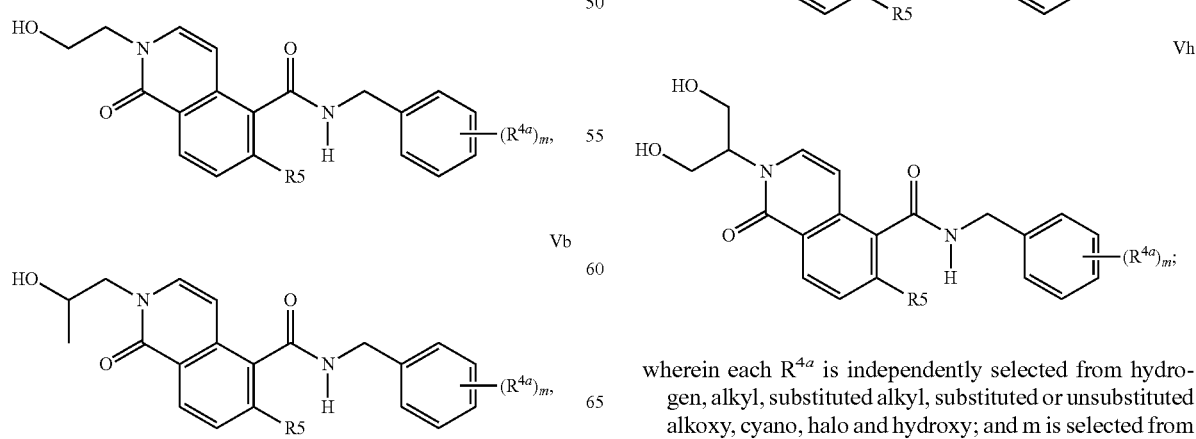

wherein each $R^{4a}$ is independently selected from hydrogen, alkyl, substituted alkyl, substituted or unsubstituted alkoxy, cyano, halo and hydroxy; and m is selected from 0-5; and $R^5$ is selected from alkyl, cycloalkyl or halo.

In one embodiment, with respect to formula Ia, the compound is according to formulae VIa, VIb, VIc, VId, VIe, VIf, VIg, VIh, VIi or VIj:

VIa
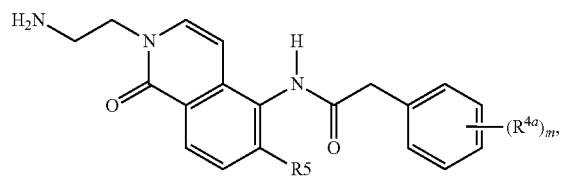

VIb
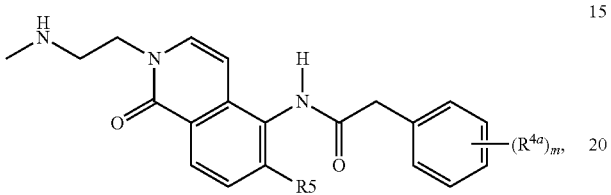

VIc
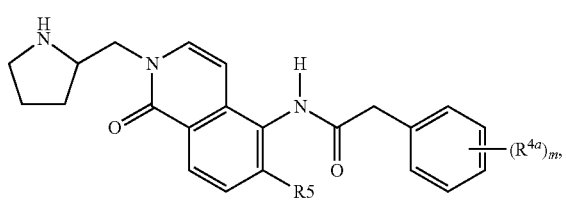

VId
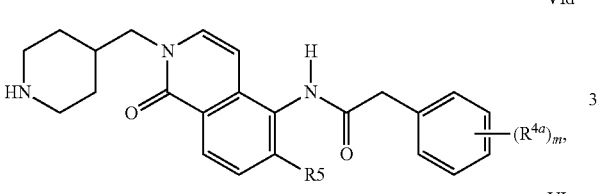

VIe
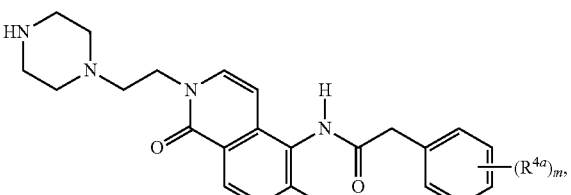

VIf
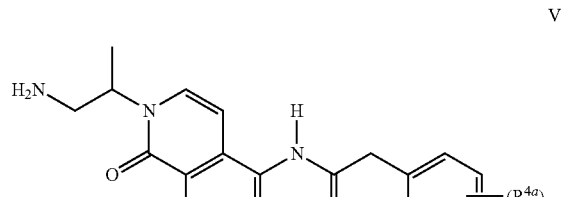

VIg
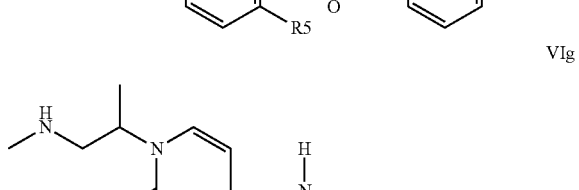

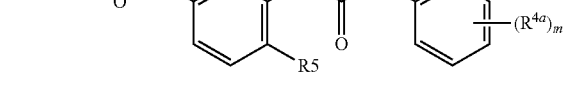

VIh
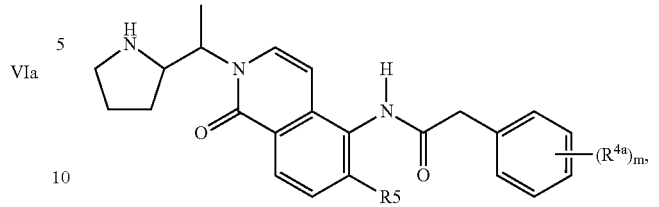

VIi
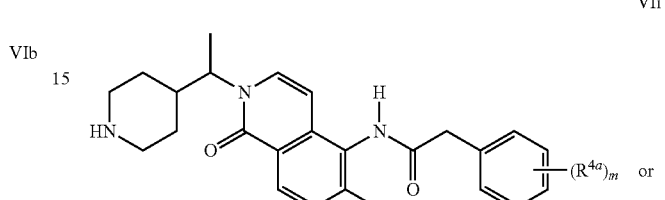

or

VIj
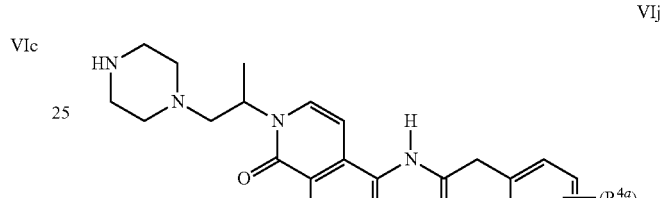

wherein each $R^{4a}$ is independently selected from hydrogen, alkyl, substituted alkyl, substituted or unsubstituted alkoxy, cyano, halo, and hydroxy; and m is selected from 0-5; and $R^5$ is selected from alkyl, cycloalkyl, or halo.

In one embodiment, with respect to formula Ib, the compound is according to formulae VIIa, VIIb, VIIc, VIId, VIIe, VIIf, VIIg, VIIh, VIIi or VIIj:

VIIa
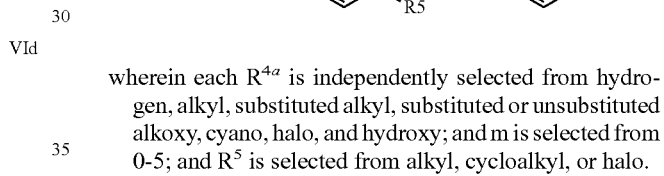

VIIb
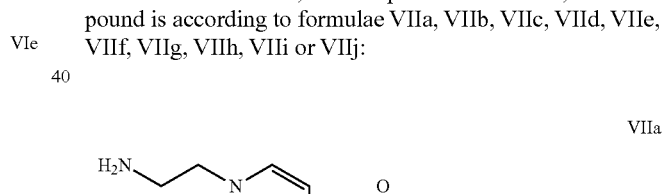

VIIc
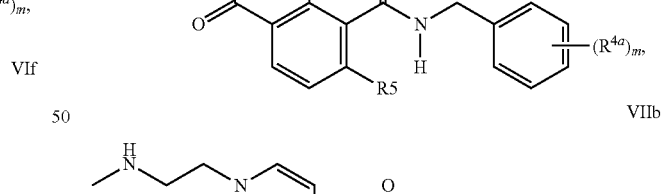

-continued

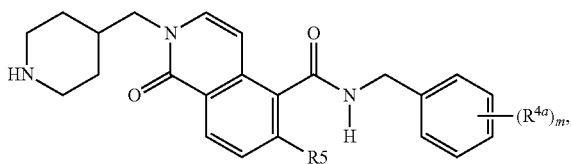

VIId

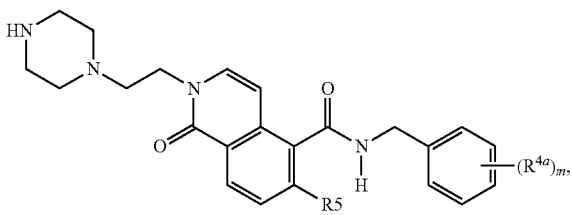

VIIe

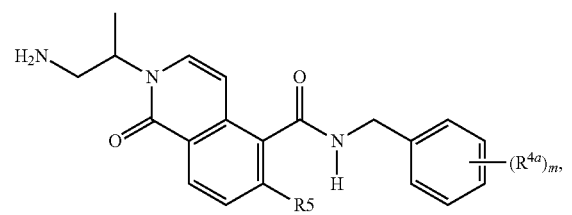

VIIf

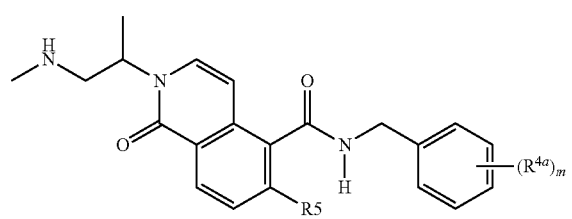

VIIg

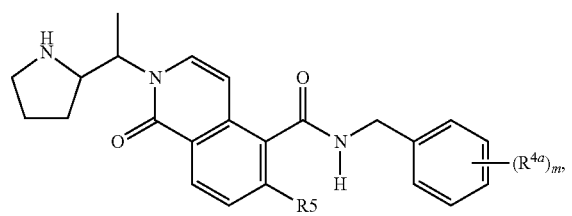

VIIh

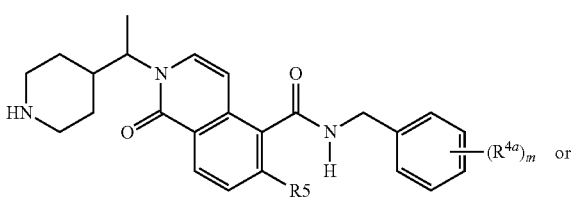

VIIi

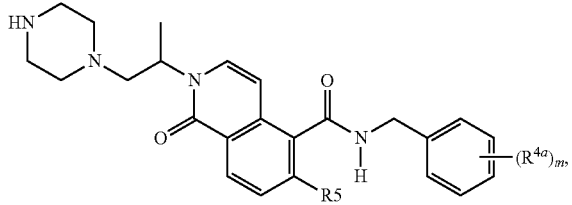

VIIj wherein each $R^{4a}$ is independently selected from hydrogen, alkyl, substituted alkyl, substituted or unsubstituted alkoxy, cyano, halo, and hydroxy; and m is selected from 0-5; and $R^5$ is selected from alkyl, cycloalkyl, or halo.

In one embodiment, with respect to formulae IVa-VIIj, m is 5 and each $R^{4a}$ is H.

In one embodiment, with respect to formulae IVa-VIIj, m is 1 or 2.

In one embodiment, with respect to formulae IVa-VIIj, m is 2.

In one embodiment, with respect to formulae IVa-VIIj, each $R^{4a}$ is independently selected from alkyl, substituted alkyl, substituted or unsubstituted alkoxy, cyano, halo, and hydroxy.

In one embodiment, with respect to formulae IVa-VIIj, m is 1; and $R^{4a}$ is selected from alkyl, substituted alkyl, substituted or unsubstituted alkoxy, cyano, halo, and hydroxy.

In one embodiment, with respect to formulae IVa-VIIj, m is 1; and $R^{4a}$ is selected from alkyl, and substituted alkyl.

In one embodiment, with respect to formulae IVa-VIIj, m is 1; and $R^{4a}$ is selected from Me, Et, i-Pr, and $CF_3$.

In one embodiment, with respect to formulae IVa-VIIj, m is 1; and $R^{4a}$ is halo. In another embodiment, $R^{4a}$ is Cl. In yet another embodiment, $R^{4a}$ is F.

In one embodiment, with respect to formulae IVa-VIIj, m is 2; and each $R^{4a}$ is selected from alkyl, substituted alkyl, substituted or unsubstituted alkoxy, cyano, halo, and hydroxy.

In one embodiment, with respect to formulae IVa-VIIj, each $R^{4a}$ is independently selected from substituted or unsubstituted alkyl, and halo.

In one embodiment, with respect to formulae IVa-VIIj, m is 2; and each $R^{4a}$ is independently selected from substituted or unsubstituted alkyl, and halo.

In one embodiment, with respect to formulae IVa-VIIj, m is 2; and each $R^{4a}$ is independently selected from Me, Et, Cl, F, Br, CN, OH, OMe, OEt, OPh, $CF_3$, $CHF_2$, $OCF_3$, i-Pr, i-Bu, and t-Bu.

In one embodiment, with respect to formulae IVa-VIIj, m is 2; and each $R^{4a}$ is independently selected from Me, Et, Cl, F, $CF_3$, and $CHF_2$.

In one embodiment, with respect to formulae IVa-VIIj, m is 2; and each $R^{4a}$ is independently selected from Me, Cl, F, and $CF_3$.

In one embodiment, with respect to formulae IVa-VIIj, m is 2; and each $R^{4a}$ is independently selected from Cl, F, and $CF_3$.

In one embodiment, with respect to formulae IVa-VIIj, m is 1 and $R^{4a}$ is $CF_3$.

In one embodiment, with respect to formulae IVa-VIIj, m is 2 and one $R^{4a}$ is F or Cl; and the other $R^{4a}$ is $CF_3$.

In one embodiment, with respect to formulae IVa-VIIj, m is 2 and one $R^{4a}$ is F; and the other $R^{4a}$ is $CF_3$.

In one embodiment, with respect to formulae IVa-VIIj, m is 2 and one $R^{4a}$ is Cl; and the other $R^{4a}$ is $CF_3$.

In one embodiment, with respect to formulae IVa-VIIj, m is 2 and each $R^{4a}$ is independently selected from F and Cl.

In one embodiment, with respect to formulae IVa-VIIj, m is 2 and one $R^{4a}$ is F; and the other $R^{4a}$ is F.

In one embodiment, with respect to formulae IVa-VIIj, m is 2 and one $R^{4a}$ is Cl; and the other $R^{4a}$ is Cl.

In one embodiment, with respect to formulae IVa-VIIj, m is 2 and one $R^{4a}$ is F; and the other $R^{4a}$ is Cl.

In one embodiment, with respect to formula Ia, the compound is according to formulae VIIIa, VIIIb, VIIIc, VIIId, VIIIe, VIIIf, VIIIg, or VIIIh:

VIIIa
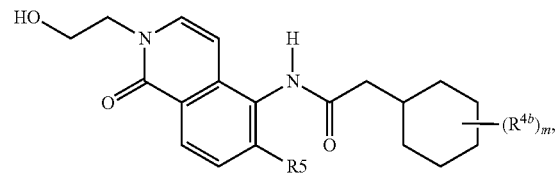
VIIIb
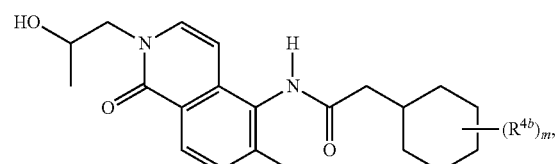
VIIIc
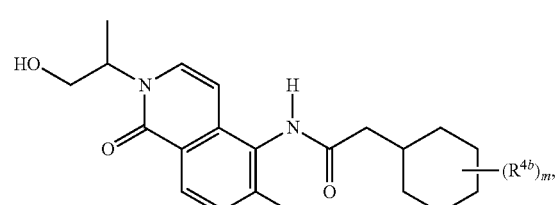
VIIId
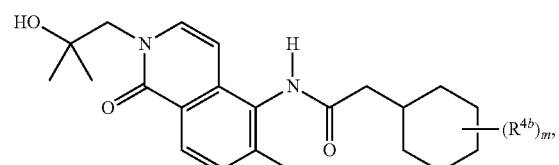
VIIIe
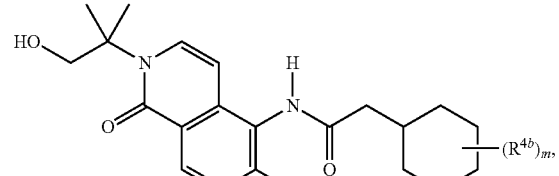
VIIIf
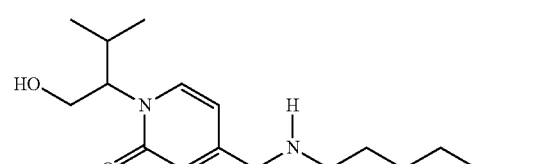
VIIIg
or
VIIIh
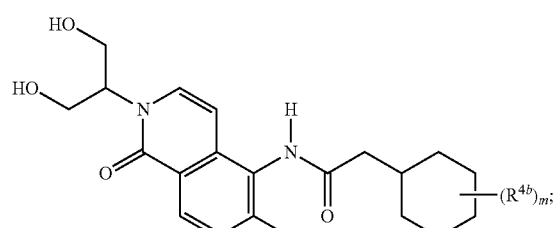
wherein each $R^{4b}$ is independently selected from H, Me, Cl, F and OH; and m is selected from 1-3; and $R^5$ is selected from alkyl, cycloalkyl or halo.
In one embodiment, with respect to formula Ib, the compound is according to formula IXa, IXb, IXc, IXd, IXe, IXf, IXg or IXh:
IXa
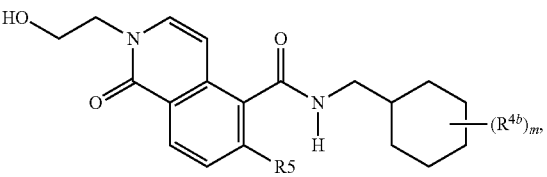
IXb
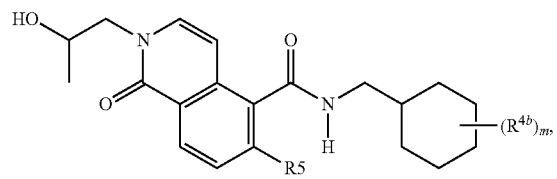
IXc
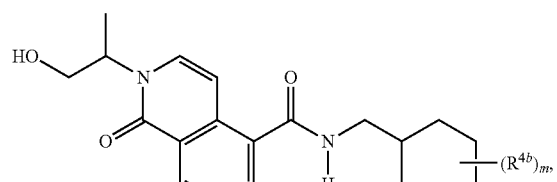
IXd
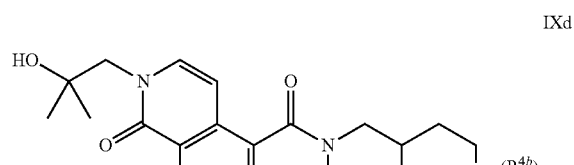
IXe
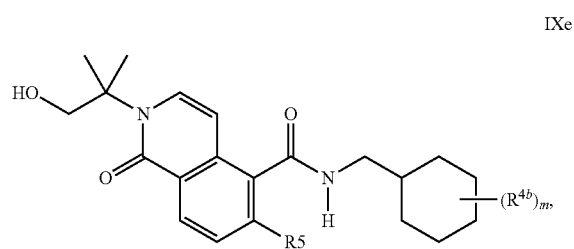

-continued
IXf
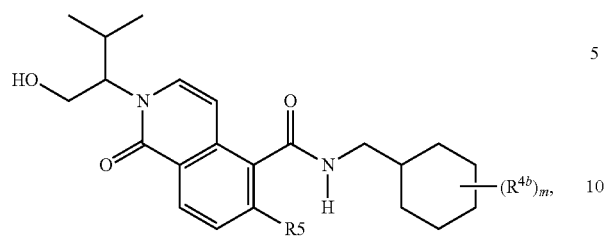
IXg
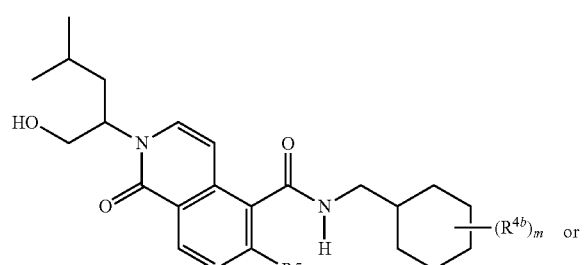    or
IXh
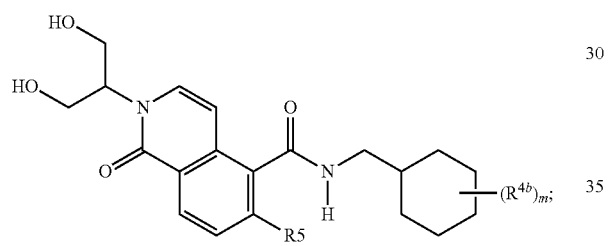
wherein each $R^{4b}$ is independently selected H, Me, Cl, F and OH; and m is selected from 1-3; and $R^5$ is selected from alkyl, cycloalkyl or halo.
In one embodiment, with respect to formula Ia, the compound is according to formulae Xa, Xb, Xc, Xd, Xe, Xf, Xg, Xh, Xi or Xj:
-continued
Xc
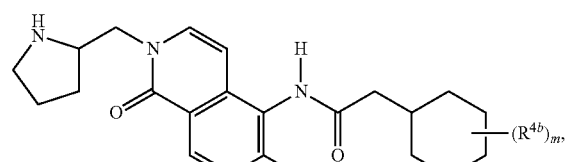
Xd
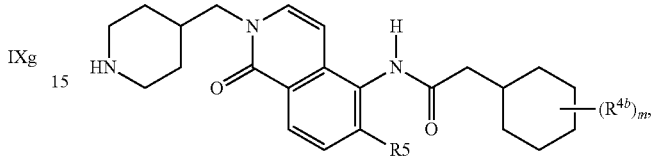
Xe
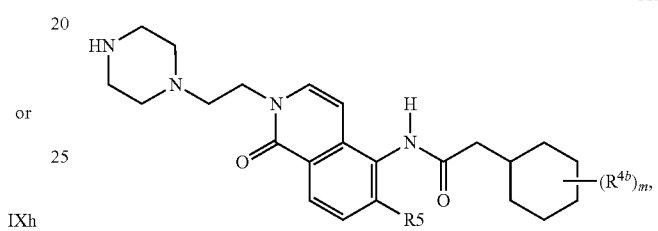
Xf
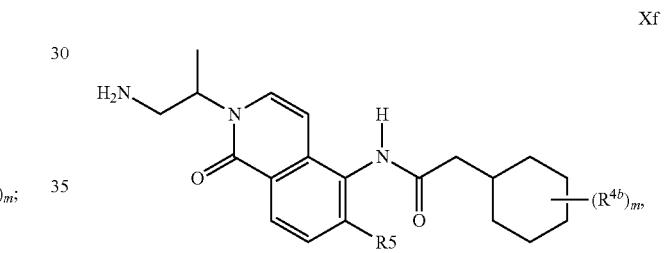
Xg
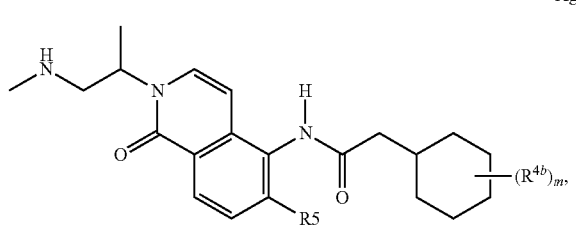
Xh
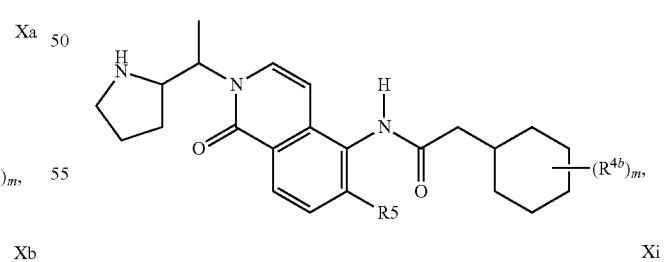
Xi
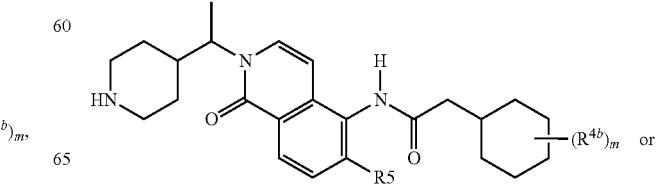   or
Xa
Xb

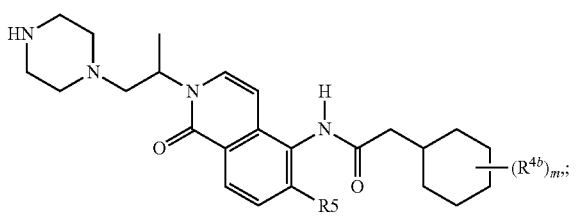

wherein each $R^{4b}$ is independently selected H, Me, Cl, F and OH; and m is selected from 1-3; and $R^5$ is selected from alkyl, cycloalkyl or halo.

In one embodiment, with respect to formula Ib, the compound is according to formulae XIa, XIb, XIc, XId, XIe, XIf, XIg, XIh, XIi or XIj:

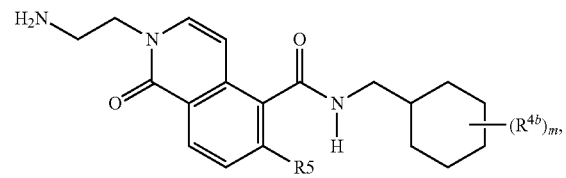

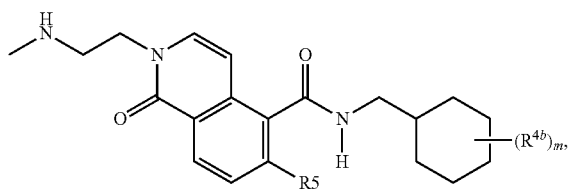

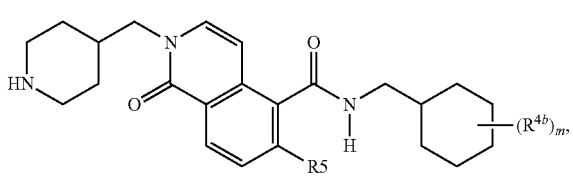

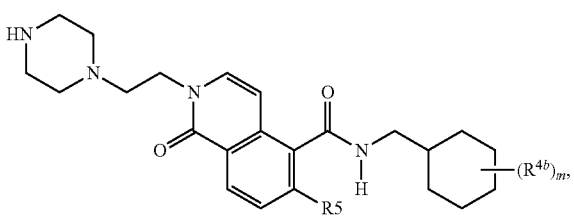

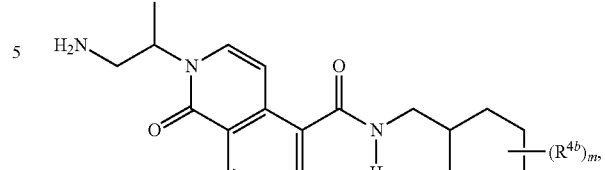

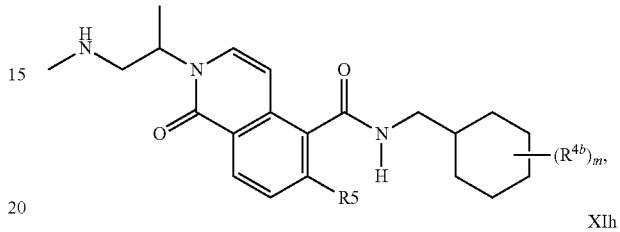

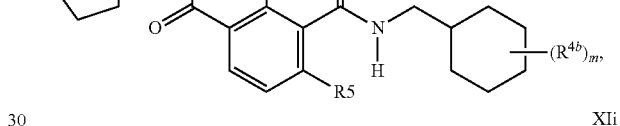

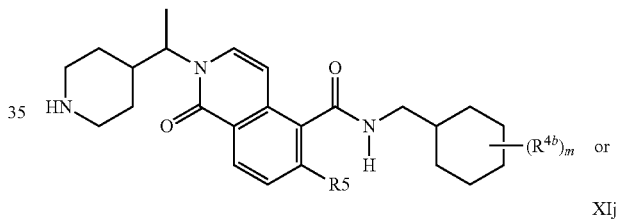

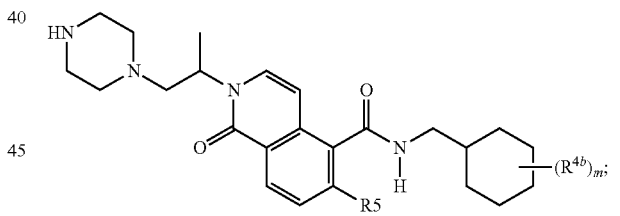

wherein each $R^{4b}$ is independently selected H, Me, Cl, F and OH; and m is selected from 1-3; and $R^5$ is selected from alkyl, cycloalkyl or halo.

In one embodiment, with respect to formulae VIIIa-XIj, m is 1 or 2.

In one embodiment, with respect to formulae VIIIa-XIj, m is 2.

In one embodiment, with respect to formulae VIIIa-XIj, $R^{4b}$ is H.

In one embodiment, with respect to formulae VIIa-XIj, m is 1 and $R^{4b}$ is selected from Me, F and OH.

In one embodiment, with respect to formulae VIIIa-XIj, m is 1 and $R^{4b}$ is 1-OH or 4-F.

In one embodiment, with respect to formulae VIIIa-XIj, m is 2 and each $R^{4b}$ is selected from Me, F and OH.

In one embodiment, with respect to formulae VIIIa-XIj, m is 2 and one $R^{4b}$ is 3-F and the other is 3-F.

In one embodiment, with respect to formulae VIIIa-XIj, m is 2 and one $R^4b$ is 4-F and the other is 4-F.

In one embodiment, with respect to formulae VIIIa-XIj, m is 2 and $R^{4b}$ is 3,3- or 4,4-diF.

In one embodiment, with respect to formulae VIIIa-XIj, m is 2 and one $R^{4b}$ is 1-OH and the other is 4-F.

In one embodiment, with respect to formulae VIIIa-XIj, m is 3 and $R^{4b}$ is selected from Me, F, and OH.

In one embodiment, with respect to formulae VIIIa-XIj, m is 3; one $R^{4b}$ is 1-OH; and the rest are 4,4-diF or 3,3-diF.

In one embodiment, with respect to formulae VIIIa-XIj, m is 3; one $R^{4b}$ is 1-OH; the other two are alkyls. In another embodiment, the two alkyls are joined together to form a substituted or unsubstituted cyclopropyl or cyclobutyl ring.

In one embodiment, with respect to formulae VIIIa-XIj,

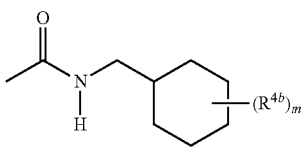

is replaced with

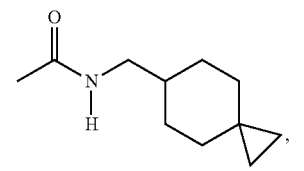,

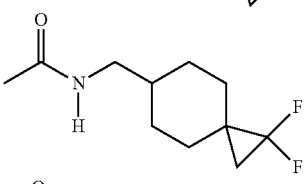

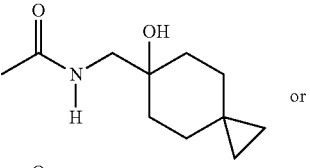 or

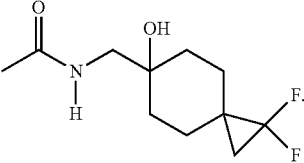.

In one embodiment, with respect to formulae I-XIj, $R^5$ is selected from alkyl, substituted alkyl, cycloalkyl, substituted cycloalkyl and halo. In one particular embodiment, $R^5$ is selected from Me, cyclopropyl, Cl, F and $CF_3$.

In one embodiment, with respect to formulae I-XIj, $R^5$ is alkyl.

In one embodiment, with respect to formulae I-XIj, $R^3$ is substituted alkyl.

In one embodiment, with respect to formulae I-XIj, $R^5$ is cycloalkyl.

In one embodiment, with respect to formulae I-XIj, $R^5$ is substituted cycloalkyl.

In one embodiment, with respect to formulae I-XIj, $R^5$ is halo.

In one embodiment, with respect to formulae I-XIj, $R^5$ is Me.

In one embodiment, with respect to formulae I-XIj, $R^5$ is $CF_3$.

In one embodiment, with respect to formulae I-XIj, $R^5$ is F.

In one embodiment, with respect to formulae I-XIj, $R^5$ is Cl.

In one embodiment, with respect to formulae I-XIj, $R^5$ is cyclopropyl.

In one embodiment, with respect to formulae I-XIj, $R^5$ is substituted cyclopropyl.

In one embodiment, with respect to formulae Ia-Ib, the compound is selected from compounds exemplified in Table 1.

In one embodiment, with respect to formulae Ia-Ib, the compound is other than:

N-[6-Chloro-2-(2-hydroxy-ethyl)-1-oxo-1,2-dihydro-iso-quinolin-5-yl]-2-(3,4-dichloro-phenyl)-acetamide;

(R)-2-[5-(2-Adamantan-1-yl-acetylamino)-6-chloro-1-oxo-1H-isoquinolin-2-yl]-propionamide;

(R)-2-{6-Chloro-1-oxo-5-[2-(4-trifluoromethyl-phenyl)-acetylamino]-1H-isoquinolin-2-yl}-propionamide;

(R)-2-{6-Chloro-5-[(S)-2-(4-chloro-phenyl)-propiony-lamino]-1-oxo-1H-isoquinolin-2-yl}-propionamide;

(R)-2-{6-Chloro-5-[2-(2-fluoro-3-trifluoromethyl-phenyl)-acetylamino]-1-oxo-1H-isoquinolin-2-yl}-propionamide;

(R)-2-{6-Chloro-5-[2-(4-chloro-2-fluoro-phenyl)-acety-lamino]-1-oxo-1H-isoquinolin-2-yl}-propionamide (R)-2-{6-Methoxy-1-oxo-5-[2-(4-trifluoromethyl-phenyl)-acetylamino]-1H-isoquinolin-2-yl}-propionamide;

(S)-2-{6-Chloro-1-oxo-5-[2-(4-trifluoromethyl-phenyl)-acetylamino]-1H-isoquinolin-2-yl}-propionamide 2-(3-Fluoro-4-trifluoromethyl-phenyl)-N-[2-((R)-2-hy-droxy-1-methyl-ethyl)-6-methoxy-1-oxo-1,2-dihydro-isoquinolin-5-yl]-acetamide;

N-[6-Chloro-2-((R)-2-hydroxy-1-methyl-ethyl)-1-oxo-1,2-dihydro-isoquinolin-5-yl]-2-(4-trifluoromethyl-phenyl)-acetamide;

N-[6-Chloro-2-((R)-2-hydroxy-1-methyl-ethyl)-1-oxo-1,2-dihydro-isoquinolin-5-yl]-2-(3-fluoro-4-trifluoromethyl-phenyl)-acetamide;

N-[6-Chloro-2-((R)-2-hydroxy-1-methyl-ethyl)-1-oxo-1,2-dihydro-isoquinolin-5-yl]-2-(3,4-dichloro-phenyl)-aceta-mide;

N-[6-Chloro-2-((R)-2-hydroxy-1-methyl-ethyl)-1-oxo-1,2-dihydro-isoquinolin-5-yl]-2-(4-fluoro-3-trifluoromethyl-phenyl)-acetamide;

N-[6-Chloro-2-((R)-2-hydroxy-1-methyl-ethyl)-1-oxo-1,2-dihydro-isoquinolin-5-yl]-2-(2-fluoro-4-trifluoromethyl-phenyl)-acetamide;

2-(4-Chloro-3-fluoro-phenyl)-N-[6-chloro-2-((R)-2-hy-droxy-1-methyl-ethyl)-1-oxo-1,2-dihydro-isoquinolin-5-yl]-acetamide;

N-[6-Chloro-2-(2-hydroxy-ethyl)-1-oxo-1,2-dihydro-iso-quinolin-5-yl]-2-(3-fluoro-4-trifluoromethyl-phenyl)-ac-etamide;

N-[6-Cyclopropyl-2-((R)-2-hydroxy-1-methyl-ethyl)-1-oxo-1,2-dihydro-isoquinolin-5-yl]-2-(3-fluoro-4-trifluo-romethyl-phenyl)-acetamide;

2-(2-Fluoro-3-trifluoromethyl-phenyl)-N-[2-(2-hydroxy-ethyl)-6-(2-hydroxy-ethylamino)-1-oxo-1,2-dihydro-iso-quinolin-5-yl]-acetamide;

N-[6-Chloro-2-(2-hydroxy-ethyl)-1-oxo-1,2-dihydro-iso-quinolin-5-yl]-2-(4-fluoro-3-trifluoromethyl-phenyl)-ac-etamide;

N-[6-Chloro-2-(2-hydroxy-ethyl)-1-oxo-1,2-dihydro-iso-quinolin-5-yl]-2-(2-fluoro-3-trifluoromethyl-phenyl)-ac-etamide;

2-(3-Fluoro-4-trifluoromethyl-phenyl)-N-[2-((R)-2-hydroxy-1-methyl-ethyl)-6-methyl-1-oxo-1,2-dihydro-isoquinolin-5-yl]-acetamide;
2-(4-Fluoro-3-trifluoromethyl-phenyl)-N-[2-((R)-2-hydroxy-1-methyl-ethyl)-6-methyl-1-oxo-2-dihydro-isoquinolin-5-yl]-acetamide;
2-(2-Fluoro-3-trifluoromethyl-phenyl)-N-[2-((R)-2-hydroxy-1-methyl-ethyl)-6-methyl-1-oxo-1,2-dihydro-isoquinolin-5-yl]-acetamide;
2-(2-Fluoro-3-trifluoromethyl-phenyl)-N-[2-(2-hydroxy-ethyl)-6-methyl-1-oxo-1,2-dihydro-isoquinolin-5-yl]-acetamide;
N-[2-((R)-2-Hydroxy-1-methyl-ethyl)-6-methyl-1-oxo-1,2-dihydro-isoquinolin-5-yl]-2-(4-trifluoromethyl-phenyl)-acetamide;
2-(4-Chloro-3-fluoro-phenyl)-N-[2-((R)-2-hydroxy-1-methyl-ethyl)-6-methyl-1-oxo-1,2-dihydro-isoquinolin-5-yl]-acetamide;
2-(4-Fluoro-3-trifluoromethyl-phenyl)-N-[2-(2-hydroxy-ethyl)-6-methyl-1-oxo-1,2-dihydro-isoquinolin-5-yl]-acetamide;
2-(3-Fluoro-4-trifluoromethyl-phenyl)-N-[2-(2-hydroxy-ethyl)-6-methyl-1-oxo-1,2-dihydro-isoquinolin-5-yl]-acetamide;
2-(3-Fluoro-4-trifluoromethyl-phenyl)-N-((S)-6-methyl-1-oxo-2-pyrrolidin-3-yl-1,2-dihydro-isoquinolin-5-yl)-acetamide; or
2-(4-Fluoro-3-trifluoromethyl-phenyl)-N-((S)-6-methyl-1-oxo-2-pyrrolidin-3-yl-1,2-dihydro-isoquinolin-5-yl)-acetamide.

In one embodiment, with respect to formulae Ia-Ib, the compound is selected from:
N-[6-Chloro-2-(2-hydroxy-ethyl)-1-oxo-1,2-dihydro-isoquinolin-5-yl]-2-(3,4-dichloro-phenyl)-acetamide;
(R)-2-[5-(2-Adamantan-1-yl-acetylamino)-6-chloro-1-oxo-1H-isoquinolin-2-yl]-propionamide;
(R)-2-{6-Chloro-1-oxo-5-[2-(4-trifluoromethyl-phenyl)-acetylamino]-1H-isoquinolin-2-yl}-propionamide;
(R)-2-{6-Chloro-5-[(S)-2-(4-chloro-phenyl)-propionylamino]-1-oxo-1H-isoquinolin-2-yl}-propionamide;
(R)-2-{6-Chloro-5-[2-(2-fluoro-3-trifluoromethyl-phenyl)-acetylamino]-1-oxo-1H-isoquinolin-2-yl}-propionamide;
(R)-2-{6-Chloro-5-[2-(4-chloro-2-fluoro-phenyl)-acetylamino]-1-oxo-1H-isoquinolin-2-yl}-propionamide;
(R)-2-{6-Methoxy-1-oxo-5-[2-(4-trifluoromethyl-phenyl)-acetylamino]-1H-isoquinolin-2-yl}-propionamide;
(S)-2-{6-Chloro-1-oxo-5-[2-(4-trifluoromethyl-phenyl)-acetylamino]-1H-isoquinolin-2-yl}-propionamide
2-(3-Fluoro-4-trifluoromethyl-phenyl)-N-[2-((R)-2-hydroxy-1-methyl-ethyl)-6-methoxy-1-oxo-1,2-dihydro-isoquinolin-5-yl]-acetamide;
N-[6-Chloro-2-((R)-2-hydroxy-1-methyl-ethyl)-1-oxo-1,2-dihydro-isoquinolin-5-yl]-2-(4-trifluoromethyl-phenyl)-acetamide;
N-[6-Chloro-2-((R)-2-hydroxy-1-methyl-ethyl)-1-oxo-1,2-dihydro-isoquinolin-5-yl]-2-(3-fluoro-4-trifluoromethyl-phenyl)-acetamide;
N-[6-Chloro-2-((R)-2-hydroxy-1-methyl-ethyl)-1-oxo-1,2-dihydro-isoquinolin-5-yl]-2-(3,4-dichloro-phenyl)-acetamide;
N-[6-Chloro-2-((R)-2-hydroxy-1-methyl-ethyl)-1-oxo-1,2-dihydro-isoquinolin-5-yl]-2-(4-fluoro-3-trifluoromethyl-phenyl)-acetamide;
N-[6-Chloro-2-((R)-2-hydroxy-1-methyl-ethyl)-1-oxo-1,2-dihydro-isoquinolin-5-yl]-2-(2-fluoro-4-trifluoromethyl-phenyl)-acetamide;
2-(4-Chloro-3-fluoro-phenyl)-N-[6-chloro-2-((R)-2-hydroxy-1-methyl-ethyl)-1-oxo-1,2-dihydro-isoquinolin-5-yl]-acetamide;
N-[6-Chloro-2-(2-hydroxy-ethyl)-1-oxo-1,2-dihydro-isoquinolin-5-yl]-2-(3-fluoro-4-trifluoromethyl-phenyl)-acetamide;
N-[6-Cyclopropyl-2-((R)-2-hydroxy-1-methyl-ethyl)-1-oxo-1,2-dihydro-isoquinolin-5-yl]-2-(3-fluoro-4-trifluoromethyl-phenyl)-acetamide;
2-(2-Fluoro-3-trifluoromethyl-phenyl)-N-[2-(2-hydroxy-ethyl)-6-(2-hydroxy-ethylamino)-1-oxo-1,2-dihydro-isoquinolin-5-yl]-acetamide;
N-[6-Chloro-2-(2-hydroxy-ethyl)-1-oxo-1,2-dihydro-isoquinolin-5-yl]-2-(4-fluoro-3-trifluoromethyl-phenyl)-acetamide;
N-[6-Chloro-2-(2-hydroxy-ethyl)-1-oxo-1,2-dihydro-isoquinolin-5-yl]-2-(2-fluoro-3-trifluoromethyl-phenyl)-acetamide;
2-(3-Fluoro-4-trifluoromethyl-phenyl)-N-[2-((R)-2-hydroxy-1-methyl-ethyl)-6-methyl-1-oxo-1,2-dihydro-isoquinolin-5-yl]-acetamide;
2-(4-Fluoro-3-trifluoromethyl-phenyl)-N-[2-((R)-2-hydroxy-1-methyl-ethyl)-6-methyl-1-oxo-1,2-dihydro-isoquinolin-5-yl]-acetamide;
2-(2-Fluoro-3-trifluoromethyl-phenyl)-N-[2-((R)-2-hydroxy-1-methyl-ethyl)-6-methyl-1-oxo-1,2-dihydro-isoquinolin-5-yl]-acetamide;
2-(2-Fluoro-3-trifluoromethyl-phenyl)-N-[2-(2-hydroxy-ethyl)-6-methyl-1-oxo-1,2-dihydro-isoquinolin-5-yl]-acetamide;
N-[2-((R)-2-Hydroxy-1-methyl-ethyl)-6-methyl-1-oxo-1,2-dihydro-isoquinolin-5-yl]-2-(4-trifluoromethyl-phenyl)-acetamide;
2-(4-Chloro-3-fluoro-phenyl)-N-[2-((R)-2-hydroxy-1-methyl-ethyl)-6-methyl-1-oxo-1,2-dihydro-isoquinolin-5-yl]-acetamide;
2-(4-Fluoro-3-trifluoromethyl-phenyl)-N-[2-(2-hydroxy-ethyl)-6-methyl-1-oxo-1,2-dihydro-isoquinolin-5-yl]-acetamide;
2-(3-Fluoro-4-trifluoromethyl-phenyl)-N-[2-(2-hydroxy-ethyl)-6-methyl-1-oxo-1,2-dihydro-isoquinolin-5-yl]-acetamide;
2-(3-Fluoro-4-trifluoromethyl-phenyl)-N-((S)-6-methyl-1-oxo-2-pyrrolidin-3-yl-1,2-dihydro-isoquinolin-5-yl)-acetamide; and
2-(4-Fluoro-3-trifluoromethyl-phenyl)-N-((S)-6-methyl-1-oxo-2-pyrrolidin-3-yl-1,2-dihydro-isoquinolin-5-yl)-acetamide.

In one embodiment, with respect to formulae Ia-Ib, the compound is selected from:
2-Adamantan-1-yl-N-[2-((R)-2-hydroxy-1-methyl-ethyl)-6-methyl-1-oxo-1,2-dihydro-isoquinolin-5-yl]-acetamide;
2-Cycloheptyl-N-[2-((R)-2-hydroxy-1-methyl-ethyl)-6-methyl-1-oxo-1,2-dihydro-isoquinolin-5-yl]-acetamide;
2-(3-Fluoro-4-trifluoromethyl-phenyl)-N-[2-((S)-2-hydroxy-1-methyl-ethyl)-6-methyl-1-oxo-dihydro-isoquinolin-5-yl]-acetamide;
N-[6-Chloro-2-((S)-2-hydroxy-1-methyl-ethyl)-1-oxo-1,2-dihydro-isoquinolin-5-yl]-2-(3-fluoro-4-trifluoromethyl-phenyl)-acetamide;
N-[2-((R)-2-Hydroxy-1-methyl-ethyl)-6-methyl-1-oxo-1,2-dihydro-isoquinolin-5-yl]-2-(3-trifluoromethyl-phenyl)-acetamide;
N-[6-Chloro-2-((R)-2-hydroxy-1-methyl-ethyl)-1-oxo-1,2-dihydro-isoquinolin-5-yl]-2-cycloheptyl-acetamide;

2-(1-Hydroxy-cycloheptyl)-N-[2-((R)-2-hydroxy-1-methyl-ethyl)-6-methyl-1-oxo-1,2-dihydro-isoquinolin-5-yl]-acetamide;

2-(3-Fluoro-4-trifluoromethyl-phenyl)-N-[6-methyl-2-(2-methylamino-ethyl)-oxo-1,2-dihydro-isoquinolin-5-yl]-acetamide;

N-[6-Chloro-2-((R)-2-hydroxy-1-methyl-ethyl)-1-oxo-1,2-dihydro-isoquinolin-5-yl]-2-(3-trifluoromethyl-phenyl)-acetamide;

2-((R)-2-Hydroxy-1-methyl-ethyl)-6-methyl-1-oxo-1,2-dihydro-isoquinoline-5-carboxylic acid 3-fluoro-4-trifluoromethyl-benzylamide;

6-Chloro-2-((R)-2-hydroxy-1-methyl-ethyl)-1-oxo-1,2-dihydro-isoquinoline-5-carboxylic acid 3-fluoro-4-trifluoromethyl-benzylamide;

2-((R)-2-Hydroxy-1-methyl-ethyl)-6-methyl-1-oxo-1,2-dihydro-isoquinoline-5-carboxylic acid 3-trifluoromethyl-benzylamide;

6-Chloro-2-((R)-2-hydroxy-1-methyl-ethyl)-1-oxo-1,2-dihydro-isoquinoline-5-carboxylic acid (6-trifluoromethyl-pyridin-3-ylmethyl)-amide;

6-Chloro-2-((R)-2-hydroxy-1-methyl-ethyl)-1-oxo-1,2-dihydro-isoquinoline-5-carboxylic acid 3-trifluoromethyl-benzylamide;

6-Chloro-2-((R)-2-hydroxy-1-methyl-ethyl)-1-oxo-1,2-dihydro-isoquinoline-5-carboxylic acid 4-chloro-3-fluoro-benzylamide;

6-Chloro-2-((R)-2-hydroxy-1-methyl-ethyl)-1-oxo-1,2-dihydro-isoquinoline-5-carboxylic acid 2-trifluoromethyl-benzylamide;

6-Chloro-2-((R)-2-hydroxy-1-methyl-ethyl)-1-oxo-1,2-dihydro-isoquinoline-5-carboxylic acid (1-hydroxy-cycloheptylmethyl)-amide;

6-Chloro-2-((R)-2-hydroxy-1-methyl-ethyl)-1-oxo-1,2-dihydro-isoquinoline-5-carboxylic acid cycloheptylmethyl-amide;

2-((R)-2-Hydroxy-1-methyl-ethyl)-6-methyl-1-oxo-1,2-dihydro-isoquinoline-5-carboxylic acid cycloheptylmethyl-amide;

2-((R)-2-Hydroxy-1-methyl-ethyl)-6-methyl-1-oxo-1,2-dihydro-isoquinoline-5-carboxylic acid 4-chloro-3-fluoro-benzylamide;

(R)-2-{5-[2-(3-Fluoro-4-trifluoromethyl-phenyl)-acetylamino]-6-methyl-1-oxo-1H-isoquinolin-2-yl}-propionamide;

2-((R)-2-Hydroxy-1-methyl-ethyl)-6-methyl-1-oxo-1,2-dihydro-isoquinoline-5-carboxylic acid (1-hydroxy-cycloheptylmethyl)-amide;

6-Chloro-2-((R)-2-hydroxy-1-methyl-ethyl)-1-oxo-1,2-dihydro-isoquinoline-5-carboxylic acid(2-hydroxy-bicyclo[2.2.1]hept-2-ylmethyl)-amide;

6-Chloro-2-((R)-2-hydroxy-1-methyl-ethyl)-1-oxo-1,2-dihydro-isoquinoline-5-carboxylic acid(1-hydroxy-4,4-dimethyl-cyclohexylmethyl)-amide;

6-Chloro-2-((R)-2-hydroxy-1-methyl-ethyl)-1-oxo-1,2-dihydro-isoquinoline-5-carboxylic acid(1-hydroxy-3,3-dimethyl-cyclohexylmethyl)-amide;

6-Chloro-2-((R)-2-hydroxy-1-methyl-ethyl)-1-oxo-1,2-dihydro-isoquinoline-5-carboxylic acid (1-hydroxy-4-trifluoromethyl-cyclohexylmethyl)-amide;

6-Chloro-2-((R)-2-hydroxy-1-methyl-ethyl)-1-oxo-1,2-dihydro-isoquinoline-5-carboxylic acid (1-hydroxy-cyclohexylmethyl)-amide;

N-[2-((R)-2-Amino-1-methyl-ethyl)-6-methyl-1-oxo-1,2-dihydro-isoquinolin-5-yl]-2-(3-fluoro-4-trifluoromethyl-phenyl)-acetamide;

2-(3-Fluoro-4-trifluoromethyl-phenyl)-N-[6-methyl-2-((R)-1-methyl-2-methylamino-ethyl)-1-oxo-1,2-dihydro-isoquinolin-5-yl]-acetamide;

2-(3-Fluoro-4-trifluoromethyl-phenyl)-N-[6-methyl-2-((R)-1-methyl-2-piperazin-1-yl-ethyl)-1-oxo-1,2-dihydro-isoquinolin-5-yl]-acetamide;

6-Chloro-2-((R)-2-hydroxy-1-methyl-ethyl)-1-oxo-1,2-dihydro-isoquinoline-5-carboxylic acid(4,4-difluoro-cyclohexylmethyl)-amide;

2-(3-Fluoro-4-trifluoromethyl-phenyl)-N-[2-(2-hydroxy-1-hydroxymethyl-ethyl)-6-methyl-1-oxo-1,2-dihydro-isoquinolin-5-yl]-acetamide;

6-Chloro-2-((R)-2-hydroxy-1-methyl-ethyl)-1-oxo-1,2-dihydro-isoquinoline-5-carboxylic acid(6-hydroxy-spiro[2.5]oct-6-ylmethyl)-amide; and 2-(3-Fluoro-4-trifluoromethyl-phenyl)-N-{2-[(R)-2-(3-hydroxy-azetidin-1-yl)-1-methyl-ethyl]-6-methyl-1-oxo-1,2-dihydro-isoquinolin-5-yl}-acetamide.

In one embodiment, with respect to formulae Ia-Ib, the compound is selected from

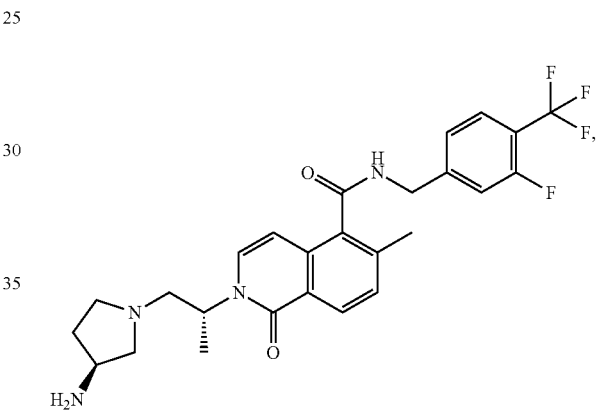

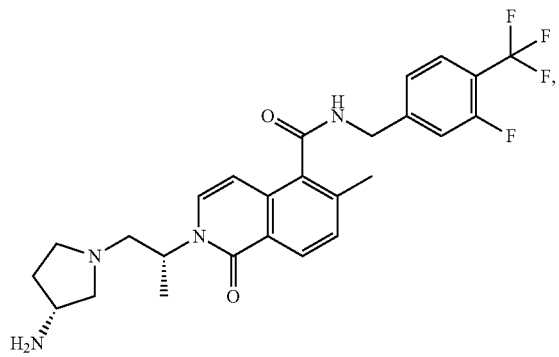

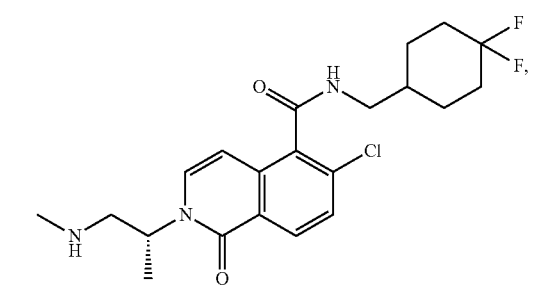

47
-continued
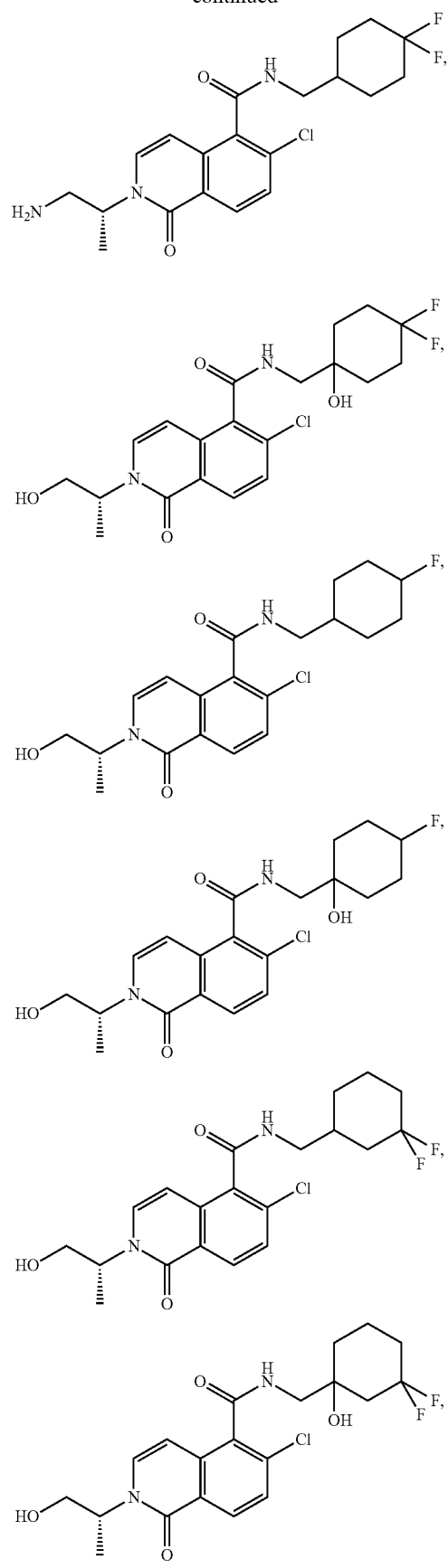
48
-continued
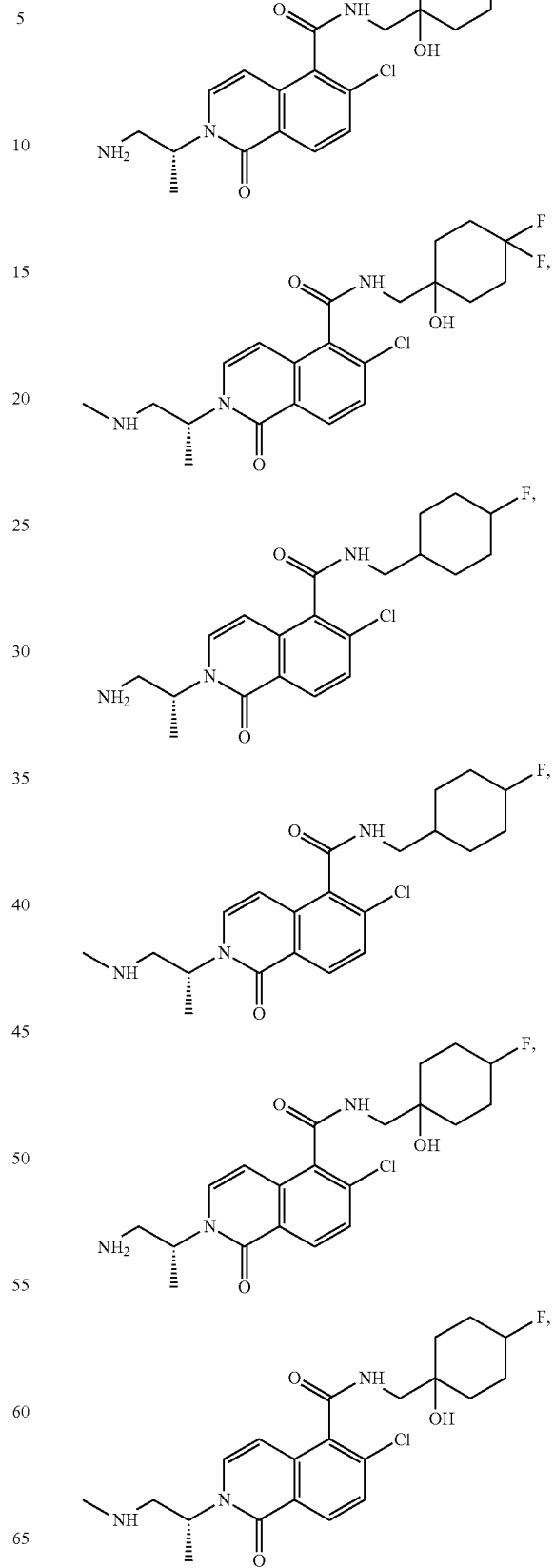

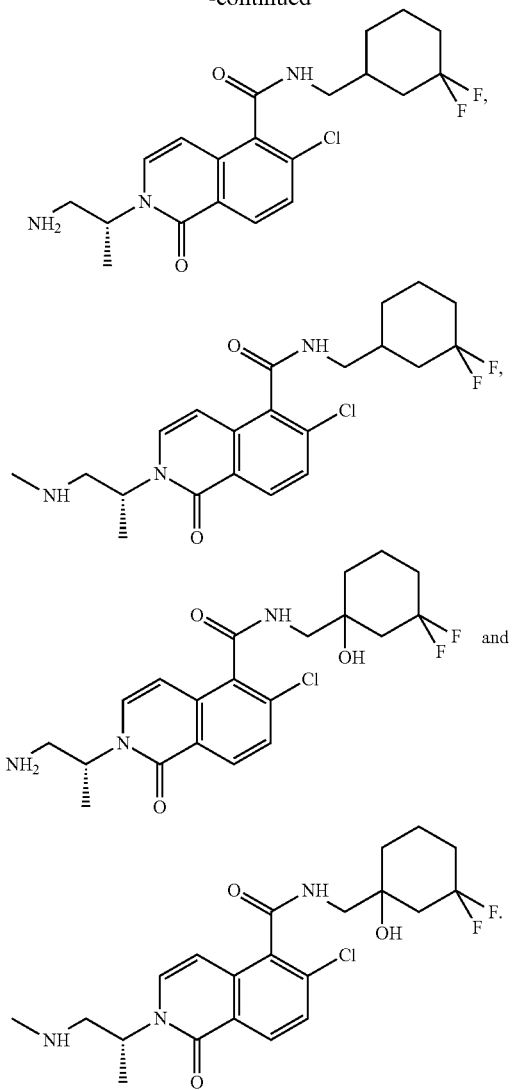

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's The Science and Practice of Pharmacy, 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences*.

The following formulation examples illustrate representative pharmaceutical compositions that may be prepared in accordance with this invention. The present invention, however, is not limited to the following pharmaceutical compositions.

Formulation 1

Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2

Capsules

A compound of the invention is admixed as a dry powder with a starch diluent in an approximate 1:1 weight ratio. The mixture is filled into 250 mg capsules (125 mg of active compound per capsule).

Formulation 3

Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then added to produce a total volume of 5 mL.

Formulation 4

Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5

Injection

A compound of the invention is dissolved or suspended in a buffered sterile saline injectable aqueous medium to a concentration of approximately 5 mg/mL.

Formulation 6

Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals that are causally related or attributable to aberrant activity of the $P2X_7$ receptor. Accordingly, the compounds and pharmaceutical compositions of this invention find use as therapeutics for preventing and/or treating autoimmune, inflammatory and cardiovascular conditions in mammals including humans. Thus, and as stated earlier, the present invention includes within its scope, and extends to, the recited methods of treatment, as well as to the compounds for such methods, and to the use of such compounds for the preparation of medicaments useful for such methods.

In a method of treatment aspect, this invention provides a method of treating a mammal susceptible to or afflicted with a condition associated with arthritis, uveitis, asthma, myocardial infarction, traumatic brain injury, acute spinal cord injury, inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. The present amines have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, multiple sclerosis; diseases and disorders which are mediated by or result in neuroinflammation such as, for example traumatic brain injury, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; obesity; lipid disorders; cancer; blood pressure; spinal cord injury; and renal disorders method comprises administering an effective condition-treating or condition-preventing amount of one or more of the pharmaceutical compositions just described.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity, and that are determined to safe and efficacious for such combined administration.

General Synethetic Procedures

The bicycloheteroaryl compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following representative methods are presented with details as to the preparation of representative bicycloheteroaryls that have been listed herein above. The compounds of the invention may be prepared from known or commercially available starting materials and reagents by one skilled in the art of organic synthesis.

Synthesis of Intermediates

Intermediate 1

(E)-Methyl 2-(2-(dimethylamino)-vinyl)-3-nitrobenzoate

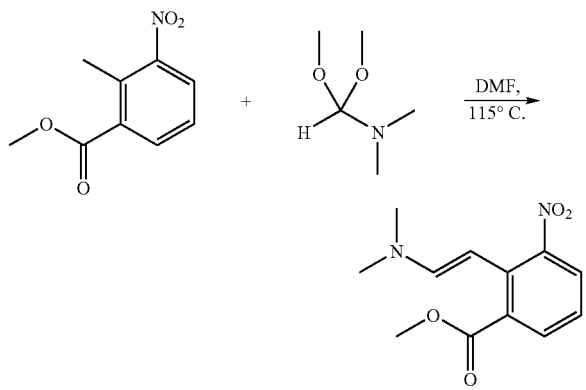

A mixture of methyl 2-methyl-3-nitrobenzoate (5.0 g, 25.6 mmol) and N,N-dimethylformamide dimethyl acetal (9.18 g, 77 mmol) in N,N-dimethylformamide (30 mL) was stirred at 115° C. for 17 h. The volatiles were removed under reduced pressure to give (E)-methyl 2-(2-(dimethylamino)-vinyl)-3-nitrobenzoate as a brown oil.

¹H-NMR (300 MHz, CDCl₃) δ 7.68 (m, 2H), 7.07 (t, J=7.5 Hz 1H), 6.32 (d, J=13.5 Hz, 1H), 5.65 (d, J=13.5 Hz, 1H), 3.85 (s, 3H), 2.82 (s, 6H).

Intermediate 2

5-Nitro-1H-isochromen-1-one

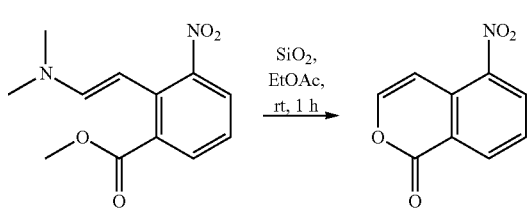

(E)-Methyl 2-(2-(dimethylamino) vinyl)-3-nitrobenzoate was dissolved in ethyl acetate (200 mL), and silica gel (200 g) was added. The resulting suspension was stirred at room temperature for 1 h. The ethyl acetate solution was filtered off. Silica gel was washed with ethyl acetate (2×150 mL) and the combined organics were evaporated and dried under reduced pressure to yield 5-nitro-1H-isochromen-1-one (4.0 g, 21.0 mmol, 82% after two steps) as a brown solid.

MS m/z=192.1 (M+H)⁺.

¹H-NMR (300 MHz, CDCl₃) δ 8.62 (d, J=7.8 Hz, 1H), 8.47 (d, J=8.1 Hz, 1H), 7.65 (m, 1H), 7.42 (d, J=6.3 Hz, 1H), 7.36 (d, J=6.3 Hz, 1H).

Additional information can be found in McDonald, M. C. et al. British J. Pharmacol. 2000, 130, 843, incorporated herein by reference.

Intermediate 3

5-Amino-1H-isochromen-1-one

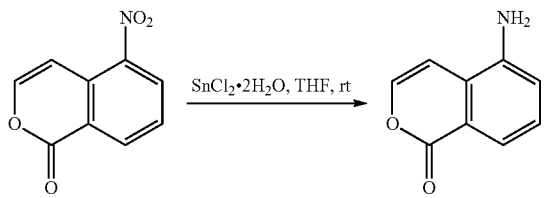

Tin(II)chloride dihydrate (41.9 g, 185.7 mmol) was added to a stirred solution of 5-nitro-1H-isochromen-1-one (7.1 g, 37.1 mmol) in anhydrous tetrahydrofuran (120 mL). The reaction mixture was stirred at room temperature for 18 h. The resulting mixture was diluted with ethyl acetate (400 mL) and treated with saturated aqueous sodium bicarbonate to pH=10. Water (100 mL) was added and the layers were separated. The aqueous phase was extracted with ethyl acetate (2×150 mL) and the combined organic fractions were dried over sodium sulfate, filtered and evaporated to yield 5-amino-1H-isochromen-1-one (5.8 g, 36.0 mmol, 97%) as a yellow solid.

MS m/z=162.3 (M+H)⁺.

¹H-NMR (300 MHz, CD₃OD) δ 7.52 (d, J=7.8 Hz, 1H), 7.32 (d, J=5.7 Hz, 1H), 7.27 (t, J=7.8 Hz, 1H), 7.07 (d, J=7.8 Hz, 1H), 6.80 (d, J=5.7 Hz, 1H).

Additional information can be found in Lee, B. S.; et al. *J. Org. Chem.* 2004, 69, 3319 incorporated herein by reference.

Intermediate 4

6-Methyl-5-nitro-1H-isochromen-1-one

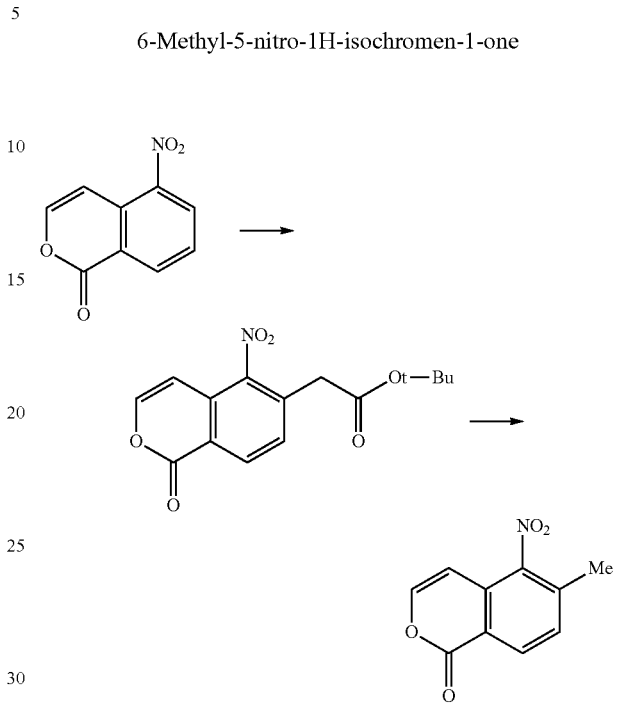

a. (E)-tert-Butyl 2-(5-nitro-1-oxo-1H-isochromen-6-yl)acetate

A round bottom flask was charged with potassium tert-butoxide (4.4 g, 0.039 mol) and N,N-dimethylformamide (30 mL, 0.4 mol) and a solution of acetic acid, chloro-, 1,1-dimethylethyl ester (2.5 mL, 0.017 mol) and 5-nitro-isochromen-1-one (3.00 g, 0.0157 mol) in N,N-dimethylformamide (5 mL, 0.06 mol) was added at −20° C. slowly over a period of 40 minutes and the reaction was stirred for another 45 minutes at the same temperature. The reaction mixture was poured into 4 ml of hydrochloric acid and 80 mL of water and extracted with dichloromethane and washed with brine and dried over sodium sulfate. the solvent was removed under reduced pressureunder reduced pressure and the residue purified by flash chromatography to afford the product as light thick oil.

MS m/z=306.4 (M+H).

b. 6-Methyl-5-nitro-1H-isochromen-1-one

A microwave vial was charged with tert-butyl 2-(5-nitro-1-oxo-1H-isochromen-6-yl)acetate (800.0 mg, 0.002620 mol), trifluoroacetic acid (2 mL, 0.02 mol). The mixture was subjected to microwave at 100° C. for 20 minutes. Trifluoroacetic acid was removed under reduced pressure and the residue was taken in a microwave tube and quinoline (2 mL, 0.02 mol) was added and was heated at 120° C. for 20 minutes. Ethyl acetate (50 mL) was added and washed with 10 mL of 6N hydrochloric acid. The hydrochloric acid layer was extracted with ethyl acetate (50 mL) and the combined organic layers were washed with water, brine and dried. the solvent was removed under reduced pressureunder reduced pressure and the brown solid residue was purified by flash chromatography to yield the pure product as a white solid.

MS m/z=206.4 (M+H)

$^1$H-NMR (400 MHz, DMSO-$d_6$) δ 8.29 (d, J=8.19 Hz, 1H), 7.71-7.69 (m, 2H), 6.57 (d, J=6.02 Hz, 1H), 2.45 (s, 3H).

Alternatively, to a solution of potassium tert-butoxide (8.72 g, 0.0777 mol) in N,N-dimethylformamide (250 mL, 3.2 mol) was added a mixture of acetic acid, chloro-, 1,1-dimethylethyl ester (4.335 g, 0.02878 mol) and 5-nitro-1H-isochromen-1-one (5.0 g, 0.026 mol) in N,N-dimethylformamide (50 mL, 0.6 mol) at −20° C. After 1 h, the reaction was poured onto hydrochloric acid (16 mL) and water (35 mL). The aqueous solution was extracted with dichloromethane, washed with brine, dried over magnesium sulfate, and concentrated under reduced pressure. The residue was treated with trifluoroacetic acid (35 mL, 0.45 mol) for 0.5 h and was removed under reduced pressure. The residue was stirred with potassium carbonate (6.98 g, 0.0505 mol) in N,N-dimethylformamide (200 mL, 2 mol) at 50° C. for 1 h. The reaction was cooled and added with 1 N hydrochloric acid (262 mL), extracted with dichloromethane (80 mL×3), washed with brine and dried over magnesium sulfate. The solvents were removed under reduced pressure and the mixture was purified by flash chromatography to afford the title compound as a yellow solid.

Intermediate 5

6-Cyclopropyl-5-nitro-1H-isochromen-1-one

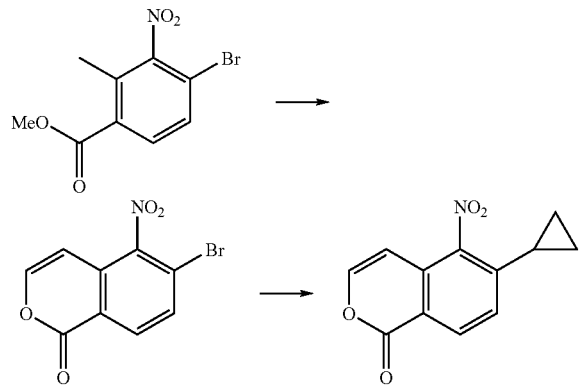

a. 6-Bromo-5-nitro-1H-isochromen-1-one

A pressure tube (150 mL) was charged with methyl 4-bromo-2-methyl-3-nitrobenzoate (2.1 g, 0.0077 mol), 1,1-dimethoxy-N,N-dimethylmethanamine (3.6 mL, 0.027 mol) and N,N-dimethylformamide (5 mL, 0.06 mol). The mixture was heated at 120° C. for 20 hours the solvent was removed under reduced pressure and the residue was dissolved in ethyl acetate (100 mL, 1 mol). Silica Gel (20 g, 0.3 mol) was then added and the reaction was stirred at room temperature for 12 h. The reaction was filtered and the solvent was removed and the residue was purified by flash chromatography to afford the desired product. MS m/z=271.2 (M+H).

b. 6-Cyclopropyl-5-nitro-1H-isochromen-1-one

A microwave vial was charged with 6-bromo-5-nitro-1H-isochromen-1-one (500.00 mg, 0.0018516 mol), cyclopropylboronic acid (206.8 mg, 0.002407 mol), palladium acetate (21 mg, 0.000092 mol), tricyclohexylphosphine (52 mg, 0.00018 mol), potassium phosphate (1376 mg, 0.006481 mol), toluene (10 mL, 0.09 mol) and water. The mixture was heated using microwave irradiation at 100° C. for 30 minutes. The rection mixture was then diluted with water and extracted with ethyl acetate. The combined organic layers were washed with brine, dried and evaporated. The resultant residue was purified by flash chromatography to afford the product. The product was used as such for the syntheses of 6-cyclopropyl compounds of this invention without further purification.

MS m/z=232.3 (M+H).

$^1$H NMR (400 MHz, DMSO-$d_6$) δ 8.22 (d, J=8.63 Hz, 1H), 7.69 (d, J=5.85 Hz, 1H), 7.33 (d, J=8.47 Hz, 1H), 6.51 (d, J=6.05 Hz, 1H), 1.96-1.89 (m, 1H), 1.19-1.14 (m, 2H) 0.97-0.93 (m, 2H).

Intermediate 6

6-Chloro-5-nitro-1H-isochromen-1-one

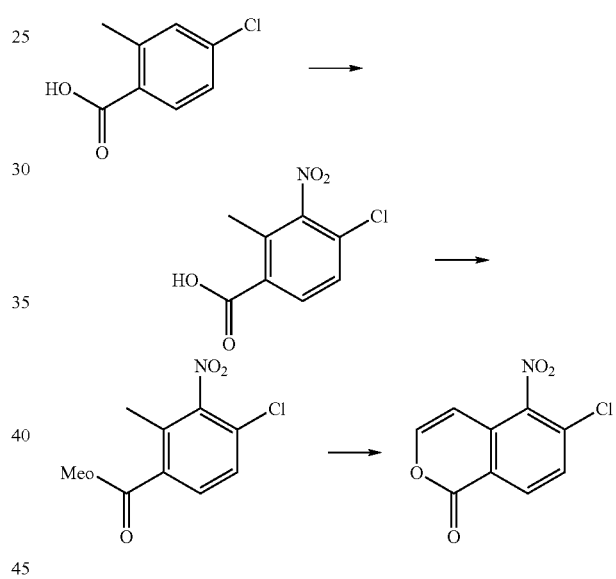

a. 4-Chloro-2-methyl-3-nitrobenzoic acid

A round bottom flask was charged with 4-chloro-2-methylbenzoic acid (200 mg, 0.001 mol) and sulfuric acid (1 mL, 0.02 mol). Fuming nitric acid (0.05 mL, 0.001 mol) was added at −20° C. and the reaction was stirred for 1 hour at 70° C. and poured into ice cold water, whereupon the mixture of 2- and 4-nitro compounds precipitated out. The precipitate was filtered and dissolved in ethyl acetate (30 mL) and washed with saturated aqueous sodium bicarbonate solution and brine, and dried over sodium sulfate. The solvent was reduced to ¼ volume whereby the undesired isomer precipitated out. The precipitate was filtered and the filtrate was dried to afford a 1:1 mixture of isomers as a white solid.

MS m/z=214.5 (M−H).

b. Methyl 4-chloro-2-methyl-3-nitrobenzoate

A round bottom flask was charged with 4-chloro-2-methyl-3-nitrobenzoic acid (11.00 g, 0.05102 mol), and methanol (110 mL, 2.7 mol). Thionyl chloride (4.5 mL, 0.061 mol) was added at 0° C. and the reaction was heated at 75° C. for 3 hours. the solvent was removed under reduced pressureunder reduced pressure and the residue was dissolved in ethyl acetate (300 mL) and washed with aqueous sodium bicarbonate, water and brine. The organic extracts were combined and dried over sodium sulfate and the solvent was removed to afford the corresponding esters.

MS m/z=230.3 (M+H).

c. 6-Chloro-5-nitro-1H-isochromen-1-one

A pressure tube was charged with methyl 4-chloro-2-methyl-3-nitrobenzoate (13 g, 57 mmol), N,N-dimethylformamide (10 mL, 200 mmol) and 1,1-dimethoxy-N,N-dimethyl-methanamine (26.5 mL, 200 mmol). The reaction was heated at 120° C. for 20 h. The solvents were removed and the resultant brown residue was redissolved in ethyl acetate (600 mL, 6000 mmol) and 130-270 mesh 60A silica gel (500 g, 6000 mmol) was added. The reaction was stirred with a mechanical stirrer for 8 h. The reaction was filtered, washed with ethyl acetate (400 mL). the organics were combined. and the solvents were removed under reduced pressure. The residue was purified by flash chromatography to give the desired product.

MS m/z=226.2 (M+H).

$^1$H NMR (400 MHz; DMSO-d6) δ 8.35 (d, J=8.63 Hz, 1H), 7.95 (d, J=8.63Hz, 1H), 7.76 (d, J=5.91 Hz, 1H), 6.61 (d, J=6.04 Hz, 1H).

Intermediate 7

4,4-(Difluorocyclohexyl)methylamine hydrochloride

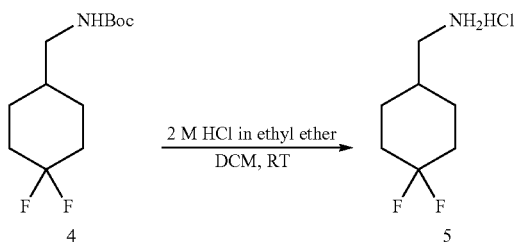

tert-Butyl (4,4-difluorocyclohexyl)methylcarbamate (0.43 g, 0.0016 mol) and 4M of hydrogen chloride in 1,4-dioxane (4 mL, 0.02 mol) were stirred at 0° C. for 1 h and then at room temperature overnight. The solvents were removed under vacuum, the residue was washed with ether, filtered and dried in air to afford the desired product as an off-white solid (292 mg, yield 91%).

$^1$H NMR (400 MHz, CD$_3$OD,) δ 2.86 (d, J=7.0 Hz, 2H), 2.13-2.06 (m, 2H), 1.88-1.72 (m, 5H), 1.39-1.28 (m, 2H).

Intermediate 8

1-(Aminomethyl)-4,4-dimethylcyclohexanol

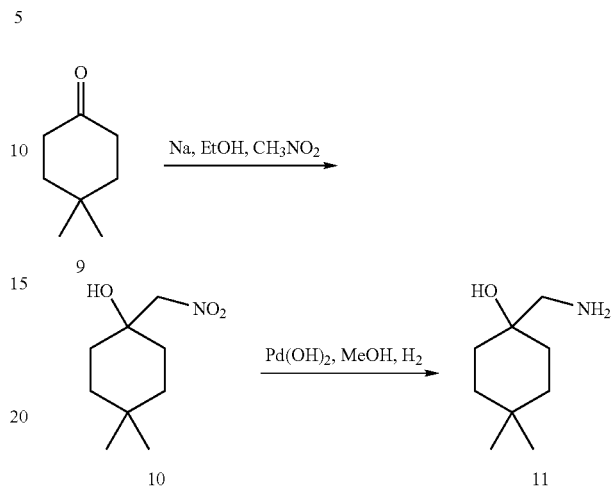

4,4-Dimethyl-1-(nitromethyl)cyclohexanol (10)

To a mixture of sodium (0.2 g, 0.009 mol) and ethanol (5 mL, 0.08 mol) was added a solution of nitromethane (0.77 g, 0.013 mol) and 4,4-dimethyl-cyclohexanone (1 g, 0.008 mol) in ethanol (1 mL) dropwise. The mixture was stirred at room temperature for 4 hours. Acetic acid (2 mL) and water (10 mL) were added and the mixture was concentrated under reduced pressure. The residue was dissolved in ethyl acetate (200 mL), washed with brine (30 mL×3), dried over sodium sulfate, and purified by flash chromatography to afford the desired product as a clear oil. (1.5 g, 90%).

$^1$H NMR (400 MHz, CDCl$_3$) δ 4.44 (s, 2H), 1.61-1.56 (m, 6H), 1.27-1.23 (m, 2H), 0.97 (s, 3H), 0.91 (s, 3H).

1-(Aminomethyl)-4,4-dimethylcyclohexanol (11)

A mixture of 4,4-dimethyl-1-(nitromethyl)cyclohexanol (1.5 g, 0.0072 mol) and palladium hydroxide (0.1 g, 0.0001 mol) in methanol (50 mL, 1 mol) was stirred under hydrogen (1 atm) at room temperature overnight. The mixture was filtered and concentrated to afford the desired product as a clear oil. (1.08 g, 95%).

$^1$H NMR (400 MHz, CDCl$_3$,) δ 3.49 (s, 2H), 1.56-1.36 (m, 6H), 1.22-1.20 (m, 2H), 0.95 (s, 3H), 0.88 (s, 3H)

Intermediate 9

6-(Aminomethyl)spiro[2.5]octan-6-ol hydrochloride

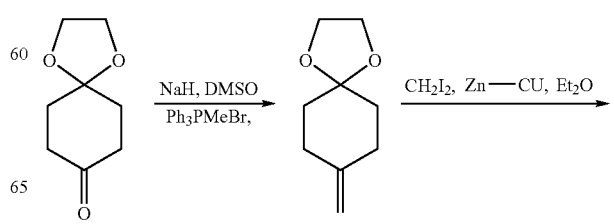

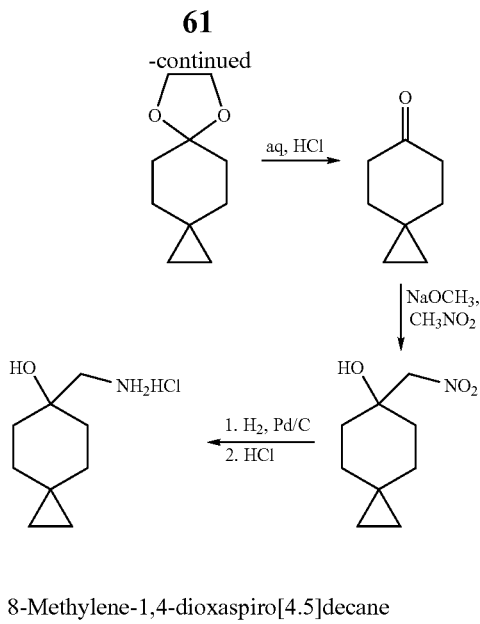

8-Methylene-1,4-dioxaspiro[4.5]decane 1,4-Dioxaspiro[4.5]decan-8-one (21 g, 0.13 mol) in dry benzene (50 mL, 0.6 mol) was added to ethylenetriphenylphosphorane [prepared from dimsyl sodium and methyltriphenylphosphonium bromide (106 g, 0.291 mol) in dimethyl sulfoxide (600 mL, 8 mol)] The mixture was stirred at room temperature overnight and poured into a separating funnel containing ethyl ether (500 mL) and water (500 mL). The organic layer was separated and the aqueous phase was extracted with ethyl ether (2×500 mL). The combined ether layers were washed with water (500 mL) and brine (500 mL), and dried. The solvents were removed under reduced pressure and the residue was purified by flash chromatography to afford the desired product (18.0 g, 85%).

Spiro[2.5]octan-6-one

A 250 mL round-bottom flask equipped with a reflux condenser was charged with zinc-copper couple (6.5 g, 0.05 mol) and ethyl ether (100 mL). Iodine (0.42 g, 0.00165 mol) was added and stirred until the brown color disappeared. Diiodomethane (26.56 g, 0.09915 mol) was added and heated at reflux for 2 h. 8-Methylene-1,4-dioxaspiro[4.5]decane (10 g, 0.06 mol), dissolved in ethyl ether (50 ml) was added and the mixture was heated at roflux overnight. An additional portion of diiodomethane (26.56 g, 0.09915 mol), zinc-copper couple (6.5 g, 0.05 mol) and iodine (0.42 g, 0.00165 mol) was added and the reaction was continued at reflux for overnight. The reaction mixture was cooled to room temperature, filtered, and the precipitate was rinsed with ethyl ether (100 mL). The combined ether solutions were placed in a 500 mL round-bottom flask and IN hydrochloric acid (200 mL) was added and stirred at room temperature for 1 hour. The layers were separated and the aqueous layer was extracted with ethyl ether (2×200 mL). The combined organic layers were dried and concentrated under educed pressure. The residue was purified by flash chromatography to afford the desired product. (4.6 g 50%).

6-(Nitromethyl)spiro[2.5]octan-6-ol

To 4M solution of sodium methoxide (14 mL) in methanol (10 mL) was added a solution of spiro[2.5]octan-6-one (4.6 g, 0.031 mol) and nitromethane (2.3 mL, 0.042 mol) in methanol (20 mL) at room temperature and stirred overnight. The reaction was quenched with acetic acid (4.5 mL) and water (50 mL) and the volatiles were removed under reduced pressure. The residue was extracted with dichloromethane (2×50 mL), and the combined extracts were dried, filtered and evaporated. The residue was purified by flash chromatography to afford the desired product (3.2 g, 52%).

6-(Aminomethyl)spiro[2.5]octan-6-ol hydrochloride 6-(Nitromethyl)spiro[2.5]octan-6-ol (1.5 g, 0.0077 mol) was dissolved in ethyl acetate (30 mL, 0.3 mol), and 10% palladium on carbon (2 g) was added. The mixture was stirred under hydrogen (40~50 psi) overnight. The mixture was filtered and the volatiles removed under reduced pressure. The residue was dissolved in dichloromethane (3 ml) and 2M hydrogen chloride in ether (6 mL) was added. The solid was filtered and rinsed with 10 mL of (dichloromethane:Et$_2$O=: 4), and dried to afford the desired amine as a white solid. (1.0 g, 60%).

$^1$H NMR (400 MHz, DMSO-d6) δ: 7.91 (br, 3H), 4.85 (s, 1H), 2.75 (br, 2H), 1.69-1.66 (m, 2H), 1.59-1.54 (m, 2H), 1.47-1.42 (m, 2H), 0.94-0.91 (m, 2H), 0.25-0.19 (m, 4H).

Intermediate 10

(General Synthetic Method for Preparation of the 5-Iodo Derivative)

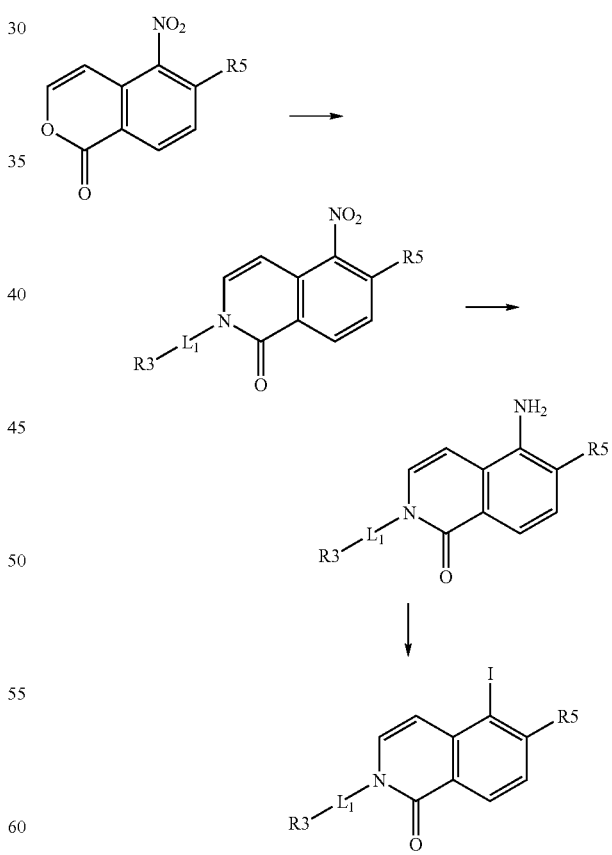

2-(-L1-R$^3$)-5-nitroisoquinolin-6-(R$^5$)-1(2H)-one

A 5-nitro-isochromen-1-one derivative (0.005 mol) and R$^3$-L$^1$-NH$_2$ (0.02 mol) were refluxed in methanol (20 mL, 0.5 mol) for 2 hours. The volatiles were removed under reduced pressure, and the residue was purified via flash chromatography to afford the nitro intermediate as a solid.

b. 5-Amino-2-(-L1-R³)-6-(R⁵)-isoquinolin-1(2H)-one

A round bottom flask was charged with the above mentioned 5-nitroisoquinolin-1(2H) one derivative (0.074 mol), ethanol (500mL, 8 mol), and the solution was heated at 85° C. Ammonium chloride (50 g, 0.9 mol) in water (150 mL, 8.3 mol) was added followed by iron (20 g, 0.3 mol) in two portions. The reaction was stirred for 1 hour and poured onto dichloromethane(200 mL) and extracted. the solvent was removed under reduced pressureunder reduced pressure to afford the desired product.

Alternatively, 5-nitroisoquinolin-1(2H)-one derivative (0.0022 mol) and tin dichloride dihydrate (2 g, 0.009 mol) were stirred in tetrahydrofuran (20 mL, 0.2 mol) at room temperature overnight. The volatiles were removed under reduced pressure and the residue was dissolved in methanol, poured over a pad of basic alumina and concentrated to afford the desired product.

c. 2-(-L1-R³)-6-(R⁵)-5-iodo-2H-isoquinolin-1-one

Amino isoquinolin-1(2H)-one derivative (0.002 mol) was added to a solution of sodium nitrite (0.5 g, 0.008 mol) in dimethyl sulfoxide (10 mL, 0.1 mol) at 35° C. followed by aqueous hydrogen iodide (2 mL, 0.02 mol) in dimethyl sulfoxide (10 mL, 0.1 mol). The reaction mixture was stirred at 35° C. for 1 hour, cooled to room temperature and was neutralized with saturated aqueous sodium carbonate. The mixture was extracted with methylene chloride (3×20 mL) and the combined extracts were washed with brine and dried. the solvent was removed under reduced pressureunder reduced pressure and the residue was purified by flash chromatography to afford the desired iodo intermediate.

Alternatively, to a solution of sodium nitrite (1 g, 0.02 mol), hexamethyldisilane (3 g, 0.02 mol), iodine (5 g, 0.02 mol) and benzyltriethylammonium chloride (0.3 g, 0.001 mol) in carbon tetrachloride (100 mL, 1 mol) was added a solution of amino isoquinolin-1(2H)-one derivative (0.0070 mol) in methylene chloride (3 mL, 0.05 mol) at 0° C. The mixture was stirred at the same temperature for 40 minutes and then warmed to room temperature overnight. The mixture was purified by flash chromatography to afford the desired iodo intermediate.

Intermediate 11

(R)-2-(5-amino-6-chloro-1-oxoisoquinolin-2(1H)-yl) propyl acetate

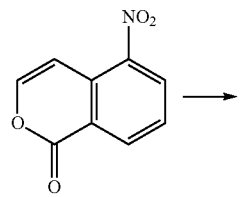

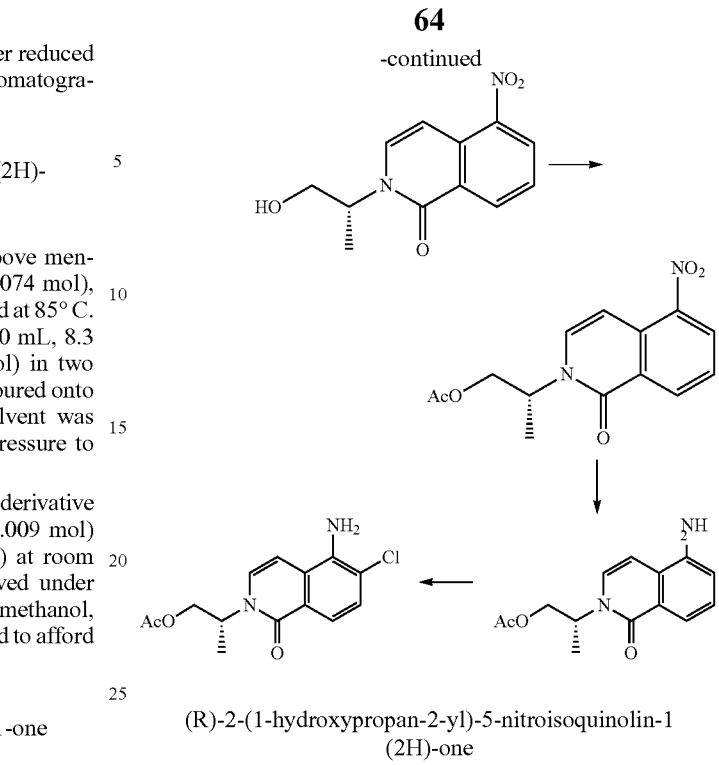

(R)-2-(1-hydroxypropan-2-yl)-5-nitroisoquinolin-1 (2H)-one

A 250 mL round bottom flask was charged with 5-nitro-isochromen-1-one (40 g, 0.2 mol), (2R)-2-Aminopropan-1-ol (18 g, 0.24 mol), triethylamine (100 mL, 0.7 mol) and methanol (500 mL, 10 mol) and the reaction heated at 88° C. for 1.5 hours. The product precipitated out upon cooling the reaction and was filtered to afford the product as a yellow solid. (17.3 g, 40% yield).

(R)-2-(5-nitro-1-oxoisoquinolin-2(1H)-yl)propyl acetate (R)-2-(1-hydroxypropan-2-yl)-5-nitroisoquinolin-1(2H)-one (19 g, 0.073 mol), acetic anhydride (10 g, 0.1 mol), triethylamine (30 g, 0.3 mol), 4,4-dimethylaminopyridine (200 mg, 0.002 mol) and methylene chloride (500 mL, 8 mol) were stirred at room temperature overnight. The solvents were removed under reduced pressure and the residue was purified flash chromatography to afford the title compound as a yellow oil (21 g, 100% yield).

(R)-2-(5-amino-1-oxoisoquinolin-2(1H)-yl)propyl acetate

A round bottom flask was charged with (R)-2-(5-nitro-1-oxoisoquinolin-2(1H)-yl)propyl acetate (24 g, 0.074 mol), ethanol (500 mL, 8 mol), and was heated at 85° C. Ammonium chloride (50 g, 0.9 mol) in water (150 mL, 8.3 mol) was added followed by iron (20 g, 0.3 mol) in two portions. The reaction was stirred for 1 hour and poured onto dichloromethane (200 mL) and extracted. the solvent was removed under reduced pressureunder reduced pressure to afford the desired product as red oil (19 g, 100%).

(R)-2-(5-amino-6-chloro-1-oxoisoquinolin-2(1H)-yl) propyl acetate

To a solution of acetic acid (R)-2-(5-amino-1-oxo-1H-iso-quinolin-2-yl)-propyl ester (20 g, 0.07 mol) in carbon tetrachloride (400 mL, 4 mol) at 60° C. was added a solution of N-chlorosuccinimide (11 g, 0.082 mol) in N,N-dimethylformamide (140 mL, 1.8 mol) in 50 minutes. The mixture was stirred at 60° C. for an additional 15 minutes. The cooled mixture was diluted with dichloromethane (400 mL), washed with sodium bicarbonate (100 mL×3), and concentrated under reduced pressure. The mixture was purified by flash chromatography to afford the desired product as a brown oil.

Intermediate 12

(R)-2-(5-amino-6-methyl-1-oxoisoquinolin-2(1H)-yl)propyl acetate

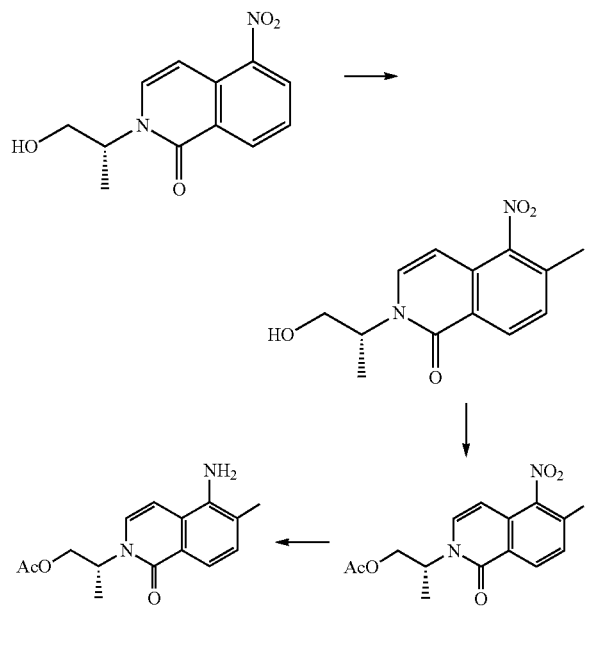

(R)-2-(1-hydroxypropan-2-yl)-6-methyl-5-nitroisoquinolin-1(2H)-one

A round bottom flask was charged with potassium tert-Butoxide (3.62 g, 0.0322 mol) and N,N-dimethylformamide (100 mL, 1 mol) and a solution of acetic acid, chloro-, 1,1-dimethylethyl ester (1.3 mL, 0.0089 mol) and (R)-2-(1-hydroxypropan-2-yl)-5-nitroisoquinolin-1(2H)-one (2.00 g, 0.00806 mol) in N,N-dimethylformamide (20 mL, 0.2 mol) was added at −20° C. dropwise over a period of 8 minutes and the reaction was stirred for an additional 45 minutes at the same temperature. The reaction mixture was poured onto 4 ml of hydrochloric acid and 80 mL of water, and extracted with dichloromethane, washed with brine and dried. the solvent was removed under reduced pressureunder reduced pressure and the residue was used in the next reaction without purification (two isomers in the ratio of 3:1). The residue was treated with trifluoroacetic acid (10 mL, 0.1 mol) for 30 minutes and the trifluoroacetic acid was removed under reduced pressure. The residue was stirred with potassium carbonate (2.2 g, 0.016 mol) in N,N-dimethylformamide (10 mL) at 50° C. for 1 hour. The reaction mixture was cooled and diluted with ethyl acetate (400 mL), washed with 6 N hydrochloric acid (50 mL×4) and the brine (50 mL×2), and dried. The volatiles were removed under reduced pressure and the residue was purified by column chromatography to afford the product as a yellow solid.

MS m/z=263.2 (M+H).

(R)-2-(6-methyl-5-nitro-1-oxoisoquinolin-2(1H)-yl) propyl acetate

To a solution of (R)-2-(1-hydroxypropan-2-yl)-6-methyl-5-nitroisoquinolin-1 (2H)-one (4.8 g, 0.018 mol) in methylene chloride (100 mL, 2 mol) was added acetic anhydride (7 g, 0.07 mol), triethylamine (10 g, 0.1 mol) and 4-Dimethylaminopyridine (20 mg, 0.0002 mol). The mixture was stirred at room temperature for 1 hour, washed with 1N hydrochloric acid and brine, and dried. The volatiles were removed under reduced pressure and the residue was purified by column chromatography to afford a yellow-brown oil.

MS m/z=305.2 (M+H).

$^1$H NMR (400 MHz, CDCl$_3$,) δ 8.47 (d, J=8.3 Hz, 1H), 7.39 (d, J=8.3 Hz, 1H), 7.23 (d, J=7.9 Hz, 1H), 6.44 (d, J=7.8 Hz, 1H), 5.42-5.38 (m, 1H), 4.33-4.31 (m, 2H), 2.49 (s, 2.00 (s, 3H), 1.46 (d, J=7.2 Hz, 3H).

(R)-2-(5-amino-6-methyl-1-oxoisoquinolin-2(1H)-yl)propyl acetate

A round bottom flask was charged with (R)-2-(6-methyl-5-nitro-1-oxoisoquinolin-2(1H)-yl)propyl acetate (3.4 g, 0.010 mol), ethanol (60 mL, 1 mol), and the solution was heated at 85° C. Ammonium chloride (6 g, 0.1 mol) in water (15 mL, 0.83 mol) was added followed by iron (2 g, 0.04 mol) in two portions. The reaction was stirred for 1 hour and poured onto dichloromethane (200 mL) and extracted. the solvent was removed under reduced pressureunder reduced pressure and the residue was purified by flash chromatography to afford the desired product as a light yellow oil.

MS m/z=275.2 (M+H).

$^1$H NMR (400 MHz, CDCl$_3$,) δ 7.84 (d, J=8.1 Hz, 1H), 7.22 (d, J=8.2 Hz, 1H), 7.09 (d, J=7.8 Hz, 1H), 6.47 (d, J=7.8 Hz, 1H), 5.48-5.45 (m, 1H), 4.37-4.29 (m, 2H), 2.31 (s, 3H), 2.00 (s, 3H), 1.44 (d, J=7.1 Hz, 3H)

General Synthetic Methods for Preparation of the Compounds of Invention

Method 1

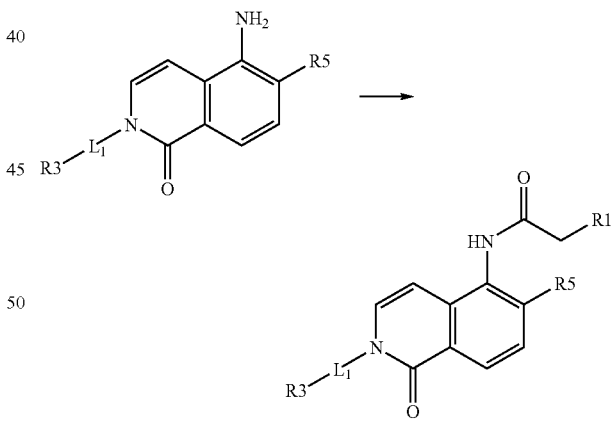

To a solution of the appropriate acid (0.003 mol) in methylene chloride (5 mL, 0.08 mol) was added oxalyl chloride (0.3 mL, 0.003 mol) and a drop of N,N-dimethylformamide at 0° C. The reaction was stirred at that temperature for 1 h. the solvent was removed under reduced pressureunder reduced pressure and dried under nitrogen. The residue was dissolved in methylene chloride (5 mL, 0.08 mol) and added to a solution of 5-amino-isoquinolone derivative (0.0016 mol) in methylene chloride (5 mL, 0.08 mol) and N,N-dimethylformamide (2 mL, 0.02 mol). The reaction mixture was stirred for 2 hours. the solvent was removed under reduced pressure and the residue was dissolved in 1:3 isopropyl alcohol/chloroform and washed with 1N hydrochloric acid. the solvent was removed under reduced pressure and the residue was purified by flash chromatography to afford the desired product.

Method 2

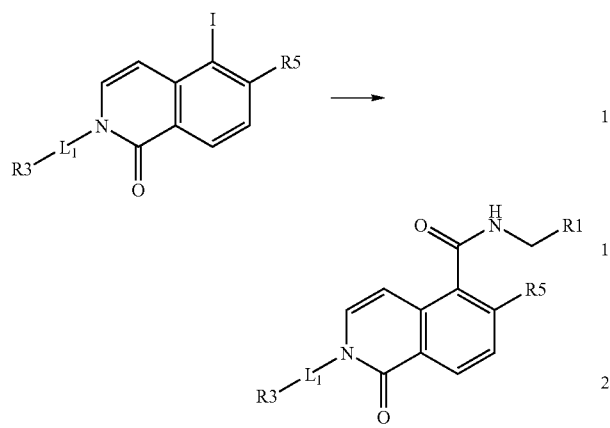

A 5 mL process vial was charged with the 5-iodo-1-oxoisoquinoline derivative (0.0009 mol), the appropriate amine (0.0018 mol), molybdenum hexacarbonyl (500 mg, 0.002 mol), palladium acetate (15 mg, 0.000067 mol), 1,8-diazabicyclo[5.4.0]undec-7-ene (500 mg, 0.003 mol) and 1,4-dioxane (4 mL, 0.04 mol). The vessel was sealed under air and stirred at 110° C. for 1 hour, and cooled to room temperature. The mixture was concentrated, dissolved in a small amount of dichloromethane, purified via flash chromatography to afford the desired product.

Representative Synthetic Methods

Method A

Compound 2

(R)-2-(6-Chloro-1-oxo-5-(2-adamantylacetamido)isoquinolin-2(1H)-yl)propanamide a. (R)-2-(6-Chloro-5-nitro-1-oxoisoquinolin-2(1H)-yl)propanamide To a solution of 6-chloro-5-nitro-1H-isochromen-1-one (950 mg, 0.0042 mol) in methanol (30 mL, 0.7 mol) was added triethylamine (0.64 mL, 0.0046 mol) and (R)-2-aminopropanamide hydrochloride (0.58 g, 0.0046 mol). The reaction was heated to 55° C. overnight and the solvent was removed under reduced pressure. The residue was purified by flash chromatography to afford the product as light yellow solid.

MS m/z=296.4 (M+H).

b. (R)-2-(5-Amino-6-chloro-1-oxoisoquinolin-2(1H)-yl)propanamide

To a solution of (R)-2-(6-chloro-5-nitro-1-oxoisoquinolin-2(1H)-yl)propanamide (120 mg, 0.00040 mol) in ethanol (4 mL, 0.07 mol) was added ammonium chloride (200 mg, 0.004 mol) in water (4 mL, 0.2 mol). The reaction was heated at 85° C. and iron (90 mg, 0.002 mol) was added in two portions 5 minutes apart. The reaction was stirred for 30 minutes and ethyl acetate was added and decanted. the solvent was removed under reduced pressureunder reduced pressure to afford the product as a yellow solid.

MS m/z=265.5 (M+H).

c. (R)-2-(6-Chloro-1-oxo-5-(2-adamantylacetamido)isoquinolin-2(1H)-yl)propanamide To a solution of 1-adamantaneacetic acid (600 mg, 0.003 mol) in methylene chloride (5 mL, 0.08 mol) was added oxalyl chloride (0.3 mL, 0.003 mol) and a drop of N,N-dimethylformamide at 0° C. The reaction was stirred at that temperature for 1 h. the solvent was removed under reduced pressureunder reduced pressure and dried under nitrogen. The residue was redissolved in methylene chloride (5 mL, 0.08 mol) and added to a solution of (R)-2-(5-amino-6-chloro-1-oxoisoquinolin-2(1H)-yl)propanamide (420 mg, 0.0016 mol) in methylene chloride (5 mL, 0.08 mol) and N,N-dimethylformamide (2 mL, 0.02 mol), and stirred for 2 hours. the solvent was removed under reduced pressure and

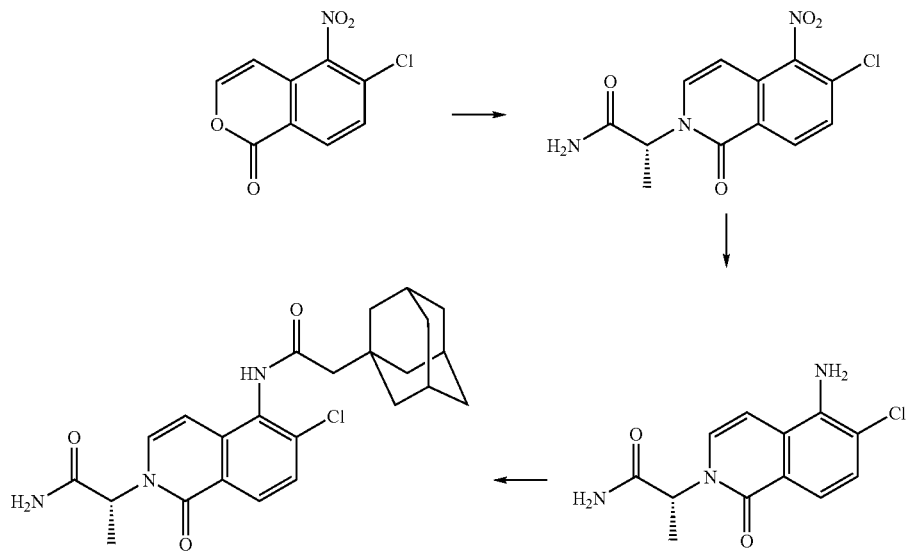

the residue was dissolved in 1:3 isopropyl alcohol/chloroform and washed with 1N hydrochloric acid. the solvent was removed under reduced pressure and the residue was purified by flash chromatography to afford the product as an off white solid.

MS m/z=442.2 (M+H).

$^1$H NMR (400 MHz, DMSO -d6) δ:9.75 (s, 1H), 8.13 (d, J=8.48 Hz, 1H), 7.67 (s, 1H), 7.59 (d, J=8.48 Hz, 1H), 7.54 (d, J=7.79 Hz, 1H), 7.25 (s, 1H), 6.49 (d, J=7.7 Hz, 1H), 5.48-5.43 (q, J=7.20 Hz, 1H), 2.19 (s, 2H), 1.97 (bs, 3H), 1.72-1.61 (m, 12H), 1.54 (d, J=8.67 Hz, 3H).

Method B

Compound 7

(R)-2-{6-Methoxy-1-oxo-5-[2-(4-trifluoromethyl-phenyl)-acetylamino]-1H-isoquinolin-2-yl}-propionamide

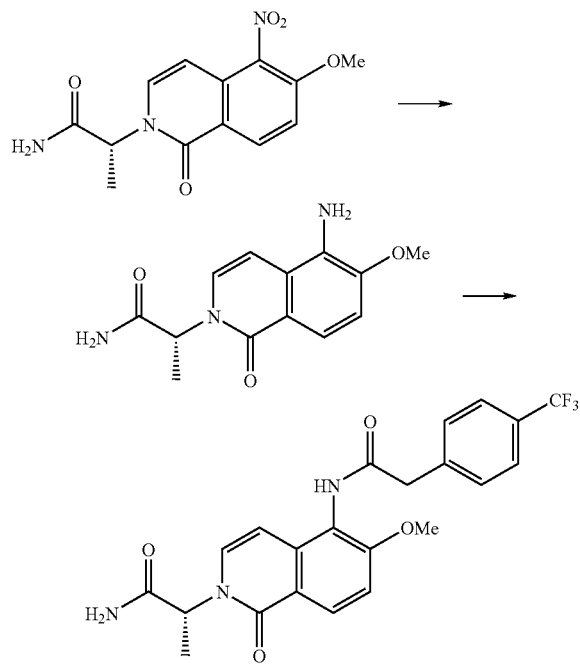

a. (R)-2-(5-Amino-6-methoxy-1-oxoisoquinolin-2 (1H)-yl)propanamide

A mixture of (R)-2-(6-methoxy-5-nitro-1-oxoisoquinolin-2(1H)-yl)propanamide (200 mg, 0.0007 mol), methanol (20 mL, 0.5 mol) and palladium, 10% weight on charcoal (21 mg, 0.00017 mol) was stirred under hydrogen (1 atm) for 3 h. The reaction mixture was filtered over celite and the solvent was removed to afford the product as a brown solid.

MS m/z=263.3 (M+H).

b. (R)-2-(6-Methoxy-1-oxo-5-(2-(4-(trifluoromethyl) phenyl)acetamido)isoquinolin-2(1H)-yl)propanamide A mixture of (R)-2-(5-amino-6-methoxy-1-oxoisoquinolin-2(1H)-yl)propanamide (98.34 mg, 0.0003764 mol), 2-(4-(trifluoromethyl)phenyl)acetic acid (115.2 mg, 0.0005646 mol), N,N-diisopropylethylamine (163.9 µL, 0.0009409 mol), N,N,N,N',N'-tetramethyl-O-(7-azabenzotriazol-1-yl) uronium hexafluorophosphate (357.8 mg, 0.0009409 mol) and N,N-dimethylformamide (2 mL, 0.02 mol) was stirred at room temperature overnight. the solvent was removed under reduced pressure and the residue purified by reverse phase preparative HPLC to afford the product as a light yellow solid.

MS m/z=448.3 (M+H).

$^1$H NMR (400 MHz; DMSO-d6) δ 9.71 (s, 1H), 8.17 (d, J=8.87 Hz, 1H), 7.74 (d, J=7.76 Hz, 2H), 7.62 (d, J=7.76 Hz, 2H), 7.34-7.29 (m, 2H), 7.20 (s, 1H), 6.28 (d, J=8.48 Hz, 1H), 5.45 (q, J=7.07 Hz, 1H), 3.90 (s, 3H), 3.84 (s, 2H), 1.49 (d, J=7.39 Hz, 3H).

Method C

Compound 8

(S)-2-{6-Chloro-1-oxo-5-[2-(4-trifluoromethyl-phenyl)-acetylamino]-1H-isoquinolin-2-yl}-propionamide

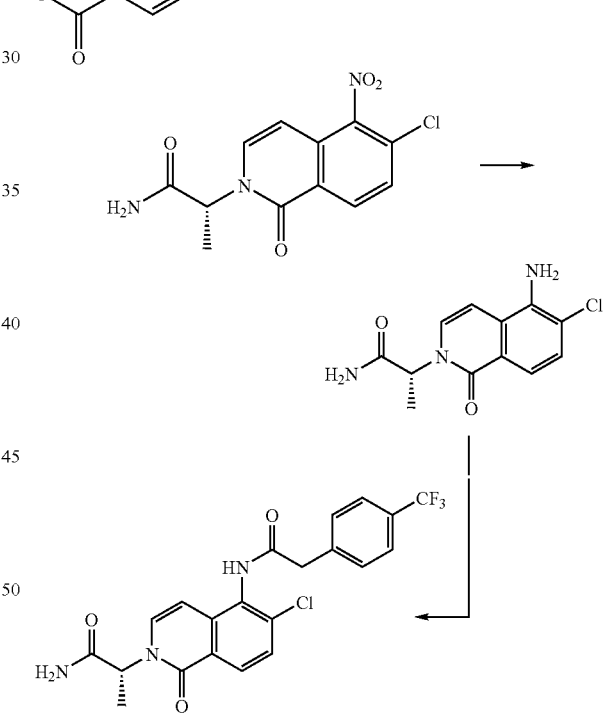

a. (S)-2-(6-Chloro-5-nitro-1-oxoisoquinolin-2(1H)-yl)propanamide

A mixture of 6-chloro-5-nitro-1H-isochromen-1-one (230 mg, 0.00102 mol), (S)-2-aminopropanamide hydrochloride (127 mg, 0.00102 mol), triethylamine (142 µL, 0.00102 mol) and methanol (20 mL, 0.5 mol) was stirred at 60° C. for 3 hours. the solvent was removed under reduced pressure and the residue was purified by flash chromatography to afford the product as a yellow solid.

MS m/z=262.3 (M+H).

b. (S)-2-(5-Amino-6-chloro-1-oxoisoquinolin-2(1H)-yl)propanamide

A mixture of (S)-2-(6-chloro-5-nitro-1-oxoisoquinolin-2(1H)-yl)propanamide (201 mg, 0.000679 mol), ethanol (10 mL, 0.2 mol), ammonium chloride (363.03 mg, 0.0067868 mol) and water (10 mL, 0.6 mol) was heated at 85° C. Iron (152 mg, 0.00271 mol) was added in three portions, 2 minutes apart and the reaction was stirred at that temperature for 1 hour. The mixture was poured onto dichloromethane (150 mL) and the layers were separated. The organic layer was washed with brine, dried, and the solvent was removed under reduced pressure to afford the product as a light yellow solid.

MS m/z=232.5 (M+H).

c. (S)-2-(6-Chloro-1-oxo-5-(2-(4-(trifluoromethyl)phenyl)acetamido)isoquinolin-2(1H)-yl)propanamide A mixture of (S)-2-(5-amino-6-chloro-1-oxoisoquinolin-2(1H)-yl)propanamide (100.0 mg, 0.0003764 mol), 2-(4-(trifluoromethyl)phenyl)acetic acid (115.2 mg, 0.0005646 mol), N,N-diisopropylethylamine (163.9 μL, 0.0009409 mol), N,N,N',N'-tetramethyl-O-(7-azabenzotriazol-1-yl)uronium hexafluorophosphate (357.8 mg, 0.0009409 mol) and N,N-dimethylformamide (2 mL, 0.02 mol) was stirred at 60° C. for 3 days. the solvent was removed under reduced pressure and the residue purified by reverse phase preparative HPLC to afford the product as light yellow solid.

MS m/z=452.1 (M+H).

$^1$H NMR (400 MHz; DMSO-d6) δ10.21 (s, 1H), 8.15 (d, J=8.68 Hz, 1H), 7.74 (d, J=7.76 Hz, 2H), 7.66-7.58 (m, 4H), 7.49 (d, J=7.95 Hz, 1H), 7.25 (s, 1H), 6.43 (d, J=7.50 Hz, 1H), 5.47-5.42 (q, J=7.07 Hz, 1H), 3.90 (s, 2H), 1.53 (d, J=7.39 Hz, 3H).

Method D

Compound 11

N-[6-Chloro-2-((R)-2-hydroxy-1-methyl-ethyl)-1-oxo-1,2-dihydro-isoquinolin-5-yl]-2-(3-fluoro-4-trifluoromethyl-phenyl)-acetamide

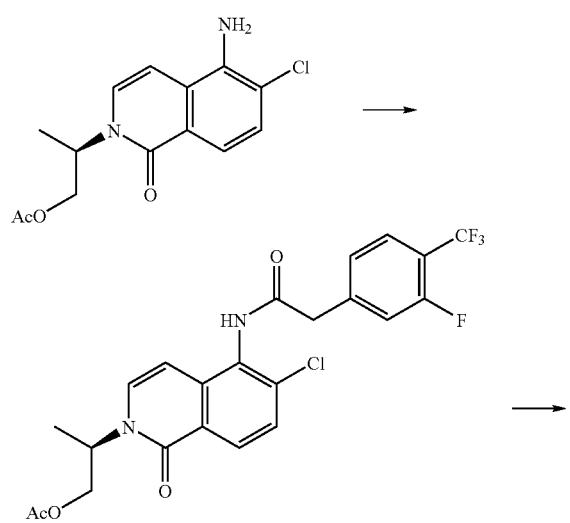

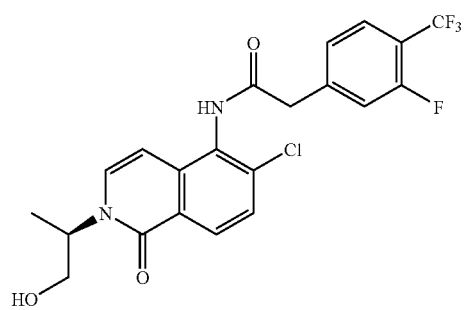

a. (R)-2-(6-Chloro-5-(2-(3-fluoro-4-(trifluoromethyl)phenyl)acetamido)-1-oxoisoquinolin-2(1H)-yl)propyl acetate A vial was charged with (R)-2-(5-amino-6-chloro-1-oxoisoquinolin-2(1H)-yl)propyl acetate (160 mg, 0.00054 mol), methylene chloride (10 mL, 0.2 mol), 2-(3-fluoro-4-(trifluoromethyl)phenyl)acetic acid (145 mg, 0.000651 mol), N,N,N',N'-tetramethyl-O-(7-azabenzotriazol-1-yl)uronium hexafluorophosphate (413 mg, 0.00108 mol), and N,N-diisopropylethylamine (0.189 mL, 0.00108 mol), and was stirred at 40° C. for 2 days. the solvent was removed under reduced pressureunder reduced pressure and the residue was purified by flash chromatography to afford the product as colorless oil.

MS m/z=499.3 (M+H)

b. (R)—N-(6-Chloro-2-(1-hydroxypropan-2-yl)-1-oxo-1,2-dihydroisoquinolin-5-yl)-2-(3-fluoro-4-(trifluoromethyl)phenyl)acetamide A round bottom flask was charged with (R)-2-(6-chloro-5-(2-(3-fluoro-4-(trifluoromethyl)phenyl)acetamido)-1-oxoisoquinolin-2(1H)-yl)propyl acetate (1.200 g, 0.002406 mol), potassium carbonate (0.997 g, 0.00722 mol) and methanol (20 mL, 0.5 mol) and 2 drops of water. The reaction was stirred at room temperature for 1 hour and was filtered over sodium sulfate and washed with methanol. the solvent was removed under reduced pressureunder reduced pressure and the residue purified by flash chromatography to afford the product as a white solid.

MS m/z=457.3 (M+H).

$^1$H NMR (400 MHz, DMSO-d$_6$): δ10.20 (s, 1H), 8.17 (d, J=8.54 Hz, 1H), 7.79 (t, J=8.21 Hz, 1H), 7.60 (d, J=8.87 Hz, 1H), 7.56-7.51 (m, 2H), 7.45 (d, J=8.54 Hz, 1H), 6.44 (d, J=7.90 Hz, 1H), 5.03-4.99 (m, 1H), 4.94 (t, J=5.21 Hz, 1H), 3.94 (s, 2H), 3.68-3.56 (m, 2H), 1.28 (d, J=7.51 Hz, 3H).

Method E

Compound 13

N-[6-Chloro-2-((R)-2-hydroxy-1-methyl-ethyl)-1-oxo-1,2-dihydro-isoquinolin-5-yl]-2-(4-fluoro-3-trifluoromethyl-phenyl)-acetamide

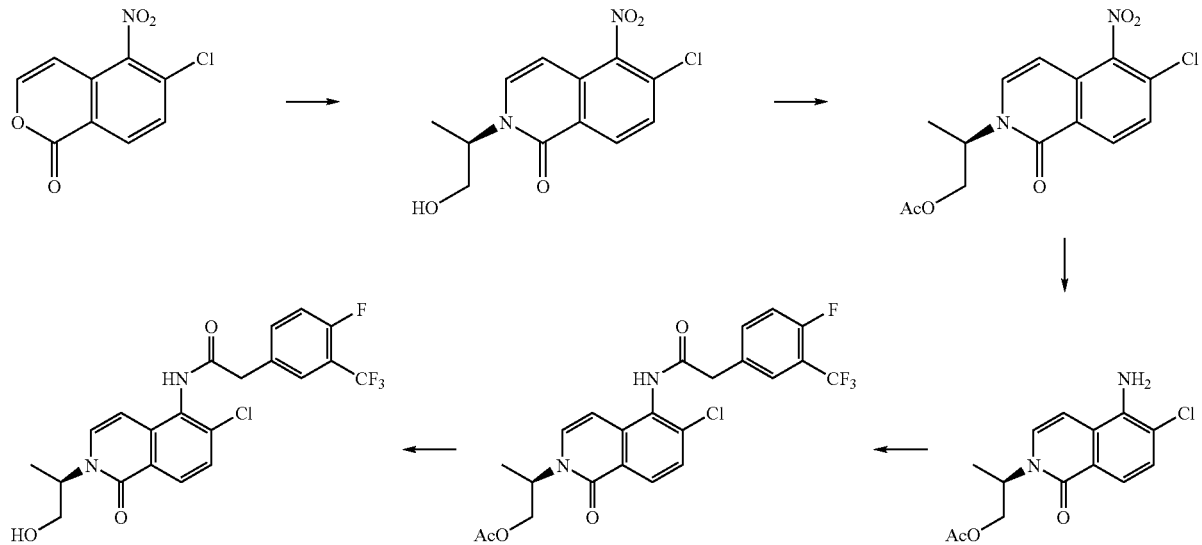

a. (R)-6-Chloro-2-(1-hydroxypropan-2-yl)-5-nitroisoquinolin-1(2H)-one

A microwave vial was charged with 6-chloro-5-nitro-1H-isochromen-1-one (80.0 mg, 0.000355 mol), (2R)-2-aminopropan-1-ol (29 mg, 0.00039 mol), triethylamine (0.15 mL, 0.0011 mol) and methanol (4 mL, 0.1 mol), and heated under microwave irradiation at 100° C. for 30 minutes. the solvent was removed under reduced pressure and the residue purified by flash chromatography to afford the desired product as a light yellow solid.

MS m/z=283.2 (M+H).
$^1$H NMR (400 MHz; DMSO-d6) δ8.43 (d, J=8.86 Hz, 1H), 7.80 (d, J=8.86Hz, 1H), 7.75 (d, J=7.98 Hz, 1H), 6.36 (d, J=7.09 Hz, 1H), 5.03-4.86 (m, 2H), 3.63-3.52 (m, 2H), 1.30 (d, J=7.0Hz, 3H).

b. (R)-2-(6-Chloro-5-nitro-1-oxoisoquinolin-2(1H)-yl)propyl acetate

A mixture of (R)-6-chloro-2-(1-hydroxypropan-2-yl)-5-nitroisoquinolin-1 (2H)-one (2H)-one 750.0 mg, 0.002653 mol), acetic anhydride (0.325 mL, 0.00345 mol), pyridine (0.322 mL, 0.00398 mol) and methylene chloride (20 mL, 0.3 mol) was heated at 45° C. over night. The solvents were removed under reduced pressure and dried to afford the product as a thick yellow oil.

MS m/z=325.4 (M+H).
$^1$H NMR (400 MHz; DMSO-d6) δ8.42 (d, J=8.61 Hz, 1H), 7.47 (d, J=8.61 Hz, 1H), 7.23 (d, J=8.6 Hz, 1H), 6.29 (d, J=8.03 Hz, 1H), 5.34-5.29 (m, 1H), 4.28-4.20 (m, 2H), 1.94 (s, 3H), 1.40 (d, J=6.96 Hz, 3H).

c. (R)-2-(5-Amino-6-chloro-1-oxoisoquinolin-2(1H)-yl)propyl acetate

A round bottom flask was charged with (R)-2-(6-chloro-5-nitro-1-oxoisoquinolin-2(1H)-yl)propyl acetate (160.0 mg, 0.0004927 mol) and ethanol (7 mL, 0.1 mol), and the reaction was heated at 85° C. Ammonium chloride (264 mg, 0.00493 mol) in water (7 mL, 0.4 mol) was added, followed by iron (110 mg, 0.0020 mol) in two portions. The reaction was stirred at that temperature for one hour. The reaction mixture was then poured onto dichloromethane (60 mL) and extracted. The extracts were washed with brine, dried, and the solvent removed under reduced pressure to afford the product as a colorless solid.

MS m/z=295.5 (M+H).

d. (R)-2-(6-Chloro-5-(2-(4-fluoro-3-(trifluoromethyl)phenyl)acetamido)-1-oxoisoquinolin-2(1H)-yl)propyl acetate A reaction vial was charged with (R)-2-(5-amino-6-chloro-1-oxoisoquinolin-2(1H)-yl)propyl acetate (210 mg, 0.00071 mol), 2-(4-fluoro-3-(trifluoromethyl)phenyl)acetic acid (300 mg, 0.001 mol), N,N,N',N'-tetramethyl-O-(7-azabenzotriazol-1-yl)uronium hexafluorophosphate (600 mg, 0.002 mol), N,N-diisopropylethylamine (600 μL, 0.003 mol) and was stirred at 50° C. for 5 days. the solvent was removed under reduced pressureunder reduced pressure and the residue was purified by flash chromatography to afford the product as a light yellow oil.

MS m/z=499.3 (M+H).

e. (R)—N-(6-Chloro-2-(1-hydroxypropan-2-yl)-1-oxo-1,2-dihydroisoquinolin-5-yl)-2-(4-fluoro-3-(trifluoromethyl)phenyl)acetamide A round bottom flask was charged with (R)-2-(6-chloro-5-(2-(4-fluoro-3-(trifluoromethyl)phenyl)acetamido)-1-oxoisoquinolin-2(1H)-yl)propyl acetate (250 mg, 0.00050 mol), potassium carbonate (100 mg, 0.00075 mol) and methanol (8 ML, 0.2 mol) and 2 drops of water. The reaction was stirred at room temperature for 30 minutes. The reaction mixture was filtered and washed with methanol. the solvent was removed under reduced pressureunder reduced pressure and the residue purified by reverse phase preparative HPLC to afford the product as an off white solid.

MS m/z=457.4 (M+1).

$^1$H NMR (400 MHz; DMSO-d6) δ10.17 (s, 1H), 8.16 (d, J=8.85 Hz, 1H), 7.82 (d, J=7.76 Hz, 1H), 7.72-7.74 (m, 1H), 7.59 (d, J=8.84 Hz, 1H), 7.54-7.49 (m, 2H), 6.42 (d, J=7.50 Hz, 1H), 5.03-4.93 (m, 2H), 3.90 (s, 2H), 3.66-3.56 (m, 2H), 1.28 (d, J=7.63 Hz, 3H).

Method F

Compound 17

N—[6-Cyclopropyl-2-((R)-2-hydroxy-1-methyl-ethyl)-1-oxo-1,2-dihydro-isoquinolin-5-yl]-2-(3-fluoro-4-trifluoromethyl-phenyl)-acetamide

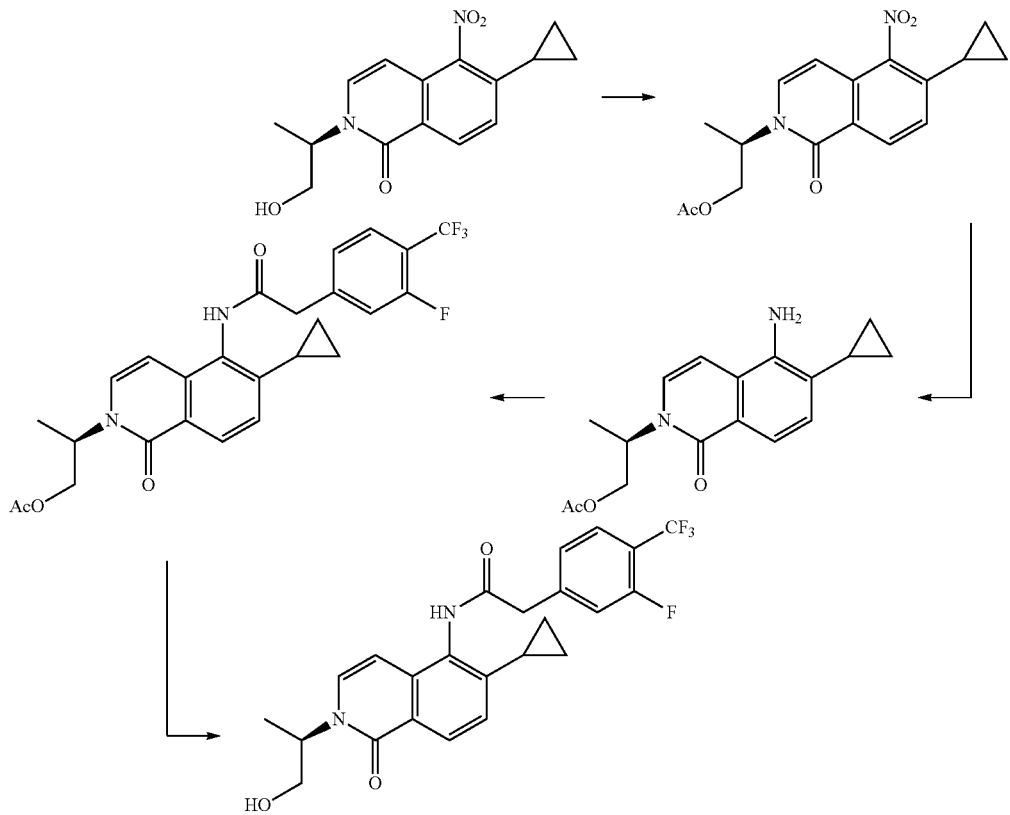

a. (R)-2-(6-Cyclopropyl-5-nitro-1-oxoisoquinolin-2 (1H)-yl)propyl acetate

A round bottom flask was charged with (R)-6-cyclopropyl-2-(1-hydroxypropan-2-yl)-5-nitroisoquinolin-1(2H)-one (30 mg, 0.0001 mol), acetic anhydride (0.015 mL, 0.00016 mol), pyridine (0.015 mL, 0.00019 mol) and methylene chloride (4 mL, 0.06 mol), and was stirred at room temperature overnight. The solvent was removed under reduced pressure and the product was taken onto the next step without purification.

MS m/z=331.5 (M+H).

b. (R)-2-(5-Amino-6-cyclopropyl-1-oxoisoquinolin-2 (1H)-yl)propyl acetate

A round bottom flask was charged with (R)-2-(6-cyclopropyl-5-nitro-1-oxoisoquinolin-2(1H)-yl)propyl acetate (28 mg, 0.000085 mol), ethanol (10 mL, 0.2 mol) and palladium, 10% weight on charcoal (1.0 mg, 0.0000085 mol) was added. The flask was evacuated and flushed with hydrogen two times and the reaction was stirred under hydrogen (1 atm) for 2 hours. The reaction was filtered over celite and the solvent was removed to afford the product.

MS m/z=301.2 (M+H).

c. (R)-2-(6-Cyclopropyl-5-(2-(3-fluoro-4-(trifluoromethyl)phenyl)acetamido)-1-oxoisoquinolin-2 (1H)-yl)propyl acetate A reaction vial was charged with (R)-2-(5-amino-6-cyclopropyl-1-oxoisoquinolin-2(1H)-yl)propyl acetate (23.0 mg, 0.0000766 mol), 2-(3-fluoro-4-(trifluoromethyl)phenyl)acetic acid (26 mg, 0.00011 mol), N,N,N',N'-tetramethyl-O-(7-azabenzotriazol-1-yl)uronium hexafluorophosphate (73 mg, 0.00019 mol), N,N-diisopropylethylamine (33 μL, 0.00019 mol) and methylene chloride (2 mL, 0.03 mol) and the reaction was stirred at 40° C. over night. the solvent was removed under reduced pressure and the residue purified by flash chromatography to afford the product as light yellow solid.

MS m/z=505.3 (M+H).

d. (R)—N-(6-Cyclopropyl-2-(1-hydroxypropan-2-yl)-1-oxo-1,2-dihydroisoquinolin-5-yl)-2-(3-fluoro-4-(trifluoromethyl)phenyl)acetamide A round bottom flask was charged with (R)-2-(6-cyclopropyl-5-(2-(3-fluoro-4-(trifluoromethyl)phenyl)acetamido)-1- oxoisoquinolin-2(1H)-yl)propyl acetate (23 mg, 0.000046 mol), potassium carbonate (9.4 mg, 0.000068 mol) and methanol (2 mL, 0.05 mol) and 2 drops of water and the reaction was stirred for 30 minutes. The reaction mixture was filtered over celite and the solvent removed under reduced pressure. The residue was purified by reverse phase preparative HPLC to afford the product.

MS m/z=463.5 (M+H).

H NMR (400 MHz; Acetone-$d_6$) δ9.02 (s, 1H), 8.03 (d, J=8.15 Hz, 1H), 7.61 (t, J=7.52 Hz, 1H), 7.42 (d, J=5.01 Hz, 1H), 7.39 (s, 1H), 7.24 (d, J=7.52 Hz, 1H), 6.91 (d, J=8.15 Hz, 1H), 6.36 (d, J=8.15 Hz, 1H), 4.99-4.97 (m, 1H), 3.93 (s, 2H), 3.68-3.64 (m, 2H), 2.04-1.94 (m, 1H), 1.24 (d, J=7.32 Hz, 3H), 0.81-0.77 (m, 2H), 0.60-0.56 (m, 2H).

Method G

Compound 18

2-(2-Fluoro-3-trifluoromethyl-phenyl)-N-[2-(2-hydroxy-ethyl)-6-(2-hydroxy-ethylamino)-1-oxo-1,2-dihydro-isoquinolin-5-yl]-acetamide

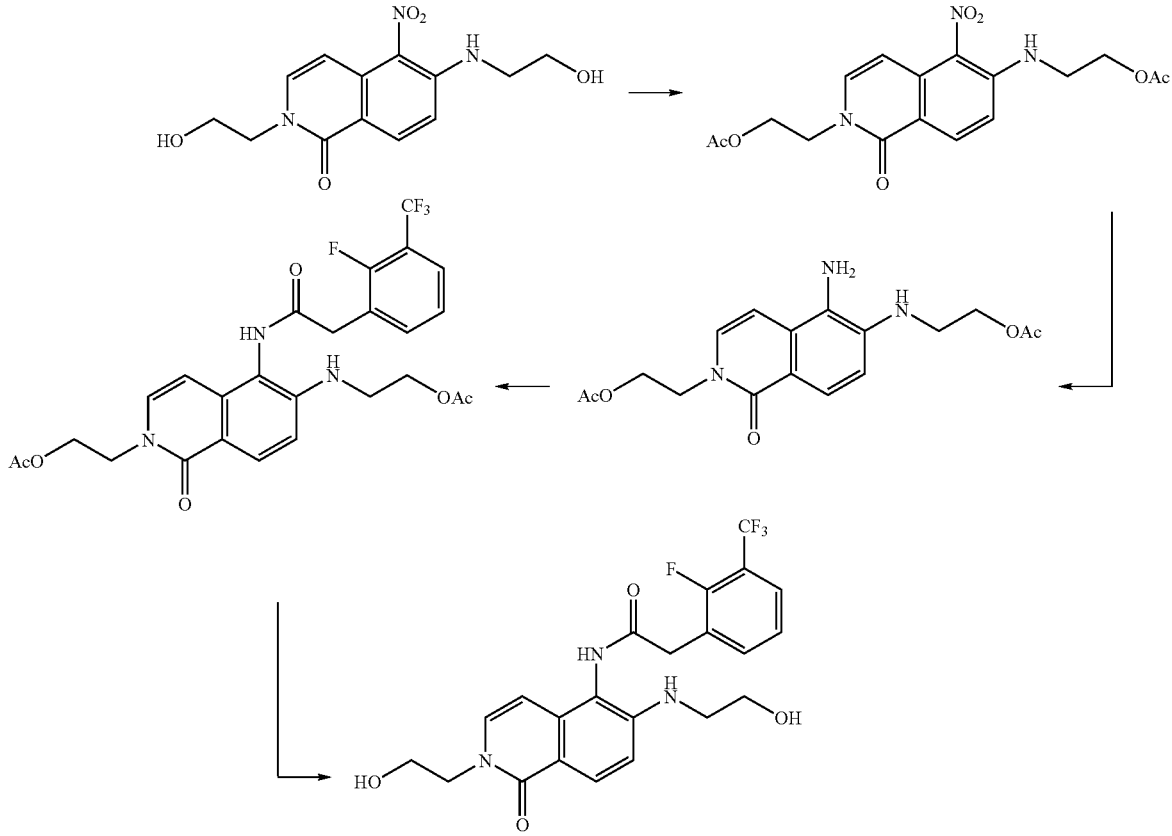

a. 2-(2-(2-Acetoxyethyl)-5-nitro-1-oxo-1,2-dihydroisoquinolin-6-ylamino)ethyl acetate A round bottom flask was charged with 2-(2-hydroxyethyl)-6-(2-hydroxyethylamino)-5-nitroisoquinolin-1(2H)-one (300.0 mg, 0.0010 mol), acetic anhydride (0.24 mL, 0.0026 mol), pyridine (0.33 mL, 0.0041 mol) and methylene chloride (10 mL, 0.2 mol) and was heated at 45° C. overnight. the solvent was removed under reduced pressureunder reduced pressure to afford the product which was used in the next reaction without further purification.

MS m/z=378.2 (M+H).

b. Acetic acid 2-[6-(2-acetoxy-ethylamino)-5-amino-1-oxo-1H-isoquinolin-2-yl]-ethyl ester A mixture of 2-(2-(2-acetoxyethyl)-5-nitro-1-oxo-1,2-dihydroisoquinolin-6-ylamino)ethyl acetate (350 mg, 0.00093 mol), ethanol (20 mL, 0.3 mol), ammonium chloride (496.1 mg, 0.009275 mol) and water (10 mL, 0.6 mol) was added at 85° C. Iron (207 mg, 0.00371 mol) was added in two portions, five minutes apart, and was stirred at that temperature for 1 hour. The reaction mixture was then poured onto methylene chloride (100 mL) and the layers were separated. The organic layer was washed with brine and dried. the solvent was removed under reduced pressureunder reduced pressure and the product was used in the next step without purification.

MS m/z=348.5 (M+H).

c. 2-(2-(2-Acetoxyethyl)-5-(2-(2-fluoro-3-(trifluoromethyl)phenyl)acetamido)-1-oxo-1,2-dihydroisoquinolin-6-ylamino)ethyl acetate A reaction vial was charged with acetic acid 2-[6-(2-acetoxy-ethylamino)-5-amino-1-oxo-1H-isoquinolin-2-yl]-ethyl ester (100.00 mg, 0.000 28788 mol), 2-(2-fluoro-3-(trifluoromethyl)phenyl)acetic acid (76.74 mg, 0.0003454 mol), N,N,N',N'-tetramethyl-O-(7-azabenzotriazol-1-yl)uronium hexafluorophosphate (274 mg, 0.000720 mol), N,N-diisopropylethylamine (0.125 mL, 0.000720 mol) and methylene chloride (3 mL, 0.05 mol). The reaction was heated at 40° C. for 5 h. The solvent was removed under reduced pressure and the residue purified by flash chromatography to afford the product as an off white solid.

MS m/z=552.3 (M+H).

d. 2-(2-Fluoro-3-(trifluoromethyl)phenyl)-N-(2-(2-hydroxyethyl)-6-(2-hydroxyethylamino)-1-oxo-1,2-dihydroisoquinolin-5-yl)acetamide A round bottom flask was charged with 2-(2-(2-acetoxyethyl)-5-(2-(2-fluoro-3-(trifluoromethyl)phenyl)acetamido)-1-oxo-1,2-dihydroisoquinolin-6-ylamino)ethyl acetate (120 mg, 0.00022 mol), potassium carbonate (45 mg, 0.00033 mol) and methanol (3 mL, 0.07 mol) and 2 drops of water. The reaction was stirred at room temperature for 30 minutes, filtered over sodium sulfate, and the solvent removed under reduced pressure. The residue was purified by flash chromatography to afford the product as a white solid.

MS m/z=468.4 (M+H).

$^1$H NMR (400 MHz; DMSO-d6) δ9.45 (s, 1H), 7.98 (d, J=8.95 Hz, 1H), 7.79 (t, J=7.45 Hz, 1H), 7.70 (t, J=7.09 Hz, 1H), 7.40 (t, J=7.83 Hz, 1H), 7.22 (d, J=7.83 Hz, 1H), 6.91 (d, J=9.08 Hz, 1H), 6.16 (d, J=7.73 Hz, 1H), 5.64 (t, J=5.72 Hz, 1H), 4.84 (t, J=5.33 Hz, 1H), 4.76 (t, J=5.48 Hz, 1H), 3.96 (s, 2H), 3.91 (t, J=5.27 Hz, 2H), 3.62-3.53 (m, 4H), 3.27 (q, J=6.15 Hz, 2H).

Method H

Compound 19

N—[6-Chloro-2-(2-hydroxy-ethyl)-1-oxo-1,2-dihydro-isoquinolin-5-yl]-2-(4-fluoro-3-trifluoromethyl-phenyl)-acetamide pa. 6-Chloro-2-(2-hydroxyethyl)-5-nitroisoquinolin-1(2H)-one

A microwave vial was charged with 6-chloro-5-nitro-1H-isochromen-1-one (1.0 g, 0.00443 mol), ethanolamine (0.401 mL, 0.00665 mol), triethylamine (1.24 mL, 0.00886 mol) and methanol (30 mL, 0.7 mol) and the reaction was subjected to microwave at 100° C. for 1 hour. the solvent was removed under reduced pressure and the residue purified by flash chromatography to afford the product as a yellow solid. MS m/z=269.4 (M+H). $^1$H NMR (400 MHz; CDCl$_3$) δ8.41 (d, J=8.56 Hz, 1H), 7.52 (d, J=8.56 Hz, 1H), 7.33 (d, J=8.4 Hz, 1H), 6.31 (d, J=8.56 Hz, 1H), 4.17 (t, J=44.88 Hz, 2H), 3.99 (t, J=5.11 Hz, 2H), 2.55 (bs, 1H).

b. 2-(6-Chloro-5-nitro-1-oxoisoquinolin-2(1H)-yl) ethyl acetate

A round bottom flask was charged with 6-chloro-2-(2-hydroxyethyl)-5-nitroisoquinolin-1(2H)-one (400.0 mg, 0.00149 mol), acetic anhydride (0.21 mL, 0.0022 mol), pyridine (0.18 mL, 0.0022 mol) and methylene chloride (20 mL, 0.2 mol) and the reaction was stirred at room temperature overnight. The solvent was removed under reduced pressure to afford the product as a yellow solid.

MS m/z=311.3 (M+H).

c. 2-(5-Amino-6-chloro-1-oxoisoquinolin-2(1H)-yl) ethyl acetate

A round bottom flask was charged with 2-(6-chloro-5-nitro-1-oxoisoquinolin-2(1H)-yl)ethyl acetate (450.00 mg, 0.0014484 mol), ethanol (20 mL, 0.3 mol), and ammonium

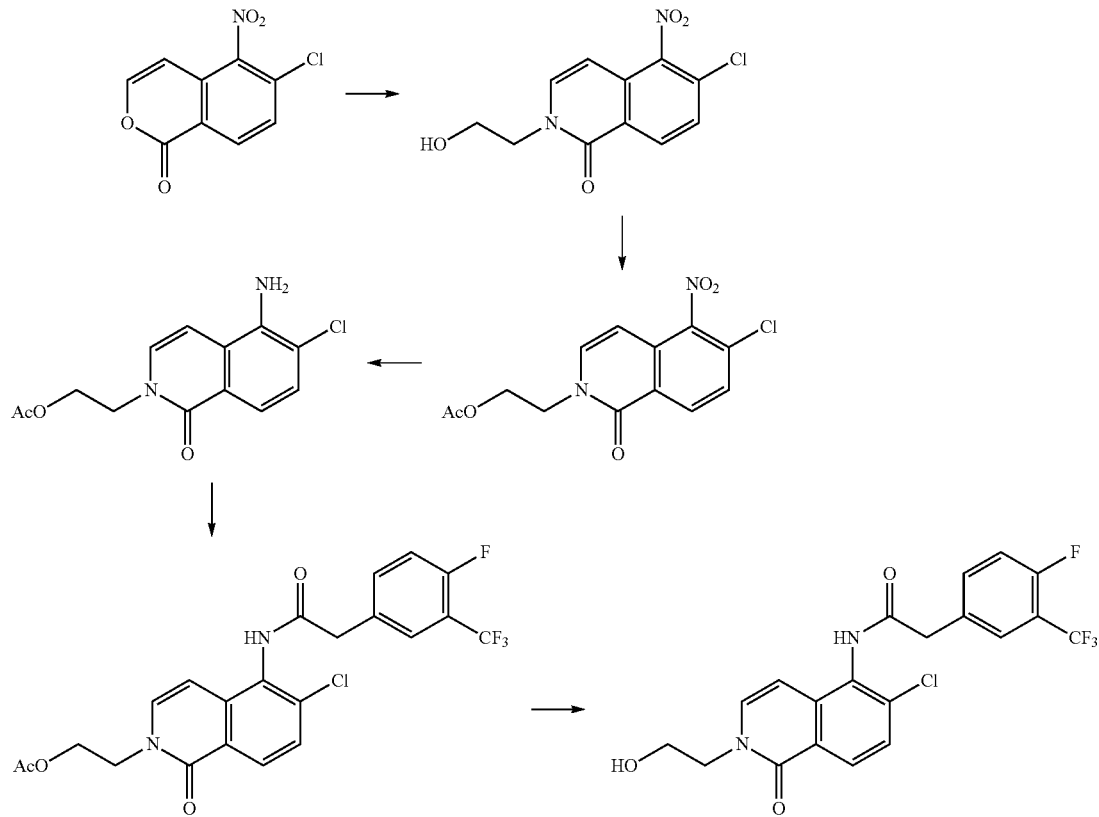

chloride (774.8 mg, 0.01448 mol) in water (10 mL, 0.6 mol) was added at 85° C., followed by iron (324 mg, 0.00579 mol) in two portions. The reaction was stirred at that temperature for 45 minutes and then poured onto methylene chloride (200 mL) and extracted. The solvent was removed under reduced pressure to afford the pure product as a light yellow solid.

MS m/z=281.3 (M+H)

d. 2-(6-Chloro-5-(2-(4-fluoro-3-(trifluoromethyl) phenyl)acetamido)-1-oxoisoquinolin-2(1H)-yl)ethyl acetate A reaction vial was charged with 2-(5-amino-6-chloro-1-oxoisoquinolin-2(1H)-yl)ethyl acetate (60.0 mg, 0.000214 mol), 2-(4-fluoro-3-(trifluoromethyl)phenyl)acetic acid (57.0 mg, 0.000256 mol), N,N,N',N'-tetramethyl-O-(7-azabenzotriazol-1-yl)uronium hexafluorophosphate (203 mg, 0.000534 mol), N,N-diisopropylethylamine (0.093 mL, 0.00053 mol) and methylene chloride (3 mL, 0.05 mol), and the reaction mixture was stirred at 45° C. for 4 days. The solvent was removed under reduced pressure and the residue was purified by flash chromatography to afford the product as a light yellow solid.

MS m/z=485.2 (M+H)

2 drops of water and the reaction was stirred for 20 minutes at room temperature. The reaction was filtered over sodium sulfate and celite and washed with methanol. The solvent was removed under reduced pressure and the residue purified by reverse phase preparative HPLC to afford the product as a pale yellow solid.

MS m/z=443.3 (M+H)

$^1$H NMR (400 MHz; DMSO-d6) δ10.18 (s, 1H), 8.15 (d, J=8.81 Hz, 1H), 7.82 (d, J=6.7 Hz, 1H), 7.77-7.74 (m, 1H), 7.59 (d, J=8.81 Hz, 1H), 7.52 (t, J=9.52 Hz, 1H), 7.46 (d, J=7.40 Hz, 1H), 6.40 (d, J=7.59 Hz, 1H), 4.88 (t, J=5.0 Hz, 1H), 4.00 (t, J=5.55 Hz, 2H), 3.89 (s, 2H), 3.65 (q, J=5.55 Hz, 2H).

Method I

Compound 21

N-[6-Methyl-2-((R)-2-hydroxy-1-methyl-ethyl)-1-oxo-1,2-dihydro-isoquinolin-5-yl]-2-(3-fluoro-4-trifluoromethyl-phenyl)-acetamide e. N-(6-Chloro-2-(2-hydroxyethyl)-1-oxo-1,2-dihydroisoquinolin-5-yl)-2-(4-fluoro-3-(trifluoromethyl) phenyl)acetamide A round bottom flask was charged with 2-(6-chloro-5-(2-(4-fluoro-3-(trifluoromethyl)phenyl)acetamido)-1-oxoisoquinolin-2(1H)-yl)ethyl acetate (80.0 mg, 0.000165 mol), potassium carbonate (34.2 mg, 0.000248 mol), methanol and a. (R)-2-(1-Hydroxypropan-2-yl)-6-methyl-5-nitroisoquinolin-1(2H)-one

A round bottom flask was charged with 6-methyl-5-nitro-1H-isochromen-1-one (260.00 mg, 0.0012673 mol), (2R)-2-aminopropan-1-ol (143 mg, 0.00190 mol), triethylamine (1.6 L, 0.011 mol) and methanol (5 mL, 0.1 mol) and the reaction was heated at 80° C. overnight. The solvent was removed under reduced pressure and the residue purified by flash chromatography to afford the product as a light yellow solid.
MS m/z=263.4 (M+H).

b. (R)-2-(6-Methyl-5-nitro-1-oxoisoquinolin-2(1H)-yl)propyl acetate

A mixture of (R)-2-(1-hydroxypropan-2-yl)-6-methyl-5-nitroisoquinolin-1-(2H)-one (100.0 mg, 0.0003813 mol), pyridine (0.062 mL, 0.00076 mol), acetic anhydride (0.0432 mL, 0.000458 mol) and methylene chloride (5 mL, 0.08 mol) was stirred at room temperature overnight. The solvent was removed under reduced pressure, and the resulting product was dried under vacuum (yellow oil) and was used in the next step without any purification.
MS m/z=305.4 (M+H).

c. (R)-2-(5-Amino-6-methyl-1-oxoisoquinolin-2(H1)-yl)propyl acetate

A round bottom flask was charged with (R)-2-(6-methyl-5-nitro-1-oxoisoquinolin-2(1H)-yl)propyl acetate (110.0 mg, 0.0003615 mol) and ethanol (10 mL, 0.2 mol and heated at 85° C. Ammonium chloride (193.4 mg, 0.003615 mol) in water (2 mL, 0.1 mol) was added, followed by iron (80.7 mg, 0.00144 mol) in two portions. The resulting mixture was stirred for 30 minutes at the same temperature. The reaction was poured onto dichloromethane (50 mL) and extracted, washed with brine and dried. The solvent was removed under reduced pressure to afford the product as an oil.
MS m/z=275.4 (M+H).

d. (R)-2-(5-(2-(3-Fluoro-4-(trifluoromethyl)phenyl)acetamido)-6-methyl-1-oxoisoquinolin-2(1H)-yl) propyl acetate A round bottom flask was charged with (R)-2-(5-amino-6-methyl-1-oxoisoquinolin-2(1H)-yl)propyl acetate (175 mg, 0.000638 mol), 2-(3-fluoro-4-(trifluoromethyl)phenyl)acetic acid (210 mg, 0.00096 mol), N,N,N',N'-tetramethyl-O-(7-azabenzotriazol-1-yl)uronium hexafluorophosphate (610 mg, 0.0016 mol), N,N-diisopropylethylamine (0.28 mL, 0.0016 mol) and N,N-dimethylformamide (8 mL, 0.1 mol). The reaction mixture was stirred at 45° C. for 24 hours. The reaction was quenched with water and extracted with ethyl acetate, washed with sodium bicarbonate, brine, and dried. The solvent was removed under reduced pressure and the residue was purified by flash chromatography to afford the product as a light yellow oil.
MS m/z=479.3 (M+H)

e. (R)-2-(3-Fluoro-4-(trifluoromethyl)phenyl)-N-(2-(1-hydroxypropan-2-yl)-6-methyl-1-oxo-1,2-dihydroisoquinolin-5-yl)acetamide A round bottom flask was charged with (R)-2-(5-(2-(3-fluoro-4-(trifluoromethyl)phenyl)acetamido)-6-methyl-1-oxoisoquinolin-2(1H)-yl)propyl acetate (300.00 mg, 0.62704 mmol), potassium carbonate (260 mg, 0.0019 mol), methanol (20 mL, 0.4 mol) and 2 drops of water. The reaction was stirred at room temperature for 20 minutes. The reaction was quenched with water and extracted with ethyl acetate, washed with sodium bicarbonate, brine, and dried The solvent was removed under reduced pressure to afford the product as a light yellow solid.
MS m/z=437.5 (M+H).

$^1$H NMR (400 MHz, DMSO-d$_6$): δ9.91 (s, 1H), 8.07 (d, J=8.45 Hz, 1H), 7.79 (t, J=7.85 Hz, 1H), 7.53 (d, J=12.68 Hz, 1H), 7.45 (d, J=7.85 Hz, 2H), 7.37 (d, J=8.45 Hz, 1H), 6.44 (d, J=7.66 Hz, 1H), 5.05-5.00 (m, 1H), 4.93 (t, J=5.66 Hz, 1H), 3.92 (s, 2H), 3.67-3.51 (m, 2H), 2.22 (s, 3H), 1.28 (d, J=7.51 Hz, 3H).

Method J

Compound 29

2-(3-Fluoro-4-trifluoromethyl-phenyl)-N-((S)-6-methyl-1-oxo-2-pyrrolidin-3-yl-1,2-dihydro-isoquinolin-5-yl)-acetamide

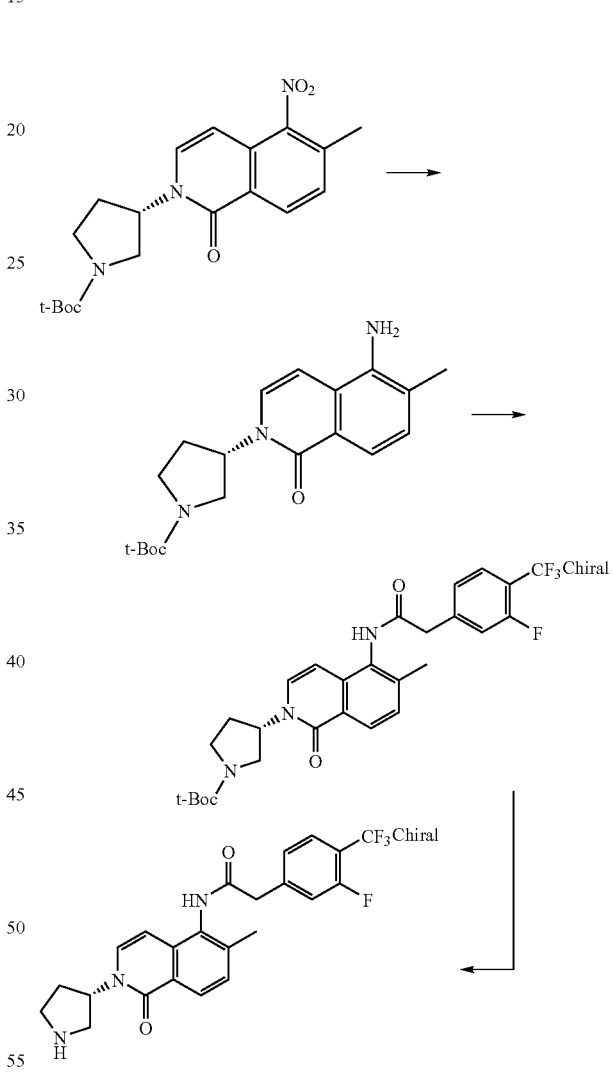

a. (S)-tert-Butyl 3-(5-amino-6-methyl-1-oxoisoquinolin-2(1H)-yl)pyrrolidine-1-carboxylate A round bottom flask was charged with (S)-tert-butyl 3-(6-methyl-5-nitro-1-oxoisoquinolin-2(1H)-yl)pyrrolidine-1-carboxylate (500.0 mg, 0.001339 mol), ethanol (5 mL, 0.08 mol) and ammonium chloride (716.3 mg, 0.01339 mol) in water (3 mL, 0.2 mol) was added at 85° C. Iron (299 mg, 0.00536 mol) was added in portions and was stirred at that temperature for 30 minutes, poured onto methylene chloride (50 mL) and extracted. The solvent was removed under reduced pressure to afford the pure product as light yellow solid.

b. (S)-tert-Butyl 3-(5-(2-(3-fluoro-4-(trifluoromethyl)phenyl)acetamido)-6-methyl-1-oxoisoquinolin-2(1H)-yl)pyrrolidine-1-carboxylate A reaction vial was charged with (S)-tert-butyl 3-(5-amino-6-methyl-1-oxoisoquinolin-2(1H)-yl)pyrrolidine-1-carboxylate (150.00 mg, 0.043678 mmol), 2-(3-fluoro-4-(trifluoromethyl)phenyl)acetic acid (116.4 mg, 0.05241 mmol), N,N,N',N'-tetramethyl-O-(7-azabenzotriazol-1-yl)uronium hexafluorophosphate (420 mg, 1.1 mmol), N,N-diisopropylethylamine (0.19 mL, 1.1 mmol) and N,N-dimethylformamide (2 mL, 20 mmol) and the reaction was stirred at 45° C. overnight. The solvent was removed under reduced pressure and the residue purified by flash chromatography to afford the product as light yellow oil.

c. (S)-2-(3-fluoro-4-(trifluoromethyl)phenyl)-N-(6-methyl-1-oxo-2-(pyrrolidin-3-yl)-1,2-dihydroisoquinolin-5-yl)acetamide A round bottom flask was charged with (S)-tert-butyl 3-(5-(2-(3-fluoro-4-(trifluoromethyl)phenyl)acetamido)-6-methyl-1-oxoisoquinolin-2(1H)-yl)pyrrolidine-1-carboxylate (100.0 mg, 0.0001826 mol), methylene chloride (3 mL, 0.05 mol) and 2M hydrochloric acid in ether (4 mL) was added and the reaction was stirred at 45° C. for 3 hours. The solvent was removed under reduced pressure under reduced pressure and the residue was purified by reverse phase preparative HPLC to afford the product as white solid.

MS m/z=448.3 (M+H)

$^1$H NMR (400 MHz; DMSO-d6) δ9.92 (s, 1H), 8.08 (d, J=8.79 Hz, 1H), 7.79 (t, J=8.16 Hz, 1H), 7.55-7.51 (m, 2H), 7.44 (d, J=8.16 Hz, 1H), 7.38 (d, J=8.79 Hz, 1H), 6.49 (d, J=6.90 Hz, 1H), 5.34-5.31 (m, 1H), 3.92 (s, 2H), 3.14-3.05 (m, 2H), 2.90-2.78 (m, 2H), 2.22 (s, 3H), 2.22-2.19 (m, 1H), 2.00-1.98 (m, 1H), 1.72-1.68 (m, 1H).

Method K

Compound 31

2-Adamantan-1-yl-N-[2-((R)-2-hydroxy-1-methyl-ethyl)-6-methyl-1-oxo-1,2-dihydro-isoquinolin-5-yl]-acetamide

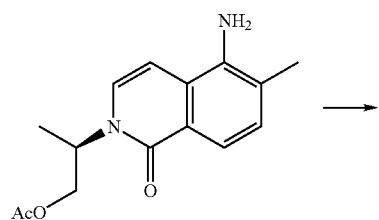

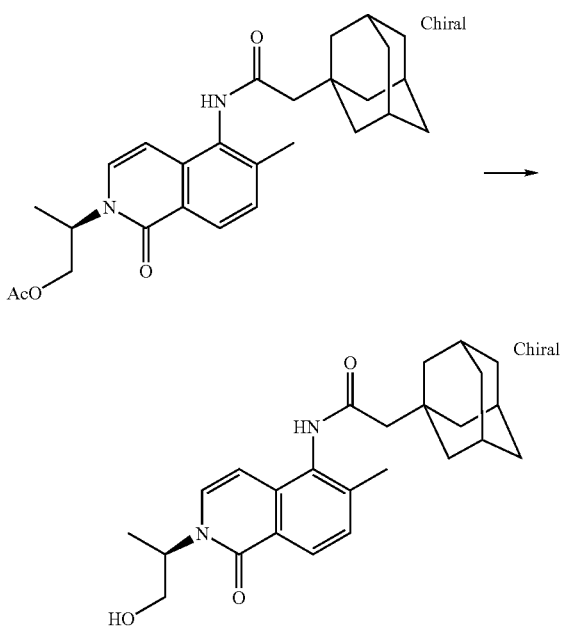

a. Acetic acid (R)-2-[5-(2-adamantan-1-yl-acetylamino)-6-methyl-1-oxo-1H-isoquinolin-2]-propyl ester A round bottom flask was charged with (R)-2-(5-amino-6-methyl-1-oxoisoquinolin-2(1H)-yl)propyl acetate (150.0 mg, 0.0005468 mol), 1-adamantaneacetic acid (127 mg, 0.000656 mol), N,N,N',N'-tetramethyl-O-(7-azabenzotriazol-1-yl)uronium hexafluorophosphate (520 mg, 0.00137 mol), N,N-diisopropylethylamine (0.238 mL, 0.00137 mol), N,N-dimethylformamide (3 mL, 0.04 mol), methylene chloride (10 mL, 0.2 mol) and the reaction was stirred at 45° C. for 3 days. The solvent was removed under reduced pressure and the residue purified by reverse phase prep HPLC to afford the product as a white solid.

b. (R)-2-Adamantyl-N-(2-(1-hydroxypropan-2-yl)-6-methyl-1-oxo-1,2-dihydroisoquinolin-5-yl)acetamide A round bottom flask was charged with acetic acid (R)-2-[5-(2-adamantan-1-yl-acetylamino)-6-methyl-1-oxo-1H-isoquinolin-2-yl]-propyl ester (120.00 mg, 0.26633 mmol), potassium carbonate (110.00 mg, 0.000799 mol), methanol (10 mL, 0.3 mol) and a few drops of methanol. The reaction mixture was stirred at room temperature for 1 hour. The mixture was filtered and the solvent removed under reduced pressure. The residue was extracted with (chloroform:IPA 3:1) and the solvent was removed under reduced pressure to afford the product as a light yellow solid.

MS m/z=409.5 (M+H)

$^1$H NMR (400 MHz; DMSO-d6) δ9.50 (s, 1H), 8.06 (d, J=8.54 Hz, 1H), 7.48 (d, J=7.93 Hz, 1H), 7.37 (d, J=7.93 Hz, 1H), 6.49 (d, J=8.54 Hz, 1H), 5.05-5.00 (m, 1H), 4.94 (bs, 1H), 3.64-3.59 (m, 2H), 2.28 (s, 3H), 2.18 (s, 2H), 1.97 (m, 3H), 1.71-1.61 (m, 12H), 1.27 (d, J=7.06, 3H).

Method L

Compound 32

2-Cycloheptyl-N-[2-((R)-2-hydroxy-1-methyl-ethyl)-6-methyl-1-oxo-1,2-dihydro-isoquinolin-5-yl]-acetamide

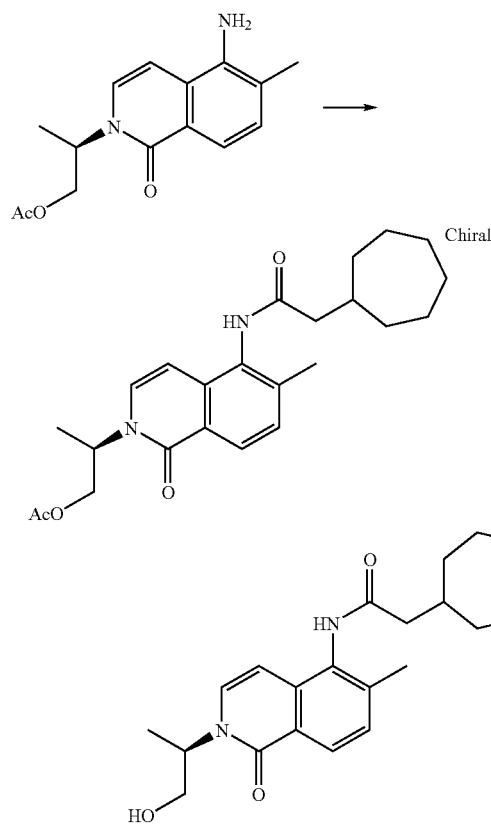

a. (R)-2-(5-(2-Cycloheptylacetamido)-6-methyl-1-oxoisoquinolin-2(1H)-yl)propyl acetate A round bottom flask was charged with (R)-2-(5-amino-6-methyl-1-oxoisoquinolin-2(1H)-yl)propyl acetate (150.00 mg, 0.054682 mmol), N,N,N',N'-tetramethyl-O-(7-azabenzotriazol-1-yl)uronium hexafluorophosphate (520.00 mg, 0.00137 mol), N,N-diisopropylethylamine (0.238 mL, 0.00137 mol), N,N-dimethylformamide (3 mL, 0.04 mol), methylene chloride (10 mL, 0.2 mol). The reaction mixture stirred at 45° C. for 3 days. Water was added and extracted with ethyl acetate. The ethyl acetate layer was separated and the solvent was removed under reduced pressure. The residue was purified by flash chromatography to afford the product as white solid.

b. (R)-2-Cycloheptyl-N-(2-(1-hydroxypropan-2-yl)-6-methyl-1-oxo-1,2-dihydroisoquinolin-5-yl)acetamide A round bottom flask was charged with (R)-2-(5-(2-cycloheptylacetamido)-6-methyl-1-oxoisoquinolin-2(1H)-yl)propyl acetate (180.0 mg, 0.0004363 mol), potassium carbonate (180 mg, 0.0013 mol), methanol (15 mL, 0.37 mol) and few drops of water. The reaction mixture was stirred at room temperature for 1 hour. The solvent was removed under reduced pressure and water was added to the residue and extracted with (chloroform:IPA, 3:1) and the solvent removed under reduced pressure and the residue purified by reverse phase prep BPLC to afford the product as a white solid.

MS m/z=371.3 (M+H)

$^1$H NMR (400 MHz; DMSO-d6) δ9.57 (s, 1H), 8.06 (d, J=8.33 Hz, 1H), 7.47 (d, J=7.95 Hz, 1H), 7.37 (d, J=8.71 Hz, 1H), 6.44 (d, J=7.96 Hz, 1H), 5.08-5.05 (m, 1H), 4.93 (t, J=5.43 Hz, 1H), 3.67-3.55 (m, 2H), 2.33 (d, J=7.42 Hz, 2H), 2.26 (s, 3H), 2.05 (m, 1H), 1.81-1.76 (m, 2H), 1.66-1.41 (m, 8H), 1.34-1.31 (m, 2H), 1.27 (d, J=6.97, 3H).

Method M

Compound 33

(S)-2-(3-fluoro-4-(trifluoromethyl)phenyl)-N-(2-(1-hydroxypropan-2-yl)-6-methyl-1-oxo-1,2-dihydroisoquinolin-5-yl)acetamide

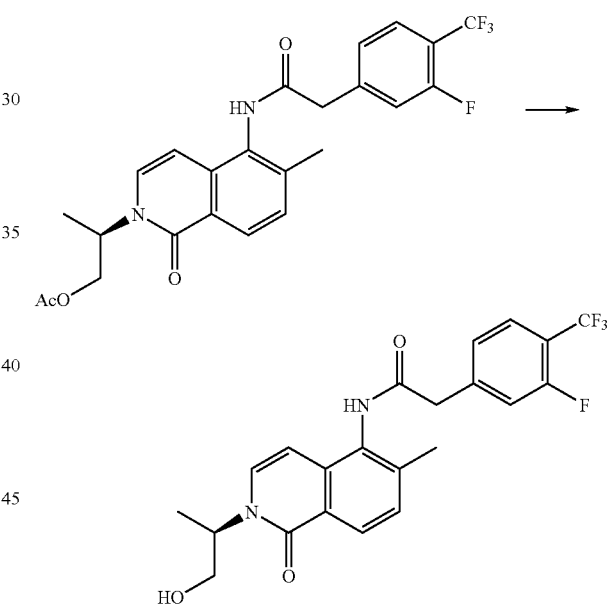

A round bottom flask was charged with (S)-2-(5-(2-(3-fluoro-4-(trifluoromethyl)phenyl)-acetamido)-6-methyl-1-oxoisoquinolin-2(1H)-yl)propyl acetate (200.00 mg, 0.41803 mmol), potassium carbonate (173 mg, 0.00125 mol), methanol (15 mL, 0.37 mol) and few drops of water. The reaction was stirred at room temperature for 1 h. The reaction mixture was filtered and the solvent was removed under reduced pressure. The residue was extracted with IPA:chloroform, 1:3, washed with water and the solvent was removed under reduced pressure. The residue was purified by reverse phase prep HPLC to give the desired compound as light orange solid.

MS m/z=437.5 (M+H).

$^1$H NMR (400 MHz, DMSO-d$_6$): δ9.92 (s, 1H), 8.07 (d, J=8.33 Hz, 1H), 7.79 (t, J=7.64 Hz, 1H), 7.53 (d, J=13.20 Hz, 1H), 7.45 (d, J=7.64 Hz, 2H), 7.37 (d, J=8.33 Hz, 1H), 6.44 (d,

J=8.33 Hz, 1H), 5.04-5.00 (m, 1H), 4.93 (t, J=5.25 Hz, 1H), 3.92 (s, 2H), 3.67-3.55 (m, 2H), 2.22 (s, 3H), 1.27 (d, J=7.47 Hz, 3H).

Method N

Compound 37

2-(1-Hydroxy-cycloheptyl)-N-[2-((R)-2-hydroxy-1-methyl-ethyl)-6-methyl-1-oxo-1,2-dihydroisoquinolin-5-yl]-acetamide

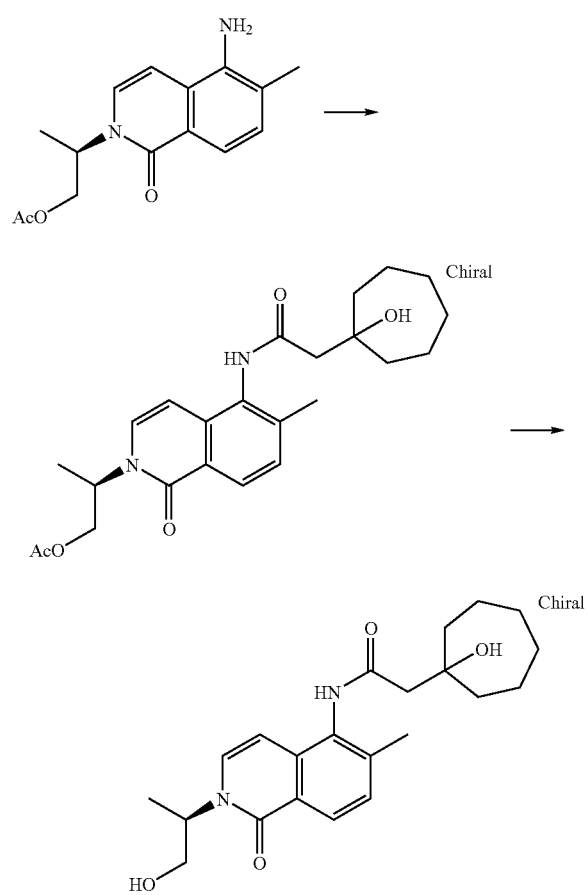

a. (R)-2-(5-(2-(1-Hydroxycycloheptyl)acetamido)-6-methyl-1-oxoisoquinolin-2(1H)-yl)propyl acetate A round bottom flask was charged with (R)-2-(5-amino-6-methyl-1-oxoisoquinolin-2(1H)-yl)propyl acetate (100.00 mg, 0.36454 mmol), 2-(1-hydroxycycloheptyl)acetic acid (75.3 mg, 0.437 mmol), N,N,N',N'-tetramethyl-O-(7-azabenzotriazol-1-yl)uronium hexafluorophosphate (346 mg, 0.911 mmol), N,N-diisopropylethylamine (0.159 mL, 0.911 mmol), N,N-dimethylformamide (2 mL, 30 mmol) and methylene chloride (8 mL, 100 mmol). The reaction mixture was stirred at room temperature overnight. The solvent was removed under reduced pressure and the residue was taken onto the next step without further purification.

b. (R)-2-(1-Hydroxycycloheptyl)-N-(2-(1-hydroxypropan-2-yl)-6-methyl-1-oxo-1,2-dihydroisoquinolin-5-yl)acetamide A round bottom flask was charged with (R)-2-(5-(2-(1-hydroxycycloheptyl)acetamido)-6-methyl-1-oxoisoquinolin-2(1H)-yl)propyl acetate (100.00 mg, 0.14 mmol), potassium carbonate (58.0 mg, 0.000420 mol) and methanol (4 mL, 0.1 mol) and the reaction mixture stirred at room temperature 1 hour. The solvent was removed under reduced pressure and the residue was purified by reverse phase preparative HPLC to afford the product.

MS m/z=387.4 (M+H).

$^1$H NMR (400 MHz, CDCl$_3$): δ8.44 (s, 1H), 7.95 (d, J=8.3875 Hz, 1H), 7.06-7.04 (m, 2H), 6.34 (d, J=7.74 Hz, 1H), 5.10-5.06 (m, 1H), 3.80-3.67 (m, 2H), 3.47 (s, 1H), 2.59 (s, 2H), 2.21 (s, 3H), 1.87-1.39 (m, 13H), 1.33 (d, J=7.10 Hz, 3H)

Method O

Compound 38

2-(3-Fluoro-4-trifluoromethyl-phenyl)-1-[6-methyl-2-(2-methylamino-ethyl)-1-oxo-1,2-dihydroisoquinolin-5-yl]-acetamide

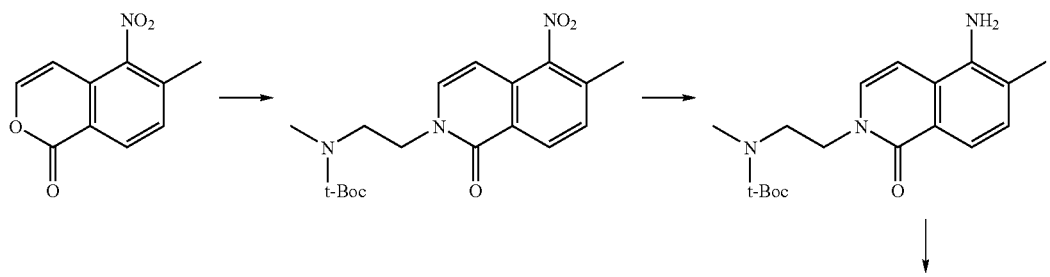

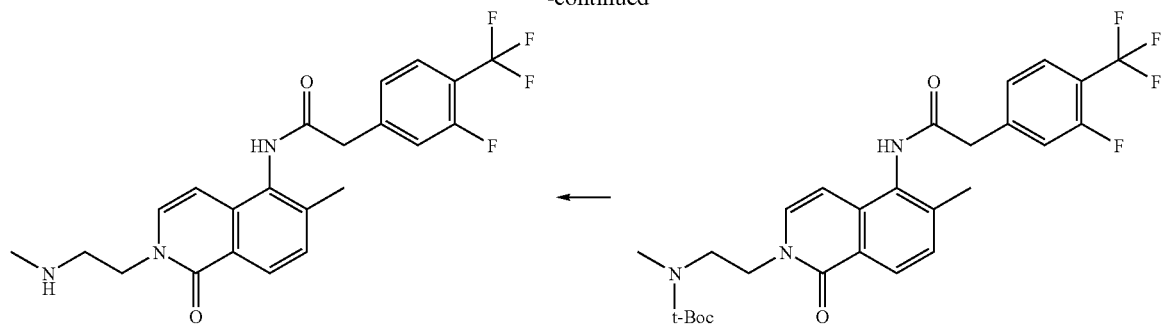

a. tert-Butyl methyl(2-(6-methyl-5-nitro-1-oxoisoquinolin-2(1H)-yl)ethyl)carbamate A microwave vial was charged with 6-methyl-5-nitro-1H-isochromen-1-one (270 mg, 0.0012 mol), tert-butyl 2-aminoethylmethylcarbamate (400 mg, 0.002 mol), triethylamine (0.6 mL, 0.005 mol) and methanol (5 mL, 0.1 mol) and the reaction was heated at 100° C. for 1.5 hours. The solvents were removed under reduced pressure and the residue was purified by flash chromatography to afford the desired product as a brown oil.
MS m/z=362.0 (M+H)$^+$.

b. tert-Butyl 2-(5-amino-6-methyl-1-oxoisoquinolin-2(1H)-yl)ethyl(methyl)carbamate A round bottom flask was charged with tert-butyl methyl (2-(6-methyl-5-nitro-1-oxoisoquinolin-2(1H)-yl)ethyl)carbamate (110 mg, 0.00031 mol) and ethanol (5 mL, 0.08 mol), and the solution was heated at 85° C. Ammonium chloride (300 mg, 0.006 mol) in water (2 mL, 0.09 mol) was added followed by iron (200 mg, 0.003 mol) in two portions. The reaction was stirred for 1 hour and poured onto dichloromethane (200 mL) and extracted. The solvent was removed under reduced pressure and the residue was purified by flash chromatography. to afford the desired product as a yellow oil.
MS m/z=332.2 (M+H)$^+$.

c. tert-Butyl 2-(5-(2-(3-fluoro-4-(trifluoromethyl)phenyl)acetamido)-6-methyl-1-oxoisoquinolin-2(1H)-yl)ethyl(methyl)carbamate A reaction vial was charged with tert-butyl 2-(5-amino-6-methyl-1-oxoisoquinolin-2(1H)-yl)ethyl(methyl)carbamate (150 mg, 0.00041 mol), 2-(3-fluoro-4-(trifluoromethyl)phenyl)acetic acid (200 mg, 0.0009 mol), N,N,N,N',N'-tetramethyl-O-(7-azabenzotriazol-1-yl)uronium hexafluorophosphate (700 mg, 0.002 mol), N,N-diisopropylethylamine (0.3 mL, 0.002 mol), N,N-dimethylformamide (4 mL, 0.05 mol) and the reaction was stirred at 45° C. overnight. The reaction was then quenched with water, extracted with warm ethyl acetate, and the solvent removed under reduced pressure. The residue was purified by flash chromatography and then by reversed phase preparative HPLC to afford the product as an off white solid.
MS m/z=536.3 (M+H)$^+$.
$^1$H NMR (400 MHz, CD$_3$OD) δ 8.13 (d, J=8.3 Hz, 1H), 7.63 (t, J=7.8 Hz, 1H), 7.37-7.35 (m, 3H), 7.14 (d, J=7.6 Hz, 1H), 6.46 (d, J=7.4 Hz, 1H), 4.07-4.02 (m, 2H), 3.86 (s, 2H), 3.62-3.57 (m, 2H), 2.23 (s, 3H), 1.96 (s, 3H), 0.98 (s, 9H).

d. 2-(3-Fluoro-4-(trifluoromethyl)phenyl)-N-(6-meth-2-(2-(methylamino)ethyl)-1-oxo-1,2-dihydroisoquinolin-5-yl)acetamide tert-Butyl 2-(5-(2-(3-fluoro-4-(trifluoromethyl)phenyl) acetamido)-6-methyl-1-oxoisoquinolin-2(1H)-yl)ethyl(methyl)carbamate (79 mg, 0.00015 mol) was dissolved in methanol (3 mL, 0.07 mol), and 3N hydrochloric acid (1 mL) was added. The mixture was stirred at room temperature overnight. An additional 2 mL of 3N hydrochloric acid and 3 mL of concentrated hydrochloric acid, weres added and the mixture was stirred at room temperature overnight. The volatiles were removed under reduced pressure and the residue was purified by flash chromatography and then by reverse phase preparative HPLC to afford the desired product as a white solid.
MS m/z=436.1 (M+H)$^+$.
$^1$H NMR (400 MHz CD$_3$OD) δ 8.21 (d, J=8.3 Hz, 1H), 7.72 (t, J=7.9 Hz, 1H), 7.47-7.44 (m, 3H), 7.36 (d, J=7.6 Hz, 1H), 6.57 (d, J=7.6 Hz, 1H), 4.16 (t, J=6.5 Hz, 2H), 3.96 (s, 2H), 2.94 (t, J=6.5 Hz, 2H), 2.42 (s, 3H), 2.32 (s, 3H).

Method P

Compound 40

2-((R)-2-Hydroxy-1-methyl-ethyl)-6-methyl-1-oxo-1,2-dihydro-isoquinoline-5-carboxylic acid 3-fluoro-4-trifluoromethyl-benzylamide

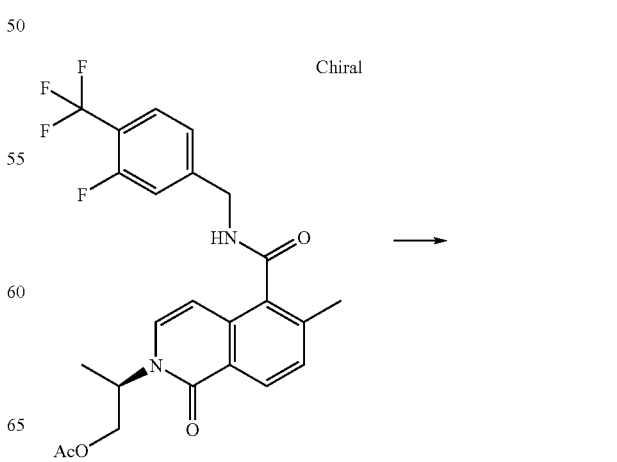

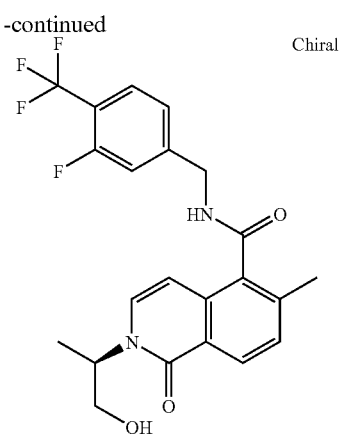

a. (R)—N-(3-Fluoro-4-(trifluoromethyl)benzyl)-2-(1-hydroxypropan-2-yl)-6-methyl-1-oxo-1,2-dihydroisoquinolin-5-carboxamide A round bottom flask was charged with (R)-2-(5-(3-fluoro-4-(trifluoromethyl)benzyl-carbamoyl)-6-methyl-1-oxoisoquinolin-2(1H)-yl)propyl acetate (0.47 g, 0.00093 mol), potassium carbonate (0.22 g, 0.0016 mol) and methanol (100 mL, 2 mol). The reaction was stirred at room temperature for 1 hour. The solvent was removed under reduced pressure and the residue was purified by reverse phase HPLC to afford the desired product as a an off white solid.

MS m/z=437.3 (M+H)$^+$.

$^1$H NMR (400 MHz, CD$_3$OD) δ 8.29 (d, J=8.3 Hz, 1H), 7.74 (t, J=7.5 Hz, 1H), 7.51-7.42 (m, 4H), 6.55 (d, J=7.8 Hz, 1H), 5.21-5.16 (m, 1H), 4.72 (s, 2H), 3.86-3.76 (m, 2H), 2.46 (s, 3H), 1.42 (d, J=7.0 Hz, 3H).

Method Q

Compound 41

6-Chloro-2-((R)-2-hydroxy-1-methyl-ethyl)-1-oxo-1,2-dihydro-isoquinoline-5-carboxylic acid 3-fluoro-4-trifluoromethyl-benzylamide

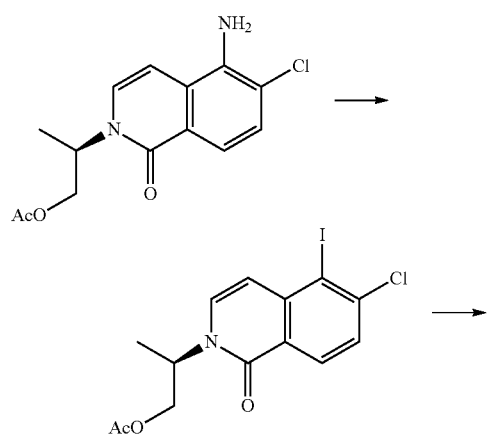

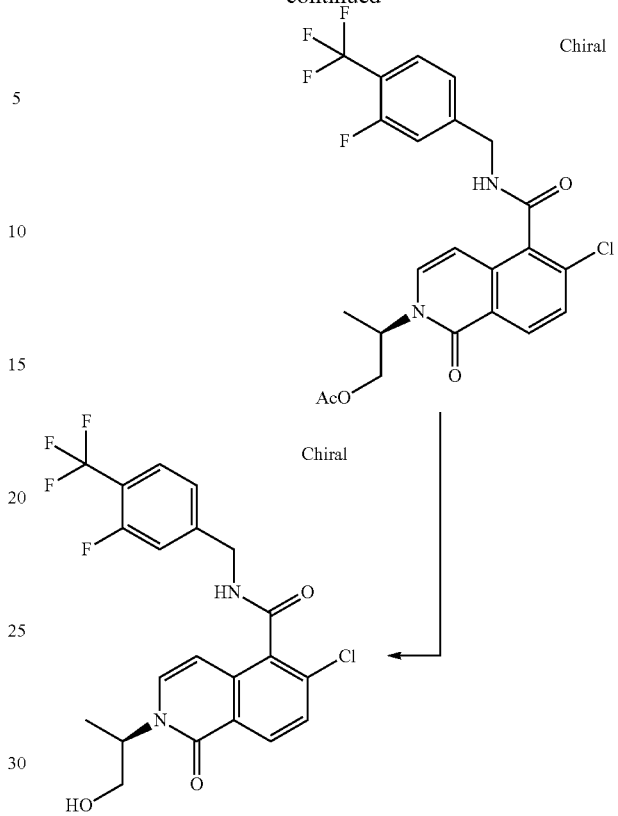

a. (R)-2-(6-Chloro-5-iodo-1-oxoisoquinolin-2(1H)-yl)propyl acetate

To a solution of sodium nitrite (1 g, 0.02 mol), hexamethyldisilane (3 g, 0.02 mol), iodine (5 g, 0.02 mol) and benzyltriethylammonium chloride (0.3 g, 0.001 mol) in carbon tetrachloride (100 mL, 1 mol) was added a solution of (R)-2-(5-amino-6-chloro-1-oxoisoquinolin-2(1H)-yl)propyl acetate (2.3 g, 0.0070 mol) in methylene chloride (3 mL, 0.05 mol) at 0° C. The mixture was stirred at the same temperature for 40 minutes and then warmed to room temperature overnight. The mixture was purified by flash chromatography to afford the desired product as a brown oil.

MS m/z=406.0 (M+H)$^+$.

b. (R)-2-(6-Chloro-5-(3-fluoro-4-(trifluoromethyl)benzylcarbamoyl)-1-oxoisoquinolin-2(1H)-yl)propyl acetate A 5 mL process vial was charged with (R)-2-(6-chloro-5-iodo-1-oxoisoquinolin-2(1H)-yl)propyl acetate (200 mg, 0.0005 mol) 3-fluoro-4-trifluoromethyl-benzylamine (200 mg, 0.0009 mol), molybdenum hexacarbonyl (100 mg, 0.0005 mol), palladium acetate (10 mg, 0.00005 mol), 1,8-diazabicyclo[5.4.0]undec-7-ene (300 mg, 0.002 mol) and 1,4-dioxane (3 mL, 0.04 mol). The vessel was sealed under air and exposed to microwave irradiation at 110° C. for 15 min, cooled to room temperature, and concentrated The residue was purified by flash chromatography to afford the desired product as a clear oil.

MS m/z=499.5 (M+H)$^+$.

$^1$H NMR (400 MHz, CDCl$_3$, δ 8.38 (d, J=8.6 Hz, 1H), 7.63 (t, J=7.8 Hz, 1H), 7.44 (d, J=8.7 Hz, 1H), 7.33-7.30 (m, 2H), 7.20 (d, J=7.8 Hz, 1H), 6.51 (d, J=7.8 Hz, 1H), 6.50-6.36 (m, 1H), 5.43-5.38 (m, 1H), 4.78 (d, J=6.3 Hz, 2H), 4.32-4.30 (m, 2H), 2.01 (s, 3H), 1.45 (d, J=7.2 Hz, 3H).

c. (R)-6-Chloro-N-(3-fluoro-4-(trifluoromethyl)benzyl)-2-(1-hydroxypropan-2-yl)-1-oxo-1,2-dihydroisoquinoline-5-carboxamide A round bottom flask was charged with (R)-2-(6-chloro-5-(3-fluoro-4-(trifluoromethyl)benzylcarbamoyl)-1-oxoisoquinolin-2(1H)-yl)propyl acetate (120 mg, 0.00022 mol), potassium carbonate (100 mg, 0.0007 mol) and methanol (7 mL, 0.2 mol). The reaction was stirred at room temperature for 1 hour. The solvent was removed under reduced pressure and the residue was purified by reverse phase preparative HPLC to afford the desired product as a white solid.

MS m/z=457.2 (M+H)⁺.

¹H NMR (400 MHz, CD₃OD) δ 8.38 (d, J=8.7 Hz, 1H), 7.73 (t, J=8.0 Hz, 1H), 7.59 (d, J=8.0 Hz, 2H), 7.48-7.44 (m, 2H), 6.55 (d, J=7.7 Hz, 1H), 5.21-5.16 (m, 1H), 4.74 (s, 2H), 3.86-3.77 (m, 2H), 1.42 (d, J=7.0 Hz, 3H).

Method R

Compound 47

6-Chloro-2-((R)-2-hydroxy-1-methyl-ethyl)-1-oxo-1,2-dihydro-isoquinoline-5-carboxylic acid (1-hydroxy-cycloheptylmethyl)-amide

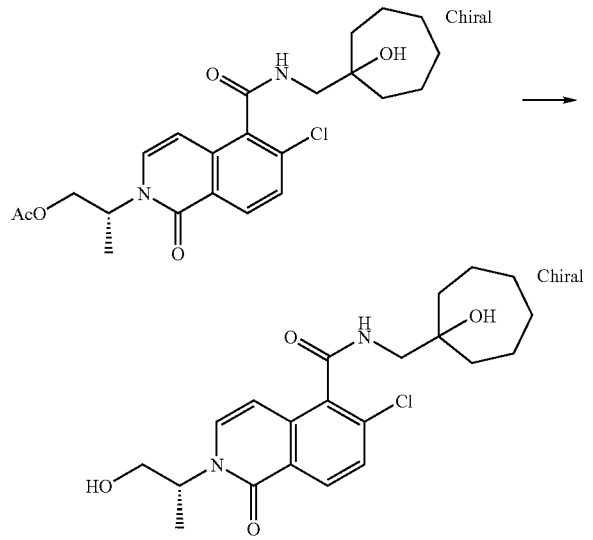

a. (R)-6-Chloro-N-((1-hydroxycycloheptyl)methyl)-2-(1-hydroxypropan-2-yl)-1-oxo-1,2-dihydroisoquinoline-5-carboxamide A mixture of (R)-2-(6-Chloro-5-((1-hydroxycycloheptyl)methylcarbamoyl)-1-oxoisoquinolin-2(1H)-yl)propyl acetate (620 mg, 0.0012 mol) and potassium carbonate (300 mg, 0.002 mol) was stirred in methanol (50 mL, 1 mol) at room temperature for 1 h. The mixture was concentrated, and the residue was purified by reverse phase preparative HPLC and then by flash chromatography to afford the desired product as a white solid.

MS m/z=387.5 (M+H)⁺.

¹H NMR (400 MHz, CDCl₃) δ 8.36 (d, J=8.7 Hz, 1H), 7.44 (d, J=8.7 Hz, 1H), 7.26 (d, J=7.7 Hz, 1H), 6.61 (d, J=7.8 Hz, 1H), 6.33 (br, 1H), 5.18-5.12 (m, 1H), 3.92 (dd, J=3.8, 11.7 Hz, 1H), 3.84 (dd, J=4.6, 11.4 Hz, 1H), 3.55 (d, J=6.0 Hz, 2H), 2.09-1.49 (m, 12H), 1.45 (d, J=7.2 Hz, 3H).

Method S

Compound 53

6-Chloro-2-((R)-2-hydroxy-1-methyl-ethyl)-1-oxo-1,2-dihydro-isoquinoline-5-carboxylic acid (2-hydroxy-bicyclo[2.2.1]hept-2-ylmethyl)-amide

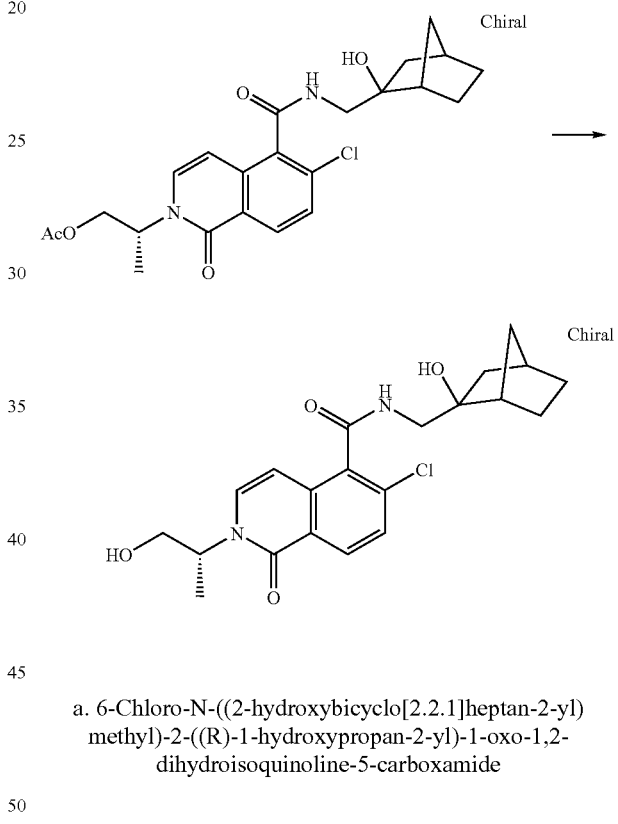

a. 6-Chloro-N-((2-hydroxybicyclo[2.2.1]heptan-2-yl)methyl)-2-((R)-1-hydroxypropan-2-yl)-1-oxo-1,2-dihydroisoquinoline-5-carboxamide A mixture of (2R)-2-(6-chloro-5-((2-hydroxybicyclo[2.2.1]heptan-2-yl)methylcarbamoyl)-1-oxoisoquinolin-2(1H)-yl)propyl acetate (31 mg, 0.000042 mol) and potassium carbonate (23 mg, 0.00017 mol) was stirred in methanol (3 mL, 0.07 mol) at room temperature for 1 hour and concentrated. The residue was purified by reverse phase preparative HPLC and then by flash chromatography to afford a white solid.

MS m/z=405.3 (M+H)⁺.

¹H NMR (400 MHz, CD₃OD) δ 8.36 (d, J=8.6 Hz, 1H), 7.62-7.57 (m, 2H), 6.69 (d, J=7.7 Hz, 1H), 5.21-5.16 (m, 1H), 3.86-3.77 (m, 2H), 3.54 (dd, J=16.9, 25.9 Hz, 2H), 2.33-2.25 (m, 2H), 2.07-2.04 (m, 1H), 1.93-1.91 (m, 1H), 1.84-1.60 (m, 2H), 1.43-1.39 (m, 6H), 1.18-1.15 (m, 2H).

Method T

Compound 54

(R)-6-chloro-N-((1-hydroxy-4,4-dimethylcyclohexyl)methyl)-2-(1-hydroxypropan-2-yl)-1-oxo-1,2-dihydroisoquinoline-5-carboxamide

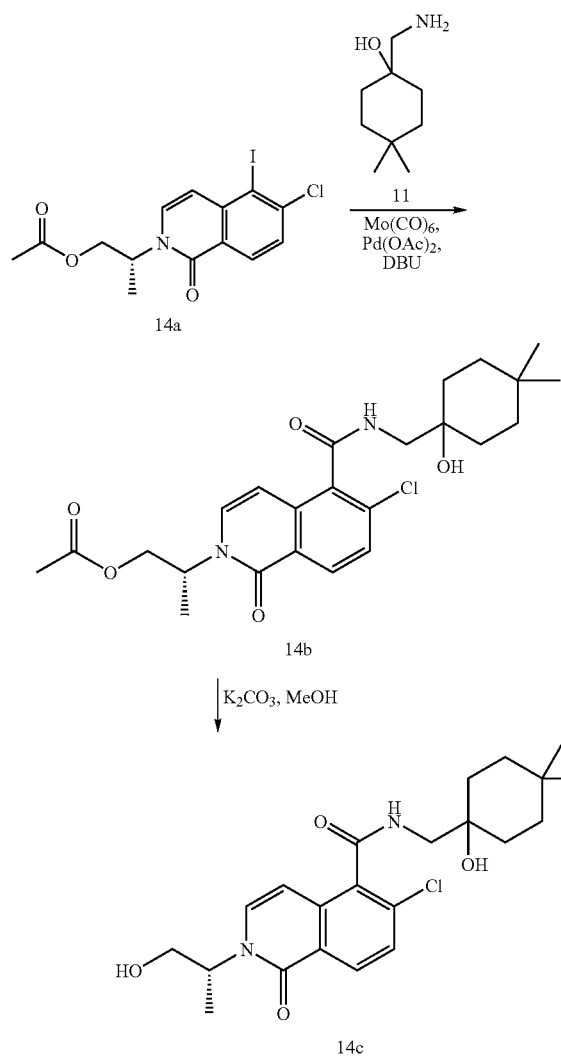

a. (R)-6-Chloro-N-((1-hydroxy-4,4-dimethylcyclohexyl)methyl)-2-(1-hydroxypropan-2-yl)-1-oxo-1,2-dihydroisoquinoline-5-carboxamide (14b)

This compound was synthesized following the same synthetic method as for (R)-2-(6-chloro-5-((4,4-difluorocyclohexyl)methylcarbamoyl)-1-oxoisoquinolin-2(1H)-yl)propyl acetate (18b, see Compound 61).

MS m/z=463.2. (M+H).

$^1$H NMR (400 MHz, CDCl$_3$) δ 8.20 (d, J=8.7 Hz, 1H), 7.31 (d, J=8.7 Hz, 1H), 7.18 (d, J=7.8 Hz, 1H), 6.70 (br, 1H), 6.59 (d, J=7.8 Hz, 1H), 5.48-5.40 (m, 1H), 4.31-4.28 (m, 2H), 3.59-3.57 (m, 2H), 2.01 (s, 3H), 1.67-1.20 (m, 14H), 0.85 (d, J=7.2 Hz, 3H).

b. (R)-6-chloro-N-((1-hydroxy-4,4-dimethylcyclohexyl)methyl)-2-(1-hydroxypropan-2-yl)-1-oxo-1,2-dihydroisoquinoline-5-carboxamide (14c)

This compound was synthesized following the same synthetic method as for (R)-6-chloro-N-((4,4-difluorocyclohexyl)methyl)-2-(1-hydroxypropan-2-yl)-1-oxo-1,2-dihydroisoquinoline-5-carboxamide (18c, see Compound 61).

MS m/z=421.4. (M+H).

$^1$H NMR (,400 MHz, CD$_3$OD) δ 8.24 (d, J=8.7 Hz, 1H), 7.46 (d, J=7.5 Hz, 2H), 6.55 (d, J=7.8 Hz, 1H), 5.09-5.04 (m, 1H), 3.75-3.65 (m, 2H), 3.38 (s, 2H), 1.64-1.57 (m, 2H), 1.50-1.44 (m, 4H), 1.30 (d, J=7.0Hz, 3H), 1.19-1.14 (m, 2H), 0.85 (d, J=7.2 Hz, 6H).

Method U

Compound 56

6-Chloro-2-((R)-2-hydroxy-1-methyl-ethyl)-1-oxo-1,2-dihydro-isoquinoline-5-carboxylic acid (1-hydroxy-4-trifluoromethyl-cyclohexylmethyl)-amide

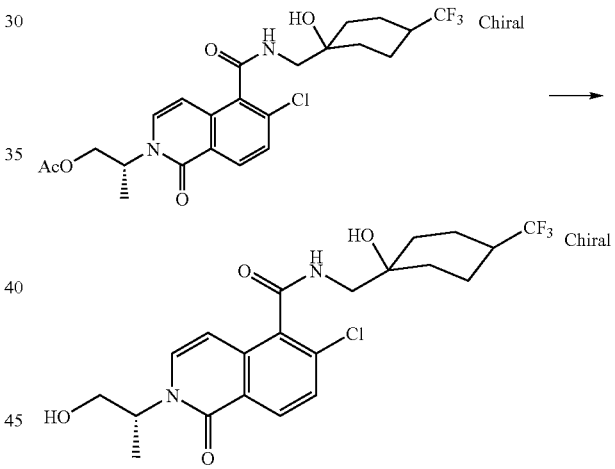

a. (R)-6-Chloro-N-((1-hydroxy-4-(trifluoromethyl)cyclohexyl)methyl)-2-(1-hydroxypropan-2-yl)-1-oxo-1,2-dihydroisoquinoline-5-carboxamide A mixture of (R)-2-(6-chloro-5-((1-hydroxy-4-(trifluoromethyl)cyclohexyl)methylcarbamoyl)-1-oxoisoquinolin-2 (1H)-yl)propyl acetate (76 mg, 0.00014 mol) and potassium carbonate (20 mg, 0.0001 mol) was stirred in methanol (6 mL, 0.1 mol) at room temperature ) at room temperature for 1 hour and concentrated. The residue was purified by reverse phase preparative HPLC to afford a white solid.

MS m/z=461.2 (M+H)$^+$.

$^1$H NMR (400 MHz, DMSO-d6) δ 8.62 (t, J=5.3 Hz, 1H), 8.22 (d, J=9.1 Hz, 1H), 7.60 (d, J=7.8 Hz, 1H), 7.54 (d, J=8.7Hz, 1H), 6.43 (d, J=7.6 Hz, 1H), 5.04-5.02 (m, 1H), 4.96 (t, J=5.3 Hz, 1H), 4.41 (s, 1H), 3.66-3.58 (m, 2H), 3.30 (d,

J=6.1 Hz, 2H), 2.32 (br, 1H), 1.70-1.60 (m, 6H), 1.48-1.44 (m, 2H), 1.27 (d, J=6.9Hz, 3H).

Method V

Compound 58

(R)—N-(2-(1-aminopropan-2-yl)-6-methyl-1-oxo-1,2-dihydroisoquinolin-5-yl)-2-(3-fluoro-4-(trifluoromethyl)phenyl)acetamide

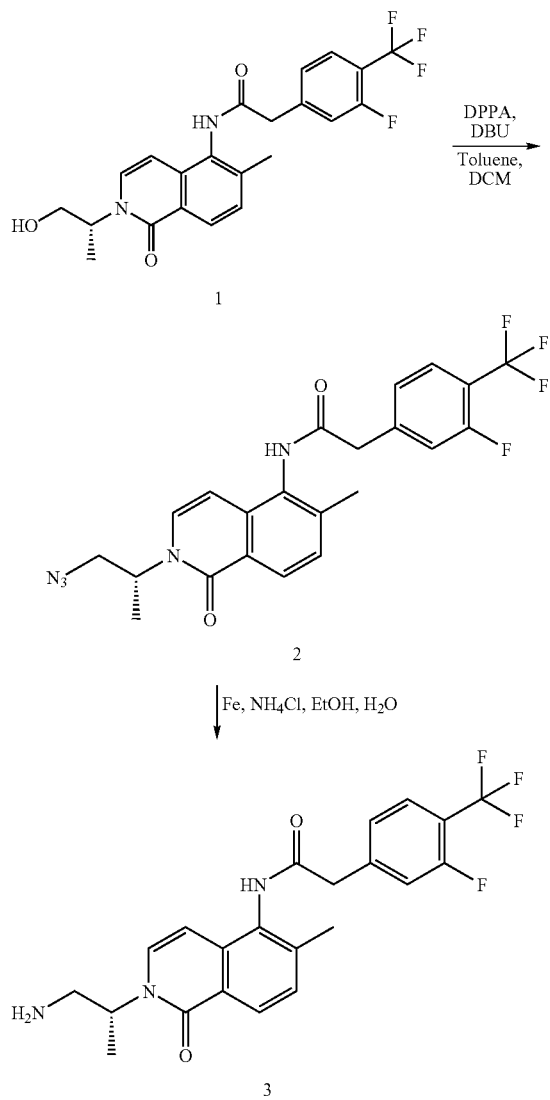

a. (R)—N-(2-(1-Azidopropan-2-yl)-6-methyl-1-oxo-1,2-dihydroisoquinolin-5-yl)-2-(3-fluoro-4-(trifluoromethyl)phenyl)acetamide (2)

A solution of (R)-2-(3-fluoro-4-(trifluoromethyl)phenyl)-N-(2-(1-hydroxypropan-2-yl)-6-methyl-1-oxo-1,2-dihydroisoquinolin-5-yl)acetamide (0.5 g, 0.001 mol) in methylene chloride (20 mL, 0.3 mol) and toluene (10 mL, 0.09 mol) was cooled to 0° C. and treated with diphenylphosphonic azide (600 mg, 0.002 mol), followed by 1,8-diazabicyclo[5.4.0]undec-7-ene (0.3 g, 0.002 mol) under nitrogen. The mixture was stirred at 0° C. for 2 h then allowed to warm to room temperature and was stirred overnight. The mixture was concentrated and the residue was treated with water (50 mL) and ethyl acetate (100 mL). The organic layer was separated, washed with brine, dried and evaporated. The residue was purified via flash chromatography to afford the desired product as a clear oil (0.48 g, yield 90%).

MS m/z=462.3. (M+H)

$^1$H NMR (,400 MHz DMSO-d6) δ 9.94 (s, 1H), 8.08 (d, J=8.2 Hz, 1H), 7.80 (t, J=8.0 Hz, 1H), 7.55-7.49 (m, 2H), 7.45 (d, J=8.0 Hz, 1H), 7.40 (d, J=8.3 Hz, 1H), 6.50 (d, J=7.8 Hz, 1H), 5.20-5.15 (m, 1H), 3.92 (s, 2H), 3.77-3.66 (m, 2H), 2.23 (s, 3H), 1.34 (d, J=7.0 Hz, 3H).

b. (R)—N-(2-(1-Aminopropan-2-yl)-6-methyl-1-oxo-1,2-dihydroisoquinolin-5-yl)-2-(3-fluoro-4-(trifluoromethyl)phenyl)acetamide (3)

A solution of (R)—N-(2-(1-azidopropan-2-yl)-6-methyl-1-oxo-1,2-dihydroisoquinolin-5-yl)-2-(3-fluoro-4-(trifluoromethyl)phenyl)acetamide (0.6 g, 0.001 mol) in ethanol (50 mL, 0.8 mol) was heated at 85° C. A solution of ammonium chloride (0.6 g, 0.01 mol) in water (15 mL, 0.83 mol) was added followed by iron powder (0.6 g, 0.01 mol). The mixture was stirred at the same temperature for 3 hours and poured onto dichloromethane (200 mL) and extracted. The residue was purified by reverse phase HPLC to afford the desired product as a white solid (232 mg, yield 50%).

MS m/z=437.2. (M+H).

$^1$H NMR (400 MHz, DMSO-d6) δ 9.92 (s, 1H), 8.07 (d, J=8.3 Hz, 1H), 7.79 (t, J=8.4 Hz, 1H), 7.53 (d, J=11.9 Hz, 1H), 7.46-7.42 (m, 2H), 7.37 (d, J=8.4 Hz, 1H), 6.46 (d, J=7.5 Hz, 1H), 4.93-4.90 (m, 1H), 3.92 (s, 2H), 2.80 (d, J=7.1 Hz, 2H), 2.22 (s, 3H), 1.27 (d, J=6.92, 3H).

Method W

Compound 59

2-(3-Fluoro-4-trifluoromethyl-phenyl)-N-[6-methyl-2-((R)-1-methyl-2-methylamino-ethyl)-1-oxo-1,2-dihydro-isoquinolin-5-yl]-acetamide

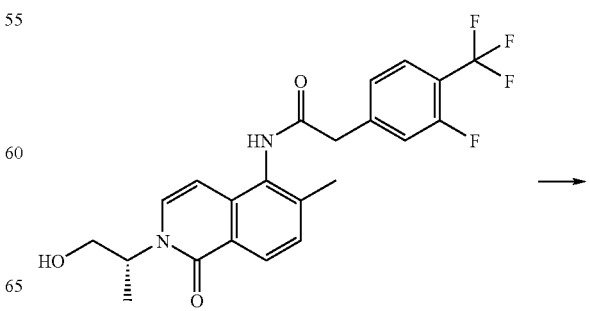

-continued

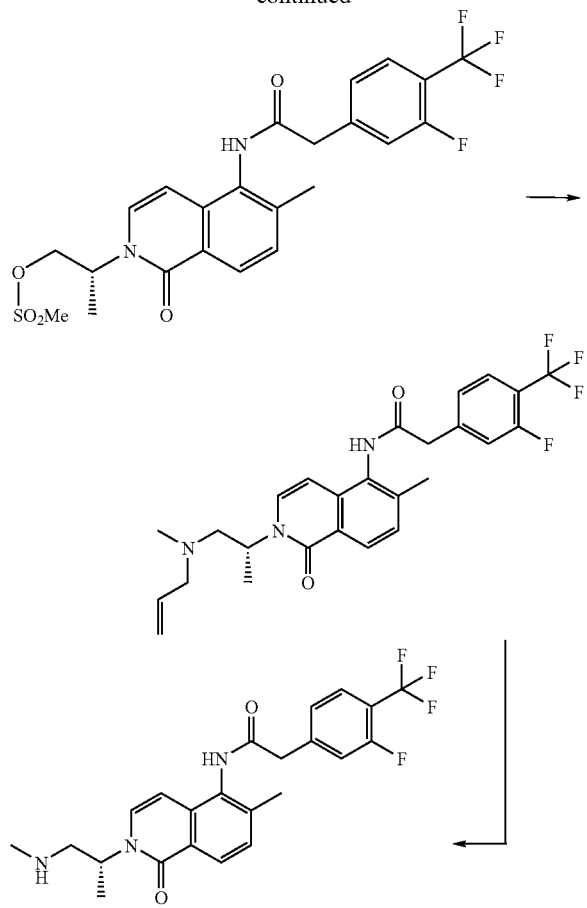

a. (R)-2-(5-(2-(3-Fluoro-4-(trifluoromethyl)phenyl)
acetamido)-6-methyl-1-oxoisoquinolin-2(1H)-yl)
propyl methanesulfonate Triethylamine (0.2 g, 0.002 mol) was added to a solution of (R)-2-(3-fluoro-4-(trifluoromethyl)phenyl)-N-(2-(1-hydroxypropan-2-yl)-6-methyl-1-oxo-1,2-dihydroisoquinolin-5-yl)acetamide (0.5 g, 0.001 mol), methanesulfonyl chloride (0.16 g, 0.0014 mol) and 4-dimethylaminopyridine (10 mg, 0.0001 mol) in methylene chloride (10 mL, 0.2 mol). The mixture was stirred at room temperature overnight. The volatiles were removed under reduced pressure and the mixture was purified via flash chromatography to afford the desired product as a white solid.

b. (R)—N-(2-(1-(Allyl(methyl)amino)propan-2-yl)-
6-methyl-1-oxo-1,2-dihydroisoquinolin-5-yl)-2-(3-
fluoro-4-(trifluoromethyl)phenyl)acetamide A mixture of (R)-2-(5-(2-(3-fluoro-4-(trifluoromethyl)phenyl)acetamido)-6-methyl-1-oxoisoquinolin-2(1H)-yl) propyl methanesulfonate (100 mg, 0.0002 mol), N-methyl-prop-2-en-1-amine (30 mg, 0.4 mmol), triethylamine (200 mg, 0.002 mol) and methylene chloride (6 mL, 0.09 mol) was stirred at room temperature overnight. The volatiles were removed under reduced pressure and the mixture was purified by reverse phase preparative HPLC to afford the desired product as a white solid.

MS m/z=490.0 (M+H)

¹H NMR (,400 MHz DMSO-d6) δ 9.91 (s, 1H), 8.07 (d, J=8.2 Hz, 1H), 7.80 (t, J=8.0 Hz, 1H), 7.53 (d, J=12 Hz, 1H), 7.46-7.36 (m, 3H), 6.47 (d, J=7.7 Hz, 1H), 5.80-5.60 (m, 1H), 5.14-5.10 (m, 1H), 5.07-5.04 (m, 2H), 3.93 (s, 2H), 2.99-2.76 (m, 3H), 2.44-2.39 (m, 1H), 2.22 (s, 3H), 2.11 (s, 3H), 1.26 (d, J=6.8 Hz, 3H).

c. (R)-2-(3-Fluoro-4-(trifluoromethyl)phenyl)-N-(6-
methyl-2-(1-(methylamino)propan-2-yl)-1-oxo-1,2-
dihydroisoquinolin-5-yl)acetamide A solution of (R)—N-(2-(1-(allyl(methyl)amino)propan-2-yl)-6-methyl-1-oxo-1,2-dihydroisoquinolin-5-yl)-2-(3-fluoro-4-(trifluoromethyl)phenyl)acetamide (56 mg, 0.00011 mol) in methylene chloride (2.5 mL, 0.039 mol) was added to 1,3-dimethylbarbituric acid (60 mg, 0.0004 mol) and tetrakis(triphenylphosphine)palladium(0) (1 mg, 0.000001 mol) under argon. The mixture was stirred at room temperature for 4 hours, purified via flash chromatography and then by reverse phase preparative HPLC to afford the desired product as a white solid.

MS m/z=450.4 (M+H)

¹H NMR (400 MHz DMSO-d6) δ 9.92 (s, 1H), 8.07 (d, J=8.2 Hz, 1H), 7.80 (t, J=8.1 Hz, 1H), 7.53 (d, J=12.3 Hz, 1H), 7.46-7.43 (m, 2H), 7.37 (d, J=8.3 Hz, 1H), 6.46 (d, J=7.7 Hz, 1H), 5.15-5.12 (m, 1H), 3.92 (s, 2H), 2.92-2.76 (m, 2H), 2.27 (s, 3H), 2.23 (s, 3H), 1.29 (d, J=7.0 Hz, 3H).

Method X

Compound 60

2-(3-Fluoro-4-trifluoromethyl-phenyl)-N-[6-methyl-
2-((R)-1-methyl-2-piperazin-1-yl-ethyl)-1-oxo-1,2-
dihydro-isoquinolin-5-yl]-acetamide

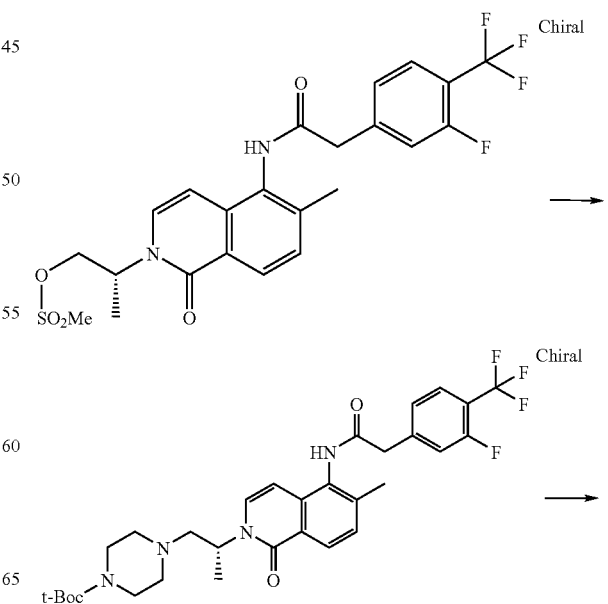

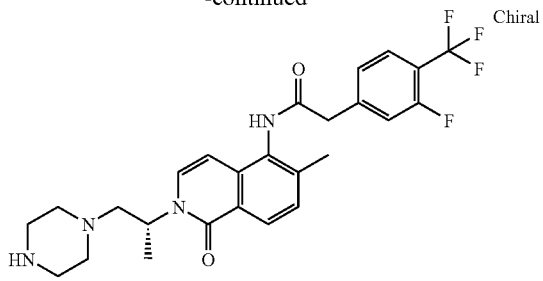

a. (R)-tert-Butyl 4-(2-(5-(2-(3-fluoro-4-(trifluoromethyl)phenyl)acetamido)-6-methyl-1-oxoisoquinolin-2(1H)-yl)propyl)piperazine-1-carboxylate A mixture of (R)-2-(5-(2-(3-fluoro-4-(trifluoromethyl)phenyl)acetamido)-6-methyl-1-oxoisoquinolin-2(1H)-yl)propyl methanesulfonate (100 mg, 0.0002 mol), tert-butyl 1-piperazinecarboxylate (100 mg, 0.0006 mol), triethylamine (200 mg, 0.002 mol) and methylene chloride (6 mL, 0.09 mol) was stirred at room temperature overnight. The solvents were removed under reduced pressure and the residue was purified by flash chromatography to afford the desired product as a light yellow oil (100 mg, 60%).

MS m/z=605.7 (M+H)

b. (R)-2-(3-Fluoro-4-(trifluoromethyl)phenyl)-N-(6-methyl-1-oxo-2-(1-(piperazin-1-yl)propan-2-yl)-1,2-dihydroisoquinolin-5-yl)acetamide To a solution of (R)-tert-butyl 4-(2-(5-(2-(3-fluoro-4-(trifluoromethyl)phenyl)acetamido)-6-methyl-1-oxoisoquinolin-2(1H)-yl)propyl)piperazine-1-carboxylate (100 mg, 0.0002 mol) in methanol (6 mL, 0.1 mol) was added 4M hydrogen chloride in 1,4-dioxane(6 mL, 0.02 mol) at 0° C. The mixture was stirred at room temperature overnight. The volatiles were removed under reduced pressure and the residue was purified by reverse phase preparative HPLC to afford the desired product as a white solid.

MS m/z=505.2 (M+H)

$^1$H NMR (400 MHz DMSO-d6) δ 9.91 (s, 1H), 8.07 (d, J=8.1 Hz, 1H), 7.80 (t, J=7.9 Hz, 1H), 7.54 (d, J=12.6 Hz, 1H), 7.45 (d, J=7.8 Hz, 2H), 7.37 (d, J=8. Hz, 1H), 6.46 (d, J=7.6 Hz, 1H), 5.26-5.20 (m, 1H), 3.93 (s, 2H), 2.72-2.67 (m, 1H), 2.52-2.32 (m, 8H), 2.22 (br, 5H), 1.27 (d, J=6.8 Hz, 3H).

Method Y

Compound 61

(R)-6-Chloro-N-((4,4-difluorocyclohexyl)methyl)-2-(1-hydroxypropan-2-yl)-1-oxo-1,2-dihydroisoquinoline-5-carboxamide

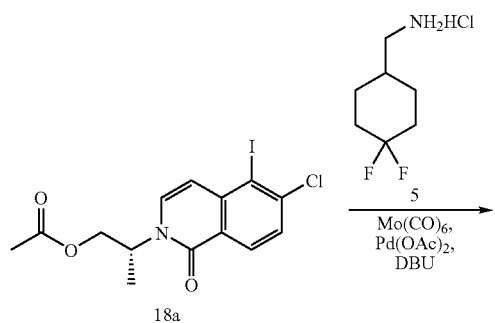

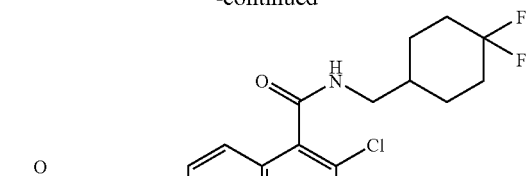

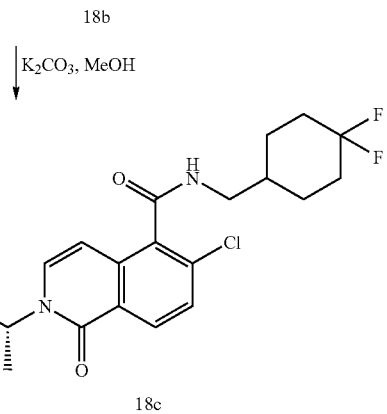

a. (R)-2-(6-Chloro-5-((4,4-difluorocyclohexyl)methylcarbamoyl)-1-oxoisoquinolin-2(1H)-yl)propyl acetate (18b)

A 5 mL process vial was charged with (R)-2-(6-chloro-5-iodo-1-oxoisoquinolin-2(1H)-yl)propyl acetate (18a) (400 mg, 0.0009 mol), (4,4-difluorocyclohexyl)methanamine hydrochloride (150 mg, 0.00081 mol), molybdenum hexacarbonyl (500 mg, 0.002 mol), palladium acetate (15 mg, 0.000067 mol), 1,8-diazabicyclo[5.4.0]undec-7-ene (500 mg, 0.003 mol) and 1,4-dioxane (4 mL, 0.04 mol). The vessel was sealed under air and stirred at 110° C. for 1 hour and cooled to room temperature. The mixture was concentrated and purified by flash chromatography to afford the desired product as a yellow oil. (143 mg, 37%).

MS m/z=455.4 (M+H)

b. (R)-6-Chloro-N-((4,4-difluorocyclohexyl)methyl)-2-(1-hydroxypropan-2-yl)-1-oxo-1,2-dihydroisoquinoline-5-carboxamide (18c)

(R)-2-(6-Chloro-5-((4,4-difluorocyclohexyl)methylcarbamoyl)-1-oxoisoquinolin-2(1H)-yl)propyl acetate (140 mg, 0.00029 mol) and potassium carbonate (140 mg, 0.0010 mol) were stirred in methanol (6 mL, 0.1 mol) at room temperature for 1 hour, concentrated, purified by reverse phase preparative HPLC to afford the desired product as a white solid. (77 mg, 63%).

MS m/z=413.1 (M+H).

$^1$H NMR (400 MHz, DMSO-d6) δ 8.76 (t, J=5.7 Hz, 1H), 8.23 (dd, J=0.6, 8.6 Hz, 1H), 7.60 (d, J=7.7 Hz, 1H), 7.55 (d, J=8.7 Hz, 1H), 6.33 (d, J=7.8 Hz, 1H), 5.05-5.01 (m, 1H), 4.96 (br, 1H), 3.67-3.58 (m, 2H), 3.23 (t, J=6.2 Hz, 2H), 2.04-2.02 (m, 2H), 1.86-1.74 (m, 5H), 1.30-1.27 (m, 5H).

Method Z

Compound 63

6-Chloro-2-((R)-1-hydroxypropan-2-yl)-N-((6-hydroxyspiro[2.5]octan-6-yl)methyl)-1-oxo-1,2-dihydroisoquinoline-5-carboxamide

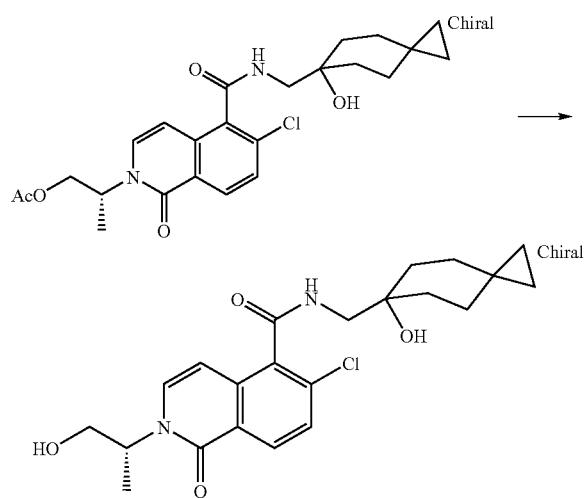

(2R)-2-(6-Chloro-5-(((6-hydroxyspiro[2.5]octan-6-yl)methylcarbamoyl)-1-oxoisoquinolin-2(1H)-yl)propyl acetate (130 mg, 0.00029 mol) and potassium carbonate (140 mg, 0.0010 mol) were stirred in methanol (6 mL, 0.1 mol) at room temperature for 1 hour, concentrated, and purified by reverse phase preparative HPLC to afford the desired product as a white solid.

MS m/z=419.5 (M+H)

$^1$H NMR (400 MHz, DMSO-d6) δ 8.60 (t, J=6.12 Hz, 1H), 8.22 (d, J=8.6 Hz, 1H), 7.59 (d, J=7.8 Hz, 1H), 7.54 (d, J=8.7 Hz, 1H), 6.44 (d, J=7.7 Hz, 1H), 5.04-5.01 (m, 1H), 4.98-4.95 (m, 1H), 4.29 (s, 1H), 3.67-3.56 (m, 2H), 3.33 (d, J=6.12 Hz, 2H), 1.78-1.73 (m, 2H), 1.65-1.50 (m, 4H), 1.28 (d, J=7.0 Hz, 3H), 0.98-0.90 (m, 2H), 0.26-0.15 (m, 4H).

Method AA1

Compound 64

2-(3-Fluoro-4-trifluoromethyl-phenyl)-N-{2-[(R)-2-(3-hydroxy-azetidin-1-yl)-1-methyl-ethyl]-6-methyl-1-oxo-1,2-dihydro-isoquinolin-5-yl}-acetamide

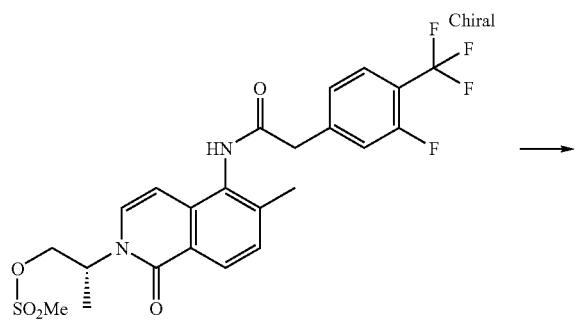

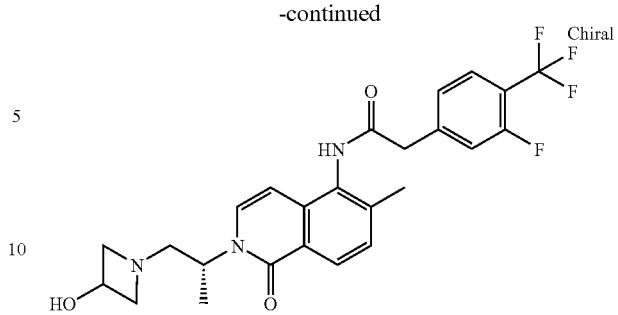

A solution of (R)-2-(5-(2-(3-fluoro-4-(trifluoromethyl)phenyl)acetamido)-6-methyl-1-oxoisoquinolin-2(1H)-yl)propyl methanesulfonate (100 mg, 0.2 mmol), 3-hydroxyazetidine hydrochloride (120 mg, 1.1 mmol), triethylamine (200 mg, 2 mmol) and methylene chloride (1 mL, 20 mmol) was stirred at room temperature overnight. The volatiles were removed and the residue was purified by reverse phase preparative HPLC to afford the desired product as a white solid.

MS m/z=491.7 (M+H)

$^1$H NMR (400 MHz, DMSO-d6) δ 9.91 (s, 1H), 8.06 (d, J=8.3 Hz, 1H), 7.80 (t, J=7.9 Hz, 1H), 7.53 (d, J=11.9 Hz, 1H), 7.46-7.36 (m, 3H), 6.44 (d, J=7.8 Hz, 1H), 5.20 (d, J=6.5 Hz, 1H), 4.94 (br, 1H), 4.05-4.01 (m, 1H), 3.92 (s, 2H), 3.45-3.43 (m, 1H), 2.81-2.48 (m, 4H), 2.22 (s, 3H), 1.25 (d, J=6.9 Hz, 3H).

Example 1

The P2X$_7$ receptor is strongly expressed in macrophage-derived cell lines, including, but not limited to, J774 (mouse macrophage line, American Type Culture Collection (ATCC), Rockville, Md., ATCC TIB-67), P388 (mouse cell line, ATCC CCL-46), P815 (mouse mast cell mastocytoma-derived line, ATCC TIB-64), THP-1 (Human monocyte-derived cell line, ATCC TIB202) and U937 (human cell line derived from histiocytic lymphoma, induceable to monocyte differentiation, ATCC CRL-1593.2) and in isolated macrophage cultures. Human or non-human animal macrophages are isolated using the procedure noted below.

The P2Z/P2X$_7$ receptor can be characterized by measuring channel opening, for instance ion flux, and/or by assessing pore formation, including by monitoring dye uptake or cell lysis in cells naturally expressing this receptor. Compounds such as ATP, 2' and 3'-(O)-(4-benzoyl benzoyl) ATP (BzATP) effect the formation of pores in the plasma membrane of these cells, particularly at low extracellular divalent ion concentrations (Buisman et al, Proc. Natl. Acad. Sci. USA 85:7988 (1988); Zambon et al, Cell. Immunol 156:458 (1994); Hickman et al Blood 84:2452 (1994)). Large molecular size dyes, including propidium dye YO-PRO-1, can be seen entering macrophage-derived cell lines during cell recordings (Hickman et al, Blood 84:2452 (1994); Wiley et al, Br J Pharmacol 112:946 (1994); Steinberg et al, J Biol Chem 262:8884 (1987)). Ethidium bromide (a fluorescent DNA probe) can also be monitored, where an increase in the fluorescence of intracellular DNA-bound ethidium bromide is observed. Expression of recombinant rat or human rP2X$_7$ in cells, including HEK293 cells, and in *Xenopus oocytes* demonstrates influx and pore formation by whole cell recordings and YO-PRO-1 fluorescence (Suprenant et al, Science 272:735 (1996); Rassendren et al, J Biol Chem 272:5482 (1997)).

The compounds of the invention may be tested for antagonist activity at the P2X$_7$ receptor. Tests to be performed include and are selected from: (i) electrophysiological experiments; (ii) YO-PRO1 fluorescence; (iii) ethidium bromide fluorescence; and (iv) IL-1β release from stimulated macrophages, including as described below. Compounds can be tested in vivo in animal models including for inflammation models (e.g. paw edema model, collagen-induced arthritis, EAE model of MS).

Isolation of Human Macrophages

Monocyte-derived human or non-human animal macrophage cultures are prepared as described by Blanchard et al (Blanchard et al, J Cell Biochem 57:452 (1995); Blanchard et al, J Immunol 147:2579 (1991)). Briefly, monocytes are isolated from leukocyte concentrates obtained from a healthy volunteer. Leukocytes are suspended in RPMI 1460 medium (Life Techologies, Inc.) with 20% serum (human for human cells), 2 mM glutamine, 5 mM HEPES, and 100 µg/ml streptomycin. Cells are allowed to adhere to culture flasks for 1-2 h, after which nonadherent cells are washed away. Adherent cells are cultured for 7-14d in this medium plus interferon-γ (human for human cells) (1000 units/ml). Macrophages are recovered from the culture flask by pipetting with cold phosphate-buffered saline and plated onto glass coverslips for electrophysiological or other experiments carried out 12-24 h later.

Example 2

Electrophysiological Experiments

Whole cell recordings are made using the EPC9 patch-clamp amplifier and Pulse acquisition programs (HEKA, Lambrecht, Germany). Whole-cell recordings are obtained from cells, e.g. J774A. 1 cells (American Type Culture Collection, Rockville, Md., ATCC TIB-67)); agonists are applied for periods of 1 to 3 s by a fast-flow U-tube delivery system [E. M. Fenwick, A. Marty, E. Neher, J. Physiol, (London) 331, 577 (1982)]. The internal pipette solution is 140 mM cesium-aspartate or potassium-aspartate, 20 mM NaCl, 10 mM EGTA, and 5 mM Hepes; normal external solution is 145 mM NaCl, 2 mM KCl, 2 mM CaCl$_2$, 1 mM MgCl$_2$, 10 mM Hepes, and 12 mM glucose. Low divalent external solution is nominally magnesium-free with 0.3 mM CaCl$_2$. Concentration-response curves are constructed in low divalent solution by recording currents in response to 1 s applications of agonist at 8 min intervals with normal external solution present for 6 min before each application. This protocol is necessary to prevent the development of sustained inward currents.

Reversal potentials ($E_{rev}$) are obtained by application of ATP (300 µM) or BzATP (30 µM)(controls), or the compound being tested, while the membrane is held at various potentials or by application of voltage ramps from −120 to 30 or 50 mV. Permeability ratios are calculated from $E_{rev}$ by first computing α(=$P_{Na}/P_K$, where P is permeability) for internal (i) and external (o) concentrations $[Na]_i$=20 mM, $[Na]_o$=145 mM, $[K]_o$=0 mM, and $[K]_i$=140 mM from α=([145/exp($E_{rev}$·F1RT)]−20)/140 (where F is the Faraday, R is the gas constant, and T is the absolute temperature). Other $P_x/P_{Na}$ values, when $[X]_o$=145 mM, $[Na]_i$=20 mM, $[K]_i$=140 mM, and $[Na]_o$=$[K]_o$=$[X]_i$=0 mM, are computed from $P_x/P_{Na}$=[(exp) $E_{rev}$F/RT)](20+140α))/145. In order of size, X is cesium, methylamine, tris(hydroxymethyl)-aminomethane, tetraethylammonium, and N-methyl-D-glucamine. The internal solution also contains 10 mM EGTA and 5 mM Hepes. External solutions also contain 10 mM glucose and normal or low concentrations of divalent cations; pH is maintained at 7.3 with HCl, histidine, or Hepes as required, and the osmolarity of all solutions is 295 to 315.

Example 3

YO-PRO1 Fluorescence

The Photonics Imaging (IDEA) system for microscopic fluorescence measurements (Photonics, Planegg, Germany) is used. Coverslips are placed at the stage of a Zeiss Axiovert 100 or equivalent inverted microscope and viewed under oil immersion with a 40X Fluor objective. YO-PRO-1 (10 µM; Molecular Probes, Eugene, Oreg.) is added to the superfusion fluid during electrophysiological recordings 3 to 6 min before switching to low divalent solution and washed out upon switching back to normal divalent solution, after which the fluorescent lamp is turned on and cells are examined with a fluorescein isothiocyanate filter. YO-PRO 1 fluorescence is measured using 491/509 nm excitation/emission wavelengths. Images are obtained at 5-20 s intervals during continuous superfusion (2 ml/min) with YO-PRO1 and varying concentrations of control ATP, BzATP or compound to be tested. For each experiment, the time course of YO-PRO 1 fluorescence is obtained for 10-20 individual cells and then averaged to afford the mean fluorescence signal. Results are expressed as mean signal at 3 min for rP2X$_7$, and the signal at 10 min is used for P2X$_7$ and human macrophage cells. All experiments are carried out at room temperature.

Example 4

Ethidium Bromide

Compounds of the invention are tested for antagonist activity at the P2X$_7$ receptor by monitoring Ethidium Bromide entering P2X$_7$ receptor-expressing cells on pore formation. The test is performed in 96-well flat bottomed microtitre plates, the wells being filled with 250 µl of test solution comprising 200 µl of a suspension of P2X$_7$-expressing cells (e.g. THP-1 cells, J774 cells, etc.)(2.5×10$^6$ cells/ml) containing 10$^{-4}$M ethidium bromide, 25 µL of a high potassium buffer solution containing 10$^{-5}$M BzATP, and 25 µl of a high potassium buffer solution containing test compound. The plate is covered with a plastic sheet and incubated at 37° C. for one hour. The plate is then read in a Perkin-Elmer fluorescent plate reader, excitation 520 nm, emission 595 nm, slit widths: Ex 15 nm, EM 20 nm. For the purposes of comparison, BzATP (a P2X$_7$ receptor agonist) and pyridoxal 5-phosphate (a P2X$_7$ receptor agonist) are used separately in the test as controls. From the readings obtained, a pIC$_{50}$ figure is calculated for each test compound. This figure is the negative logarithm of the concentration of test compound necessary to reduce the BzATP agonist activity by 50%.

Example 5

IL-1β Release

This Example demonstrates the testing of the compounds of this invention for efficacy as inhibitors of P2X$_7$-mediated release of IL-1β from human macrophages activated by the Alzheimer's beta amyloid peptide 1-42.

Cell Isolation

Monocytes are isolated from peripheral blood mononuclear cells (PBMCs) as follows. Whole blood is layered directly onto Histopak 1077-1 columns (Sigma Biochemicals) and centrifuged at 800×g for 15 minutes. The PBMC band of cells is removed to a fresh 50 ml culture tube and diluted 1:1 with wash buffer (Phosphate buffered saline, pH 7.4 containing 2 mM EDTA and 5 mg/ml BSA) followed by centrifugation at 800×g for 5 minutes. Cells are then washed by sequential resuspension of the cell pellet in wash buffer and centrifugation at 600×g for 5 minutes. The wash process is repeated until the supernatent is clear of contaminating platelets (generally, 5 to 6 washes). Monocytes are then purified from the PBMCs by negative selection using a monocyte isolation kit (Miltenyi Biotec, Inc.) that contains antibodies to non-monocytic cells, running the cells over a magnetic column to remove antibody-bound cells, and collecting the flow through volume of monocytes. Monocytes are washed once with wash buffer and seeded at 100,000 cells per well in 100 µl serum-free RPMI 1640 in 96-well plates and incubated for 1 hour at 37° C. in a 5% $CO_2$/95% $O_2$ humidified tissue culture incubator. After 1 hour, the medium is replaced with 100 µl complete culture medium (RPMI 1640, 10% human serum-type AB (heat inactivated), 25 mM HEPES, 2 mM glutamine, 50 U/ml each of penicillin and streptomycin) and incubated overnight (16 hours).

Dosing Regimen

The next day, the culture medium is replaced with 100 µl fresh complete culture medium in the absence or presence of human beta amyloid 1-42 peptide (5 µM) and incubated at 37° C. in a 5% $CO_2$/95% $O_2$ humidified tissue culture incubator for 5 hours. Medium is then removed and discarded. Each well is washed once with Hanks buffered saline (HBSS) containing 1 mM $CaCl_2$ followed by the addition of 80 µl of HBSS/$CaCl_2$-inhibiting compound of the present invention (10× stock in HBSS/$CaCl_2$ for a final concentration of 23 nM and 206 nM) and incubated 15 minutes in the tissue culture incubator followed by the addition of either 10 µl of HBSS/$CaCl_2$ or 10 µl of benzoyl ATP (BzATP; 3 mM stock in HBSS/$CaCl_2$ for a 300 µM final concentration) and incubated for a further 30 minutes in the tissue culture incubator. Medium is then removed to new 96-well plates for storage at −70° C. until the IL-1β content was quantitated by ELISA (from R&D Systems). The cells are washed once with HBSS/$CaCl_2$ followed by lysing the cells with 100 µl ice cold lysis buffer (100 mM Tris, pH 7.6, 1% Triton X-100, and 1 tablet per 30 ml Complete TM protease inhibitor from Roche Biochemicals, Inc). Cell lysates are stored at −70° C. until the IL-1β is quantitated by ELISA.

Example 6

In Vivo Animal Models

A. This Example Illustrates the Efficacy of the Compounds of this Invention in the Treatment of Multiple Sclerosis As described herein, experimental autoimmune encephalomyelitis (EAE) model is used to show such an efficacy. The following procedures are employed in this model.

Animals

SJL/J female mice, 8 wks. old, are obtained from Jackson Laboratories.

Antigens

Myelin Proteolipid Protein (PLP 139-151) (HSLGK-WLGHPDKF) (Cat # H-2478) is obtained from BACHEM, Bioscience, Inc., 3700 Horizon Dr., King of Prussia, Pa. 19406, 1-610-239-0300 (phone), 1-610-239-0800 (fax).

Complete Freund's Adjuvant H37 Ra [1 mg/ml Mycobacterium Tuberculosis H37 Ra] is obtained from Difco 1-800-521-0851 (Cat #3114-60-5, 6×10 ml).

Mycobacterium Tuberculosis is also obtained from Di co, 1-800-521-0851 (Cat #3114-33-8, 6.times.100 mg).

Pertussis Toxin

Bordetella Pertussis, (Lyophilized powder containing PBS and lactose) is obtained from List Biological Laboratories, 1-408-866-6363 (Product #180, 50 ug).

Induction of EAE in Mice

PLP139-151 peptide is dissolved in $H_2O$:PBS (1:1) solution to a concentration 7.5 mg/10 ml (for 75 µg PLP per group) and emulsified with an equal volume of CFA supplemented with 40 mg/10 ml heated-killed mycobacterium tuberculosis H37Ra. Mice are injected s.c. with 0.2 ml of peptide emulsion in the abdominal flank (0.1 ml on each side). On the same day and 72 hours later, mice are injected i.v. with 100% of 35 ng and 50 ng of Bordetella Pertussis toxin in saline respectively.

Clinical Assessment

STAGE 0: Normal
STAGE 0.5: Partial limp tail
STAGE 1: Complete Limp Tail
STAGE 2: Impaired righting reflex
STAGE 2.5: Righting reflex is delayed (Not weak enough to be stage 3).
STAGE 3: Partial hind limb paralysis
STAGE 3.5: One leg is completely paralyzed, and one leg is partially paralyzed,
STAGE 4: Complete hind limb paralysis
STAGE 4.5: Legs are completely paralyzed and Moribund
STAGE 5: Death due to EAE Clinical Courses of EAE Acute phase: First clinical episode (Day 10-18)
Remission: Phase of clinical improvement following a clinical episode; characterized by a reduction (>=one grade) in clinical score for at least two days after the peak score of acute phase or a disease relapse.

Relapse: Increase of at least one grade in clinical score for at least two days after remission has been attained.

The animals treated with the compounds of this invention generally would be expected to show improvements in clinical scores.

B. This Example Illustrates a Protocol for Determining the Efficacy of the Compounds of the Present Invention for the Treatment of Stroke Using an Animal Model.

Male Sprague Dawley rats (Charles River) weighing 280-320 g are given free access to food and water and acclimatized for a minimum of 4 days before use in experiments. All rats for use in studies are to be fasted beginning at 3:00 pm the day prior to surgery but given free access to water. Prior to surgery each rat is weighed. The rat is initially induced with 5% isoflurane (Aerrane, Fort Dodge), combined with 30% $O_2$, 70% $N_2O$ for 2-5 minutes. The rat is then placed on a circulating water-heating pad and into a nose cone for spontaneous respiration of anesthetic gases. The isoflurane is reduced to 2%. A rectal probe is inserted and body temperature maintained at 36.5-37.5° C. The hair is clipped at all surgical sites and these regions will then be scrubbed with Betadine.

Surgical Procedure

A temporalis muscle probe is placed into the right temporalis muscle and "brain" temperature" is monitored. A midline neck incision is made in the upper thorax of the rat. Careful dissection, isolation and retraction of the sternomastoideus, digastricus, and stemohyoideus muscles is made to expose the right common, internal and external carotid arteries. The right common carotid artery is isolated with a 5-0 silk suture. During surgery the suture is released allowing reperfusion every 2-4 minutes. The right external carotid and superior thyroid arteries are also isolated and the superior thyroid is cauterized, while the external carotid is ligated distally with a 5-0 silk suture. Another 5-0 silk suture is loosely tied around the external carotid artery. The occipital artery is isolated, ligated and incised. The internal carotid is isolated.

With the common and external carotid arteries immobilized, an aneurysm clip is placed onto the internal carotid artery. A small incision is made at the distal end of the external carotid. A 3-0 nylon suture coated with poly-L-lysine is then inserted into the external carotid and up into the common carotid artery. The loosely tied 5-0 silk suture around the external carotid is now gently tightened around the filament. The external carotid artery is then incised and the remaining piece of the external carotid artery with the filament is rotated so that the filament may be inserted into the internal carotid artery the length of insertion depending on the weight and rat strain. In Sprague Dawley rats the monofilament is inserted 18-19 mm (18 mm for rats weighing <300 gm, 19 mm for rats weighing 300 gm) effectively blocking blood flow to the middle cerebral artery.

The external jugular vein will be cannulated with PE 50 tubing for I.V. administration of compounds. The cannula will be exteriorized at the previously shaven, scruff of the neck and sutured in place. The wound will be closed by means of suture. The right femoral artery is catheterized for blood gas and glucose determination during surgery.

Two hours after the insertion of the monofilament suture the rats are re-anesthetized with the same anesthetic combination used initially and placed back into the nose cone with the reduction of isoflurane concentration to 2%. The neck incision is reopened to expose the external carotid artery. The restoration of blood flow is accomplished by completely withdrawing the intraluminal suture from the carotid arteries. The incision is then closed with 3-0 silk in an interrupted stitch.

Compound Administration

Five groups of 15 animals are subjected to the above methodology. Compounds are infused (I.V.) at various doses (dose response) over different time periods post MCAo. A predetermined concentration is infused over a pre-selected time period beginning at various intervals post MCAo. Vehicle-treated controls receive an infusion of normally 0.9 ml/hr. A positive control compound is run at the same time.

Neurological Tests

Prior to surgery, 2 hours following the onset of ischaemia and 24 hours after ischaemia a battery of neurological tests are performed. The postural reflex test, which is designed to examine upper body posture, when the rat is suspended by the tail above a flat surface. A normal rat will extend the entire body and both forelimbs towards the surface. Rats with an infarction will consistently flex the contralateral limb and show signs of body rotation. The rats respond to a gentle lateral push with a finger behind the shoulders. A normal rat would resist such a push, whereas a rat with an infarction will not. The elicited forelimb placing in response to visual and tactile stimuli. The animal is held by the body so that the lateral or dorsal forepaw surface is placed against a bench. This test is repeated but on this occasion obstructing the view of the rat.

Upon completion of each experiment, all animals are deeply anaesthetized with isoflurane (5%), euthanized by decapitation, and the brains removed, the extent and location of the ischaemic damage is verified histologically by means of tetrazolium chloride.

C. This Example Illustrates the Anti-Inflammatory Activity of the Compounds of this Invention Using a Model of 2,4-Dinitrobenzenesulfonic Acid (DNBS) Induced Distal Colitis (a Model of Inflammatory Bowel Disease).

Test Substance and Dosing Pattern

A compound of this invention is dissolved in vehicle of 2% Tween 80 in distilled water for oral administration at a dose of 50 mg/kg or dissolved in vehicle of 2% Tween 80 and 0.9% NaCl for intraperitoneal injection at 30 mg/kg. The dose is given once daily for 7 consecutive days. Dosing volume is 10 ml/kg. DNBS was challenged 2 hours after dosing on the second day.

Animals

In these studies, male Wistar, Long Evans rats provided by animal breeding center of MDS Panlabs Taiwan, Ltd. and Balb/cByJ derived male mice (weighing 20±2 gms), provided by National Laboratory Animals Breeding Research center (NALBRC, Taiwan), may be used. Space allocation of 6 animals may be 45×23×15 cm. Animals are housed in APEC® cages (Allentown Caging, Allentown, N.J. 08501, USA) in a positive pressure isolator (NuAire®, Mode: Nu-605, airflow velocity 50±5 ft/min, HEPA Filter) and maintained in a controlled temperature (22° C.-24° C.) and humidity (60%-80%) environment with 12 hours light dark cycles for at least one week in MDS Panlabs Taiwan laboratory prior to being used. Free access to standard lab chow for rats (Fwusow Industry Co., Limited, Taiwan) and tap water is granted. All aspects of this work including housing, experimentation and disposal of animals would be performed in general accordance with the International Guiding Principles for Biomedical Research Involving Animals (CIOMS Publication No. ISBN 92 90360194, 1985).

Chemicals

DNBS is obtained from TCI, Tokyo, Japan, ethanol is from Merck, Germany and Sulfasalazine is purchased from Sigma, USA.

Equipment

Electriconic scale (Tanita, model 1140, Japan), Electriconic scale (Sartorius, R160P, Germany), Glass syringe (2 ml, Mitsuba, Japan), Rat oral needle, Hypodermic needle (25G.times. 1"TOP Corporation, Japan), Stainless Scissors (Klappenclear, Germany), Stainless Forceps (Klappenclear, Germany).

Method

Groups of 3 Wistar derived male rats weighing 180±20 gms are used. Distal colitis is induced by intra-colonic instillation of DNBS (2,4-dinitrobenzene sulfonic acid, 30 mg in 0.5 ml ethanol 30%) after which, 2 ml of air is gently injected through the cannula to ensure that the solution remains in the colon. Test substance is administered orally (PO) at a dose of 50 mg/kg or intraperitoneally (IP) at 30 mg/kg once daily for 7 consecutive days. DNBS is instillated into the distal colon of each animal 2 hours after dosing on the second day. The control group is similarly treated with vehicle alone and sulfasalazine (300 mg/kg, PO) is used as reference agent. Animals are fasted 24 hours before DNBS challenge and 24 hours after the final treatment when they are sacrificed and each colon is removed and weighed. During the experiments, presence of diarrhea is recorded daily. When the abdominal cavity is opened before removal of the colon, adhesions between the colon and other organs are noted. After weighing the colon, the extent of colonic ulceration is observed and noted as well. Colon-to-body weight ratio is then calculated for each animal according to the formula: Colon (g)/BW×100%. The "Net" increase in ratio of Vehicle-control +DNBS group relative to Vehicle-control group is used as a base value for comparison with test substance treated groups and expressed as % decrease in inflammation. A 30 percent or more (30%) decrease in "Net" colon-to-body weight ratio for each test substance treated group relative to the "Net" vehicle+DNBS treated group is considered significant.

D. This Example Illustrates the Anti-Inflammatory Activity of the Present Compounds Using a Model of Carrageenan Induced Paw edema (a Model of Inflammation, Carrageenan)
Test Substance and Dosing Pattern A compound of this invention is dissolved in vehicle of 2% Tween 80/0.9% NaCl and administered intraperitoneally at a dose of 30 mg/kg 30 minutes before carrageenan (1% 0.1 ml/paw) challenge. Dosing volume is 10 ml/kg.
Animals Animals are conditioned in accordance with the procedures set forth in the previous Example.
Chemicals Carrageenan is obtained from TCI, Japan; Pyrogen free saline is from Astar, Taiwan; and Aspirin is purchased from ICN BioMedicals, USA.
Equipment Glass syringe (1 ml and 2 ml Mitsuba, Japan), Hypodermic needle 24Gx1" (Top Corporation, Japan), Plethysmometer #7150 (UGO Basile, Italy), and Water cell 25 mm Diameter, #7157 (UGO Basile, Italy).
Method Test substance (Example) is administered IP (30 mg/kg) to groups of 3 Long Evans derived male overnight fasted rats weighing 150±20 gms 30 minutes before right hind paw injection of carrageenan (0.1 ml of 1% suspension intraplantar). Hind paw edema, as a measure of inflammation, is recorded 3 hours after carrageenan administration using a plethysmometer (Ugo Basile Cat. #7150) with water cell (25 mm diameter, Cat. #7157). Reduction of hind paw edema by 30 percent or more (30%) indicated significant acute anti-inflammatory activity.

E. This Example Illustrates the Anti-Inflammatory Activity of the Present Compounds Using a Model of Balb/c Mice Subjected to Monoclonal Antibody (mAb) Type II Collagen Induced Arthritis.
Test Substance and Dosing Pattern A compound of this invention is dissolved in vehicle of 2% Tween 80/0.9% NaCl, at doses of 50 or 30 and administered orally (50 mg/kg) or intraperitoneally at 30 mg/kg once daily for 3 consecutive days after monoclonal antibody of collagen was injected. Dosing volume is 20 ml/kg.
Animals Animals are conditioned in accordance with the procedures set forth in the previous Example.
Chemicals Lipopolysaccharide is obtained from Sigma, USA; Indomethacin is from Sigma, USA; Arthrogen-CIA™. Monoclonal Antibodies D8, F10, DI-2G and A2 are obtained from IBL, Japan; Phosphate-Buffered Saline is purchased from Sigma, USA; and Tween 80 is from Wako, Japan.
Equipment Plethysmometer (Ugo Basile, Italy) and Water Cell (Ugo Basile, Italy).
Method Groups of 5 Balb/cByJ mice strain, 6-8 weeks of age, are used for the induction of arthritis by monoclonal antibodies (mAbs) responding to type II collagen, plus lipopolysaccharide (LPS). The animals are administered intravenously with a combination of 4 different mabs in a total of 4 mg/mouse at day 0, and followed by intravenous 25 µg of LPS 72 hours later (day 3). From day 3, one hour after LPS administration, ML-659 at 50 mg/kg (PO) or 30 mg/kg (IP) and vehicle (2% Tween 80/0.9% NaCl, PO) as well as the positive control indomethacin, 3 mg/kg (PO) are administered once daily for 3 consecutive days. A plethysmometer (Ugo Basile Cat #7150) with water cell (12 mm diameter) is used for the measurement of increase in volume of the two hind paws at day 0, 5, 7, 10, 14, and 17. The percent inhibition of increase in volume is calculated by the following formula:

$$\text{Inhibition (\%)}: [1-(Tn-T)/(Cn-Co)] \times 100$$

Where:
Co (Cn): volume of day 0 (day n) in vehicle control
To (Tn): volume of day 0 (day n) in test compound-treated group
The reduction of both of two hind paws edema by more than 30% is considered significant.

Example 7

Neuropathic Pain Model

This example illustrates the analgesic activity of the compounds of this invention using a Sciatic Nerve ligation model of mononeuropathic pain
Test System Adult male Sprague Dawley (SD) rats weighing 250-300 gm (Charles River Laboratories, San Diego, Calif.) are used. The animal room is lighted artificially at a 12-hr light-dark cycle (from 7:00 A.M. to 7:00 P.M) with water and food supply ad libitum. Animals are allocated randomly into groups.
Model Induction Sciatic nerve ligation (SNL, Seltzer's model):
Under anesthesia with pentobarbital (50 mg/kg, i.p.) and aseptic techniques, the selective nerve injury is created by tightly ligating the selective portion of the common sciatic nerve according to the method of Seltzer (1990). Briefly, the high-thigh level of the left sciatic nerve is exposed after skin incision and blunt separation of muscles at a site near the trochanter just distal to the point at which the posterior biceps semitendious nerve nerve branches from the common sciatic nerve. The nerve is then fixed in this position with fine forceps by pinching the epineurium on its dorsal aspect, taking care not to press the nerve against underlying structures. An 8-0 silicon-treated silk suture is inserted into the nerve with a ⅜ curved, reversed-cutting mini-needle, and tightly ligated so that the dorsal ⅓-½ of the nerve is trapped in the ligature. The muscles are sutured in layers, and the skin closed with wound clips. Animals are then returned to their home cages. Rats exhibiting postoperative neurological deficits or poor grooming are excluded from the experiments.
Equipment The following equipment is used in the current studies: von Frey filament set (Touch-test Sensory Evaluator, North Coast Medical Inc., Morgan Hill, Calif.).
Statistical Methods:

Within each experiment mean, standard error of the mean (SEM) and statistical significance are calculated using the average, standard error of the mean and unpaired, two-tailed t-Test functions, respectively, using Microsoft Excel®. Statistical significance of effects observed between individual experiments is determined, using Prism (GraphPad Software Inc., San Diego, Calif.) for the one-way or two-way analysis of variance (ANOVA) function. Statistical analyses are performed with a confidence limit of 0.95 and a significance level of 0.05.

Example 8

Pore Formation

THP-1 cells (ATCC Cat #285-IF-100) are plated in 96 well plates at a concentration of 200,000 cells per well and allowed to differentiate in RPMI-1640 media (ATCC Cat #30-2001) containing 10% FBS, 100 IU/mL penicillin, 100 ug/mL streptomycin, 100 ng/mL LPS and 100 ng/mL IFN-γ for 16 hours.

Following differentiation, the cells are pretreated with the compound of interest at the appropriate concentration for 30 minutes in RPMI-1640 media containing 100 IU/mL penicillin, 100 ug/mL streptomycin. The pretreatment media is then replaced with assay buffer (20 mM HEPES, 10 mM d-glucose, 118 mM NMDG, 5 mM KCl, 0.4 mM $CaCl_2$) containing 5 uM Yo-Pro 1 (Molecular Probes Cat # Y3603) and the compound of interest at the appropriate concentration and the cells are incubated for an additional 10 minutes. 2',3'-O-(4-benzoylbenzoyl)-adenosine 5'-triphosphate (Sigma Aldrich Cat# B6396) is then added to a final concentration of 40 uM, and fluoroscence readings are then measured at 491/509 excitation/emission every minute for 50 minutes using a Tecan Safire plate reader. During this time, temperature is maintained at 37° C. Background adjusted fluorescence levels between drug treated and non-treated cells are used to calculate the percent inhibition.

Example 9

IL-1β Release Assay

THP-1 cells (ATCC Cat #285-IF-100) are plated in 96 well plates at a concentration of 200,000 cells per well and allowed to differentiate in RPMI-1640 media (ATCC Cat #30-2001) containing 10% FBS, 100 IU/mL penicillin, 100 ug/mL streptomycin, 100 ng/mL LPS and 100 ng/mL IFN-γ for 16 hours. Following differentiation, the cells are treated for an additional 2 hours in RPMI-1640 media containing 100 IU/mL penicillin, 100 ug/mL streptomycin and fresh LPS at 100 ng/mL. The cells are then pretreated for 30 minutes with the compound of interest at the appropriate concentration in RPMI media containing 100 IU/mL penicillin, 100 ug/mL streptomycin. Following the pretreatment 2',3'-O-(4-benzoylbenzoyl)-adenosine 5'-triphosphate (Sigma Aldrich Cat # B6396) is added to a final concentration of 250 uM, and the cells are incubated for an additional 45 minutes. 30 uL of cell supernatant is then collected and IL-1β levels are determined via ELISA (R&D systems Cat. # HSLB50) according to manufacturer's recommendations using a Tecan Safire plate reader. Background adjusted IL-1β levels of drug treated and non-treated cells are used to calculate the percent inhibition.

Example 10

Calcium Influx Assay

132N1 cells (ECACC #86030402) stably expressing human P2X7 are plated in a 96 well plate at a density of 50,000 cells/well in DMEM w/o phenol red (MediaTech #17-205-CV)+10% FBS, 100 IU/mL penicillin, 100 ug/mL streptomycin, 2 mM L-alanyl-L-glutamine (MediaTech #25-015-CV) and 500 ug/mL of G418 for 24 hrs. Calicum influx is detected using a BD Calcium Assay Kit (BD BioImaging Systems #80500-311) and a FLIPR$^{tetra}$ Fluorometric Imaging Plate Reader Molecular Devices). Briefly, 100 uL of DMSO is added to a tube of dye. A 1× dye loading solution is made up containing 10 mL HBSS/HEPES (980 mL of Hanks Balanced Salt Solution (Invitrogen #14025-126)+20 mL of 1M HEPES (Invitrogen #15630-080)), 500 uL of signal enhancer, 100 uL of 250 mM Probenicid and 5 uL of the reconstitued dye. The media is removed from the cells and 100 uL of the dye loading mix is added to each well for 60 minutes at 37° C. in a 5% $CO_2$ incubator followed by 10 minutes at room temperature. The compound of interest in HBSS/HEPES solution is added to the desired concentration in each well for 30 minutes. Following compound pretreatment, the agonist 2',3'-O-(4-benzoylbenzoyl)-adenosine 5'-triphosphate in HBSS/HEPES is added to a final concentration of 130 uM in each well. Fluorescence readings for each well are made every 1 second for 20 seconds prior to, and 280 seconds post agonist addition. Background adjusted Max-Min values for drug treated vs. non drug treated cells are used to calculate % inhibition.

Example 11

Human Whole Blood Il-1β Release Assay

Human whole blood is collected in a BD plasma vacutainer tube spray-coated with 150 USP units of Sodium Heparin (BD #367874). 150 uL of whole blood is aliquoted into the wells of a Costar 96 well assay plate (Corning, Inc. #3795). LPS (EMD #437625) in RPMI 1640 media containing 25 mM HEPES (Mediatech #10-041-CV) is added to a final concentration of 200 ng/mL and the blood incubated for 1 hr 30 minutes at 37° C. in a 5% $CO_2$ incubator. The compound of interest in RPMI 1640 media containing 25 mM HEPES is added to the desired concentration and the blood is incubated for an additional 30 minutes at 37° C. in a 5% $CO_2$ incubator. ATP (Sigma # A6559) is prepared in 25 mM HEPES (Invitrogen #15630) and the pH adjusted to 7.0 with Sodium Hydroxide. Following compound pretreatment, ATP is added to the whole blood to a final concentration of 2.5 mM and the blood is then incubated for 45 minutes at 37° C. in a 5% $CO_2$ incubator. The plates are then spun at 1000 g for 2 minutes and the plasma collected. Plasma IL-1β levels are determined via ELISA (R&D systems Cat. # HSLB50) according to manufacturer's recommendations using a Tecan Safire plate reader. Background adjusted IL-1β levels of drug treated and non-treated blood are used to calculate the percent inhibition.

In addition to the compounds exemplified above, various other compounds of this invention have been prepared using the procedure and synthetic methods described above, or via routine modification of the methods described here, and the corresponding starting materials, appropriate reagents, and purification methods known to those skilled in the art. Accordingly, the compounds prepared along with their analytical data are listed in Table 1, below.

The synthetic and biological examples described in this application are offered to illustrate this invention and are not to be construed in any way as limiting the scope of this invention. In the examples, all temperatures are in degrees Celsius (unless otherwise indicated). The compounds that have been prepared in accordance with the invention along with their biological activity data are presented in the following Table. The syntheses of these representative compounds are carried out in accordance with the methods set forth above.

Exemplary Compounds of the Invention

The following compounds have been or can be prepared according to the synthetic methods described herein for example, methods A-AA1. The compounds set forth in Table 1 were tested for activity in a cellular model as described herein. Specifically, cells were pretreated with differing amounts of the compound under test and released IL-1β determined as in Example 9, above. Measurements were made and $IC_{50}$ values, presented in Table 1, below, were determined by fitting the data to a four parameter logistic equation using GraphPad Prism software (GraphPad Software, Inc). The equation may be expressed by the following formula:

$$Y=\text{Bottom}+(\text{Top}-\text{Bottom})/(1+10^{((\log EC50-X)*\text{HillSlope})})$$

where X is the logarithm of concentration, Y is the response and Y starts at Bottom and goes to Top with a sigmoid shape.

TABLE 1

IL-1β IC$_{50}$ values of Exemplary Compounds

| ID | Structure | MW (Calcd) | MW (Obs) | IL-1β IC$_{50}$ (nM) |
|---|---|---|---|---|
| 1 | 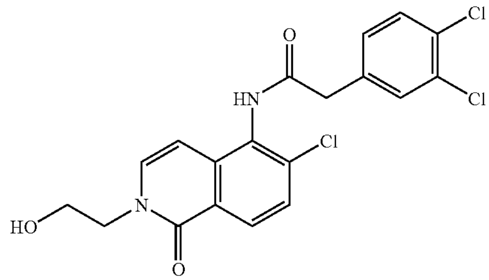 | 425.7 | | |
| 2 | 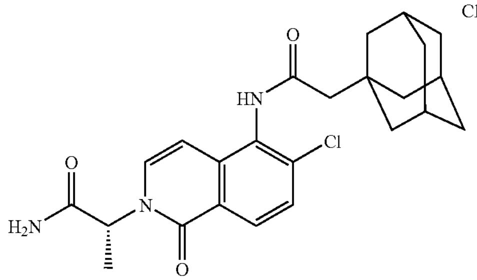 | 441.96 | 442.3 | 0.1 |
| 3 | 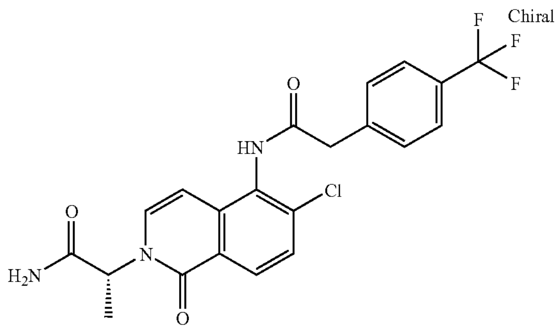 | 451.83 | 452.2 | 2 |
| 4 | 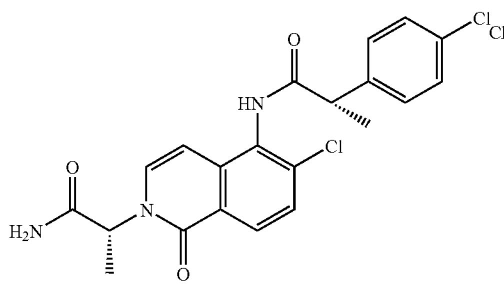 | 432.31 | 432.1 | 18 |
| 5 | 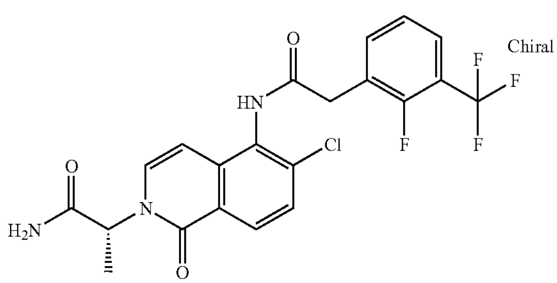 | 469.82 | 470.2 | 7 |

TABLE 1-continued

IL-1β IC₅₀ values of Exemplary Compounds

| ID | Structure | MW (Calcd) | MW (Obs) | IL-1β IC$_{50}$ (nM) |
|---|---|---|---|---|
| 6 | Chiral | 436.27 | 437.3 | 395 |
| 7 | Chiral | 447.41 | 448.3 | 48 |
| 8 | Chiral | 451.83 | 452.1 | 113 |
| 9 | Chiral | 452.4 | 452.9 | 439 |

TABLE 1-continued

IL-1β IC$_{50}$ values of Exemplary Compounds

| ID | Structure | MW (Calcd) | MW (Obs) | IL-1β IC$_{50}$ (nM) |
|---|---|---|---|---|
| 10 | 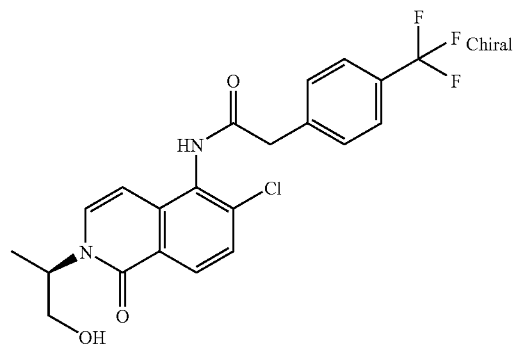 | 438.83 | 439.4 | 10 |
| 11 | 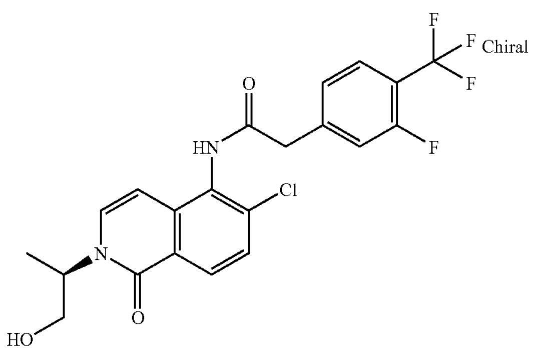 | 456.82 | 457.2 | 5 |
| 12 | 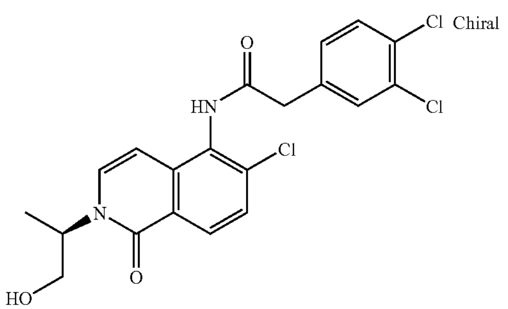 | 439.72 | 440.4 | 13 |
| 13 | 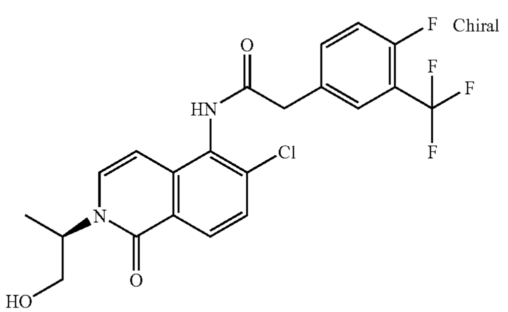 | 456.82 | 457.4 | 0.4 |

TABLE 1-continued
IL-1β IC$_{50}$ values of Exemplary Compounds
| ID | Structure | MW (Calcd) | MW (Obs) | IL-1β IC$_{50}$ (nM) |
|---|---|---|---|---|
| 14 | 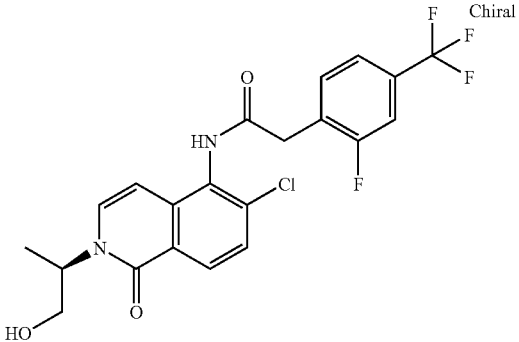 | 456.82 | 457.4 | 31 |
| 15 | 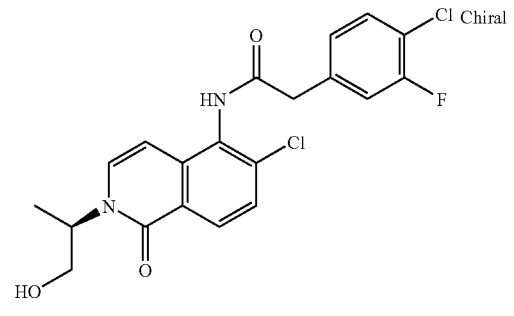 | 423.27 | 423.3 | 6 |
| 16 | 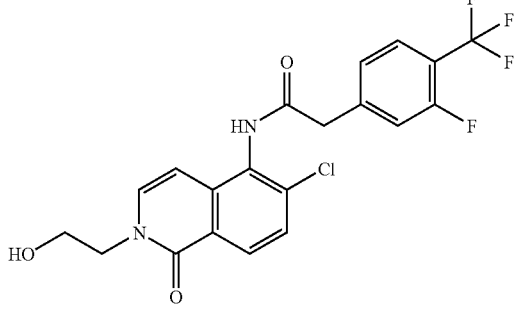 | 442.79 | 443.3 | 6 |
| 17 | 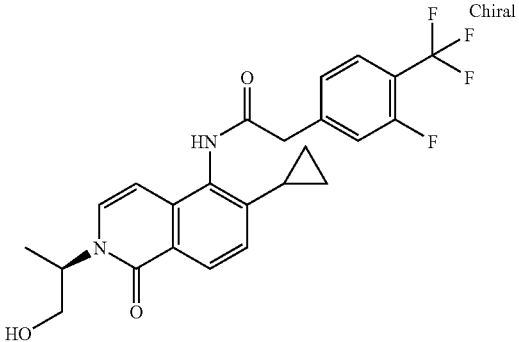 | 462.44 | 463.5 | 9 |

TABLE 1-continued

IL-1β IC$_{50}$ values of Exemplary Compounds

| ID | Structure | MW (Calcd) | MW (Obs) | IL-1β IC$_{50}$ (nM) |
|---|---|---|---|---|
| 18 | 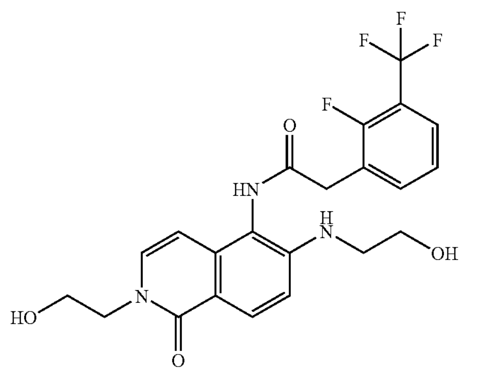 | 467.42 | 468.4 | 1672 |
| 19 | 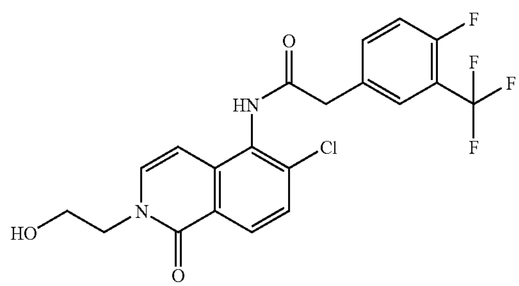 | 442.79 | 443.3 | 5 |
| 20 | 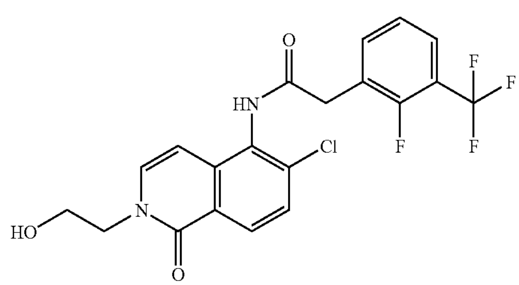 | 442.79 | 443.2 | 63 |
| 21 | Chiral | 436.4 | 437.4 | 0.4 |

TABLE 1-continued

IL-1β IC₅₀ values of Exemplary Compounds

| ID | Structure | MW (Calcd) | MW (Obs) | IL-1β IC₅₀ (nM) |
|---|---|---|---|---|
| 22 | 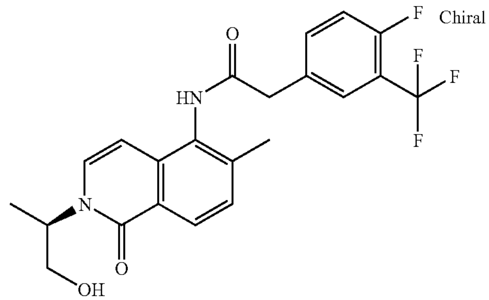 | 436.4 | 437.5 | 0.7 |
| 23 | 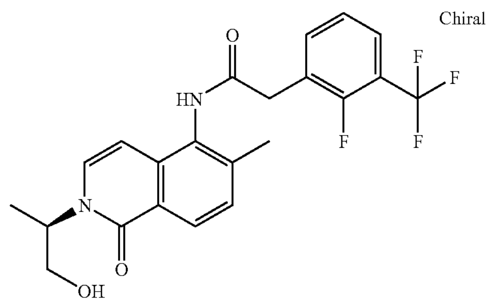 | 436.4 | 437.5 | 11 |
| 24 | 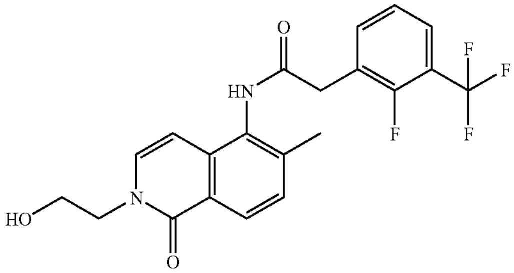 | 422.38 | 423.3 | 65 |
| 25 | 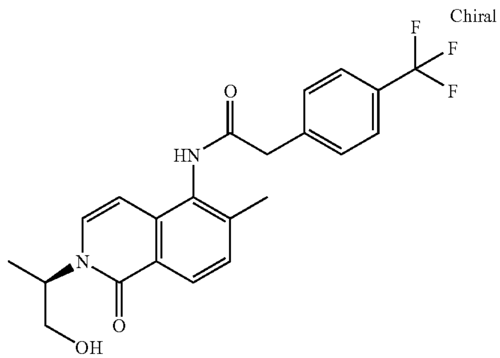 | 418.41 | 419.5 | 6 |

TABLE 1-continued

IL-1β IC₅₀ values of Exemplary Compounds

| ID | Structure | MW (Calcd) | MW (Obs) | IL-1β IC₅₀ (nM) |
|----|-----------|------------|----------|-----------------|
| 26 | Chiral | 402.85 | 403.5 | 5 |
| 27 | 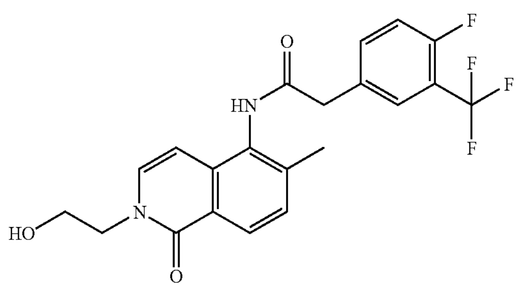 | 422.38 | 423.3 | 7 |
| 28 | 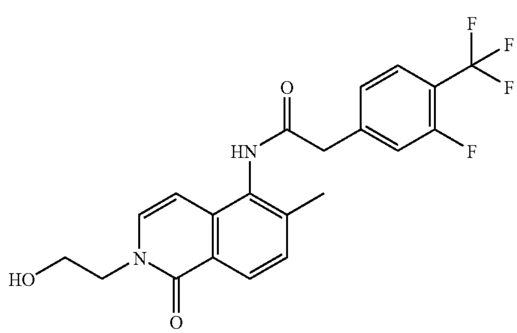 | 422.38 | 423.3 | 9 |
| 29 | Chiral | 447.43 | 448.4 | 23 |

TABLE 1-continued

IL-1β IC₅₀ values of Exemplary Compounds

| ID | Structure | MW (Calcd) | MW (Obs) | IL-1β IC₅₀ (nM) |
|---|---|---|---|---|
| 30 | Chiral | 447.43 | 448.4 | 11 |
| 31 | Chiral | 408.54 | 409.2 | 5 |
| 32 | Chiral | 370.49 | 371.4 | 9 |
| 33 | Chiral | 436.4 | 437.5 | 53 |

TABLE 1-continued

IL-1β IC$_{50}$ values of Exemplary Compounds

| ID | Structure | MW (Calcd) | MW (Obs) | IL-1β IC$_{50}$ (nM) |
|---|---|---|---|---|
| 34 | (Chiral structure: 3-fluoro-4-(trifluoromethyl)phenylacetamide linked to 6-chloro-2-[(S)-1-hydroxypropan-2-yl]-1-oxo-1,2-dihydroisoquinolin-5-yl) | 456.82 | 457 | 23 |
| 35 | (Chiral structure: 3-(trifluoromethyl)phenylacetamide linked to 6-methyl-2-[(S)-1-hydroxypropan-2-yl]-1-oxo-1,2-dihydroisoquinolin-5-yl) | 418.41 | 419.4 | 2 |
| 36 | (Chiral structure: cycloheptylacetamide linked to 6-chloro-2-[(S)-1-hydroxypropan-2-yl]-1-oxo-1,2-dihydroisoquinolin-5-yl) | 390.91 | 391.4 | 4 |
| 37 | (Chiral structure: 2-(1-hydroxycycloheptyl)acetamide linked to 6-methyl-2-[(S)-1-hydroxypropan-2-yl]-1-oxo-1,2-dihydroisoquinolin-5-yl) | 386.49 | 387.5 | 42 |

TABLE 1-continued

IL-1β IC$_{50}$ values of Exemplary Compounds

| ID | Structure | MW (Calcd) | MW (Obs) | IL-1β IC$_{50}$ (nM) |
|---|---|---|---|---|
| 38 | 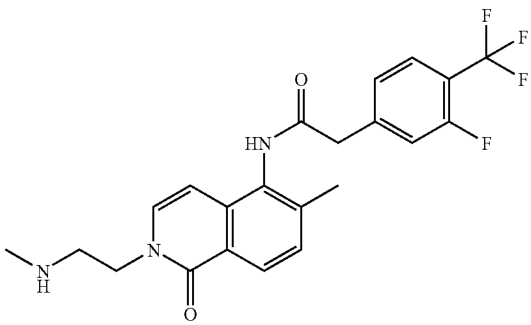 | 435.42 | 436.3 | 43 |
| 39 | Chiral | 438.83 | 439.3 | 1 |
| 40 | Chiral | 436.4 | 437.3 | 3 |
| 41 | Chiral | 456.82 | 457.2 | 7 |

TABLE 1-continued
IL-1β IC₅₀ values of Exemplary Compounds
| ID | Structure | MW (Calcd) | MW (Obs) | IL-1β IC₅₀ (nM) |
|---|---|---|---|---|
| 42 | 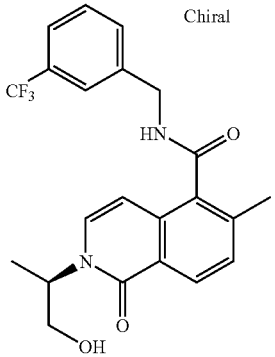 | 418.41 | 419.5 | 7 |
| 43 | 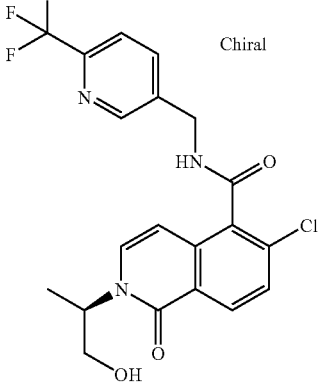 | 439.82 | 440.3 | 310 |
| 44 | 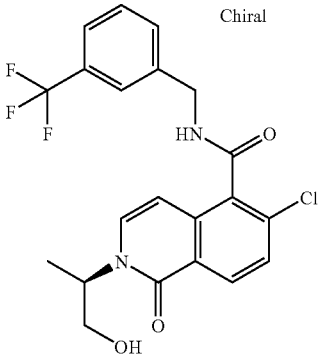 | 438.83 | 439.3 | 10 |
| 45 | 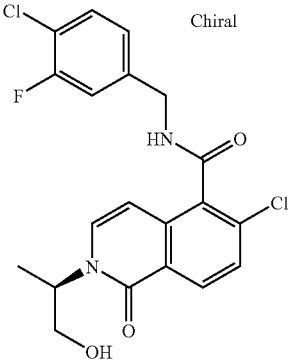 | 423.27 | 423.2 | 13 |

TABLE 1-continued
IL-1β IC$_{50}$ values of Exemplary Compounds
| ID | Structure | MW (Calcd) | MW (Obs) | IL-1β IC$_{50}$ (nM) |
|---|---|---|---|---|
| 46 | 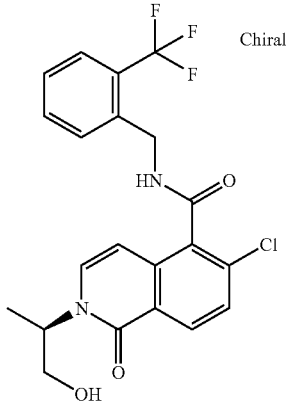 Chiral | 438.83 | 439.3 | 500 |
| 47 | 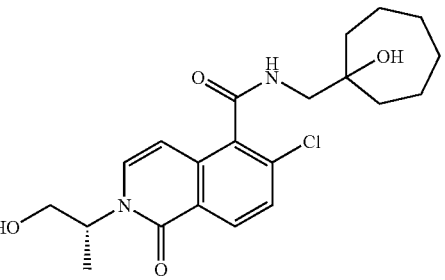 Chiral | 406.91 | 407.3 | 0.8 |
| 48 | 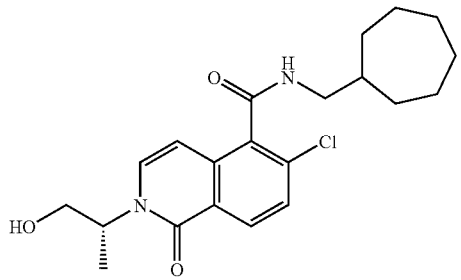 Chiral | 390.91 | 391.5 | 0.2 |
| 49 | 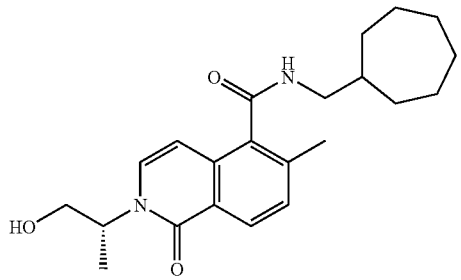 Chiral | 370.49 | 371.4 | 0.7 |

TABLE 1-continued

IL-1β IC$_{50}$ values of Exemplary Compounds

| ID | Structure | MW (Calcd) | MW (Obs) | IL-1β IC$_{50}$ (nM) |
|---|---|---|---|---|
| 50 | Chiral | 402.85 | 403.2 | 3 |
| 51 | Chiral | 449.4 | 450.4 | 0.4 |
| 52 | Chiral | 386.49 | 387.5 | 4 |
| 53 | Chiral | 404.89 | 405.3 | 532 |

TABLE 1-continued

IL-1β IC$_{50}$ values of Exemplary Compounds

| ID | Structure | MW (Calcd) | MW (Obs) | IL-1β IC$_{50}$ (nM) |
|---|---|---|---|---|
| 54 | Chiral | 420.93 | 421.6 | 1 |
| 55 | Chiral | 420.93 | 421.5 | 1 |
| 56 | Chiral | 460.88 | 461.2 | 9 |
| 57 | Chiral | 392.88 | 393.3 | 5 |
| 58 | 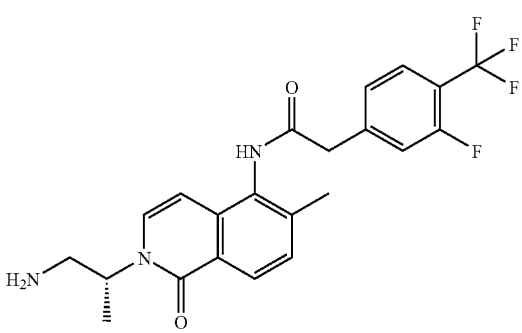 | 435.42 | 437.2 | 0.01 |

TABLE 1-continued

IL-1β IC$_{50}$ values of Exemplary Compounds

| ID | Structure | MW (Calcd) | MW (Obs) | IL-1β IC$_{50}$ (nM) |
|---|---|---|---|---|
| 59 | 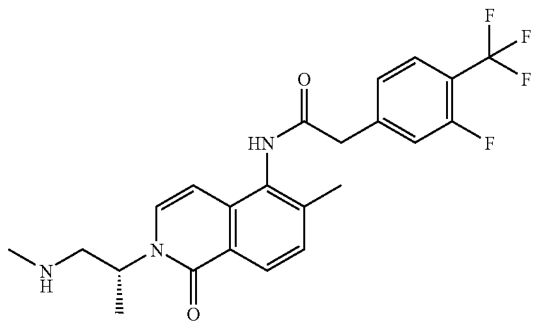 | 449.45 | 450.4 | 2 |
| 60 | Chiral | 504.53 | 505.2 | 1 |
| 61 | Chiral | 412.86 | 413.1 | 5 |
| 62 | 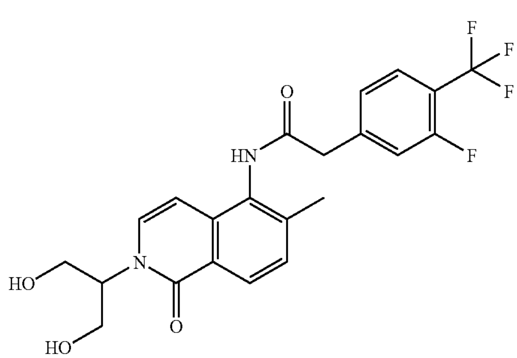 | 452.4 | 453.3 | 30 |

TABLE 1-continued

IL-1β IC₅₀ values of Exemplary Compounds

| ID | Structure | MW (Calcd) | MW (Obs) | IL-1β IC₅₀ (nM) |
|---|---|---|---|---|
| 63 | Chiral | 418.92 | 419.5 | 0.6 |
| 64 | Chiral | 491.48 | 491.7 | 9 |
| 65 | Chiral | 454.9 | 455.3 | 0.3 |
| 66 | Chiral | 504.53 | 504.8 | 5 |

TABLE 1-continued

IL-1β IC₅₀ values of Exemplary Compounds

| ID | Structure | MW (Calcd) | MW (Obs) | IL-1β IC₅₀ (nM) |
|---|---|---|---|---|
| 67 | 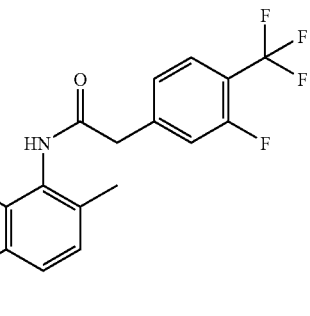 Chiral | 504.53 | 505 | 2 |
| 68 | 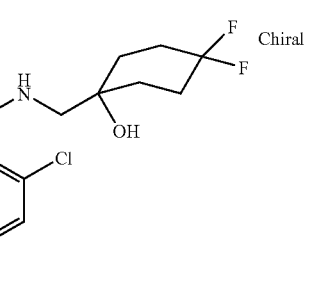 Chiral | 428.86 | 429.1 | 3 |
| 69 | 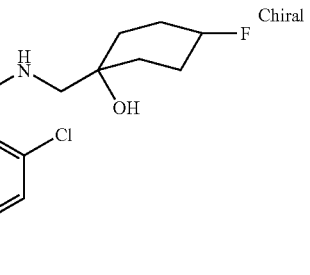 Chiral | 410.87 | 411.2 | 6 |

Half-Life in Human Liver Microsomes (HLM)

Test compounds (1 μM) are incubated with 3.3 mM $MgCl_2$ and 0.78 mg/mL HLM (HL101) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. An aliquot of samples of P450 group is collected at 0, 10, 30, and 60 min time point, where 0 min time point indicated the time when NADPH is added into the reaction mixture of P450 group. An aliquot of samples of non-P450 group is collected at −10 and 65 min time point. Collected aliquots are extracted with acetonitrile solution containing an internal standard. The precipitated protein is spun down in centrifuge (2000 rpm, 15 min). The compound concentration in supernatant is measured by LC/MS/MS system.

The half-life value is obtained by plotting the natural logarithm of the peak area ratio of compounds/internal standard versus time. The slope of the line of best fit through the points yields the rate of metabolism (k). This is converted to a half-life value using following equations:

Half-life=ln 2/$k$

The results of the tests and corresponding $T_{1/2}$ values are set forth in Table 2, below.

TABLE 2

T-Half Life In Hours For Exemplary Compounds

| ID | Half Life (hr) |
|---|---|
| 2 | 0.8 |
| 3 | 3.3 |
| 5 | 1.2 |
| 10 | 3.2 |
| 11 | 1.6 |
| 12 | 0.9 |
| 13 | 1.0 |
| 15 | 1.3 |
| 16 | 3.7 |
| 19 | 1.1 |
| 21 | 1.5 |
| 22 | 0.7 |
| 23 | 1.4 |
| 25 | 4.6 |
| 26 | 1.6 |
| 28 | 3.7 |
| 29 | 3.5 |
| 40 | 2.6 |

TABLE 2-continued

T-Half Life In Hours For Exemplary Compounds

| ID | Half Life (hr) |
|---|---|
| 41 | 3.0 |
| 42 | 0.8 |
| 44 | 1.1 |
| 45 | 1.6 |
| 47 | 0.4 |
| 49 | 0.3 |
| 51 | 1.3 |
| 54 | 0.3 |
| 56 | 0.7 |
| 65 | 0.62 |
| 68 | 0.65 |

Pharmacokinetic Evaluation of Compounds Following Intravenous and Oral Administration in Rats.

Male Sprague-Dawley rats are acclimated for at least 24 hours prior to experiment initiation. During the acclimation period, all animals receive food and water ad libitum. However, food but not water is removed from the animals' cages at least 12 hours before initiation of the experiment. During the first 3 hours of experimentation, the animals receive only water ad libitum. At least three animals each are tested for intravenous and oral dosage. For intravenous formulation, compounds are dissolved (0.25 to 1 mg/mL) in a mixture of 3% dimethyl sulfoxide, 40% PEG 400 and the rest percentage of 40% Captisol in water (w/v). The animals are weighed before dosing. The determined body weight is used to calculate the dose volume for each animal.

Dose volume (mL/kg)=1 mg/kg/formulation concentration (mg/mL)

In instances where the formulation concentrations are less than 0.5 mg/mL, the dosing volume is about 2 mL/kg.

For oral formulation, compounds of this invention are suspended (0.5 to 0.75 mg/mL) in a mixture of 5% of 10% Tween 80 in water (v/v) and 95% of 0.5% methyl cellulose in water (w/v). PO rats are typically dosed through oral gavage following the same dose volume formula as IV to achieve a dose level of 1 to 5 mg/kg. For IV dosing, blood samples are collected (using a pre-heparinized syringe) via the jugular vein catheter at 2, 5, 15, 30, 60, 120, 180, 300, 480, and 1440 minutes post dosing. For PO dosing blood samples are collected (using a pre-heparinized syringe) via the jugular vein catheter before dosing and at 5, 15, 30, 60, 120, 180, 300, 480, and 1440 minutes post dosing. About 250 uL of blood is obtained at each time point from the animal. Equal volumes of 0.9% normal saline are replaced to prevent dehydration. The whole blood samples are maintained on ice until centrifugation. Blood samples are then centrifuged at 14,000 rpm for 10 minutes at 4° C., and the upper plasma layer is then transferred into a clean vial and stored at −80° C. The resulting plasma samples are then analyzed by liquid chromatography-tandem mass spectrometry. Following the measurement of plasma samples and dosing solutions, plasma concentration-time curve is plotted. Plasma exposure is calculated as the area under the concentration-time curve extrapolated to time infinite ($AUC_{inf}$). The $AUC_{inf}$ is averaged and the oral bioavailability (% F) for individual animal is calculated as: $AUC_{inf}(PO)/AUC_{inf}(IV)$, normalized to their respective dose levels.

The % F can be reported as the mean % F of all animals dosed orally with the compound of the invention at the specified level.

The % F values of the compounds tested are set forth in Table 3, below. For the purpose of Table 3, the oral bioavailability of each compound is expressed as follows:

"+" 0-25% F
"++" 26-250% F
"+++" 51-75% F
"++++" >75% F

TABLE 3

Oral Bioavailability of Exemplary Compounds

| ID | Oral Bioavailability F (%) |
|---|---|
| 2 | + |
| 3 | ++ |
| 5 | + |
| 10 | ++++ |
| 11 | ++++ |
| 12 | ++ |
| 13 | +++ |
| 15 | +++ |
| 16 | ++++ |
| 19 | + |
| 21 | +++ |
| 22 | ++ |
| 23 | ++ |
| 25 | ++ |
| 26 | +++ |
| 28 | ++ |
| 29 | + |
| 40 | ++ |
| 41 | ++ |
| 42 | ++ |
| 44 | ++ |
| 45 | ++ |
| 47 | ++ |
| 49 | + |
| 51 | + |
| 54 | ++ |
| 56 | ++ |

Plasma Protein Binding

The plasma protein binding of compounds of invention is measured in human and rat plasma, respectively. A stock solution of the tested compound is prepared in 1 mg/mL in DMSO solution. The stock solution is spiked into the blank plasma to get a final compound concentration at 1 μg/mL for testing. Equilibrium dialysis (The equilibrium dialyzer-96TM MWCO 5K Daltons, Harvard Apparatus) method is used for the testing purpose.

The compound spiked plasma (at 1 μg/nL) and phosphate buffer (0.1 M, pH 7.4), 200 μl each, are added into the opposite sides of the membrane in a 96-well equilibrium dialyzer, respectively. The dialyzer plate is covered and incubated overnight (16 hr) at 37° C. in the 8-plate rotor incubator (Big Shot III 8-plate rotor, Harvard Apparatus). Aliquots (100 μL) are taken from the plasma and the buffer compartments, respectively. The matrix effects are eliminated by adding the same volume of blank plasma into the samples from buffer compartments and adding the same volume of phosphate buffer into the samples from plasma compartments. The samples are extracted by using the regular (3:1) protein precipitation extraction procedure (acetonitrile with internal standard). The supernatants are taken for LC/MS/MS analysis. The percentage of plasma-protein binding can be calculated by using the following method:

% Free=[Free Drug/Total Drug]*100=
   [(Peak Area)$_{buffer}$/(Peak Area)$_{plasma}$]*100

% Bound=100−% Free.

The % Plasma Protein Binding values (Bound) of the compounds tested are set forth in Table 4, below. For the purpose of Table 4, the plasma protein binding of each compound is expressed as follows:

"*" >90%

"**" 76-90%

"***" 51-75%

TABLE 4

Plasma Protein Binding of Exemplary Compounds

| ID | Human Plasma Protein Binding (%) |
| --- | --- |
| 10 | * |
| 11 | * |
| 13 | * |
| 16 | * |
| 19 | * |
| 21 | * |
| 22 | * |
| 23 | * |
| 25 | ** |
| 26 | ** |
| 28 | * |
| 40 | ** |
| 41 | * |
| 42 | * |
| 56 | *** |
| 61 | ** |
| 63 | *** |
| 64 | ** |
| 65 | *** |
| 67 | ** |
| 68 | *** |

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

What is claimed is:

1. A bicycloheteroaryl compound having a formula Ia or Ib:

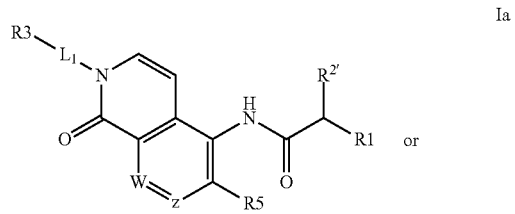

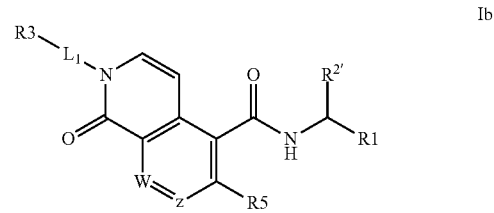

wherein

W is $CR^4$; Z is $CR^4$;

$L_1$ is a single bond, or $C_1$-$C_2$ alkylene, unsubstituted or substituted with alkyl, oxo, or hydroxyalkyl;

$R^1$ is selected from substituted or unsubstituted aryl;

$R^{2'}$ is H or Me;

$R^3$ is selected from hydroxy, amino, alkylamino, and substituted or unsubstituted heterocycloalkyl; provided that when $R^3$ is hydroxy, amino or alkylamino then $L^1$ is other than a bond;

each $R^4$ is independently selected from H, substituted or unsubstituted alkyl, substituted or unsubstituted alkoxy, cyano, substituted or unsubstituted cycloalkyl, substituted or unsubstituted cycloheteroalkyl, halo, and hydroxy;

$R^5$ is selected from substituted or unsubstituted alkyl, substituted or unsubstituted alkoxy, cyano, substituted or unsubstituted cycloalkyl, substituted or unsubstituted cycloheteroalkyl, halo, and hydroxy;

or a pharmaceutically acceptable salt thereof;

or a stereoisomer, isotopic variant or a tautomer thereof.

2. A compound according to claim 1 wherein the compound is according to formulae IIa or IIb:

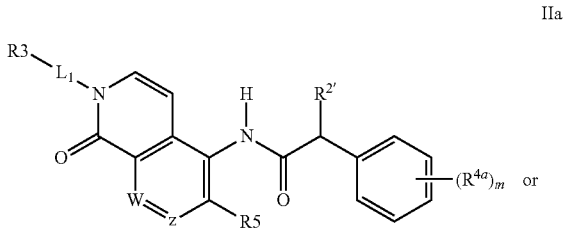

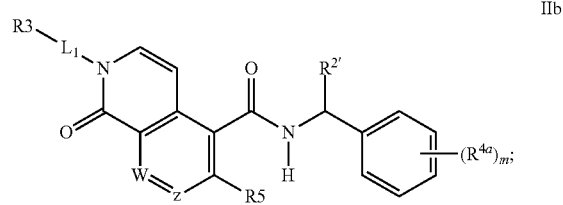

wherein

W, Z, $L_1$, $R^{2'}$, $R^3$, $R^4$ and $R^5$ are as in claim 1;

each $R^{4a}$ is independently selected from H, substituted or unsubstituted alkyl, substituted or unsubstituted acyl, substituted or unsubstituted acylamino, substituted or unsubstituted alkylamino, substituted or unsubstituted alkylhio, substituted or unsubstituted alkoxy, substituted or unsubstituted alkoxycarbonyl, substituted or unsubstituted alkylarylamino, substituted or unsubstituted arylalkyloxy, substituted or unsubstituted amino, substituted or unsubstituted aryl, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol; and m is selected from 0-5;

or a pharmaceutically acceptable salt thereof;

or a stereoisomer, isotopic variant or a tautomer thereof.

3. A compound according to claim 2 wherein m is 1 or 2.

4. A compound according to claim 3 wherein each $R^{4a}$ is independently selected from Me, Et, Ph, Cl, F, Br, CN, OH, OMe, OEt, OPh, COPh, $CF_3$, $CHF_2$, $OCF_3$, i-Pr, i-Bu, t-Bu, SMe, $CH=CH-CO_2H$, SOMe, $SO_2Me$, $SO_3H$, $SO_3Me$ and pyridyl.

5. A compound according to claim 1 wherein the group -$L_1$-$R^3$ is selected from

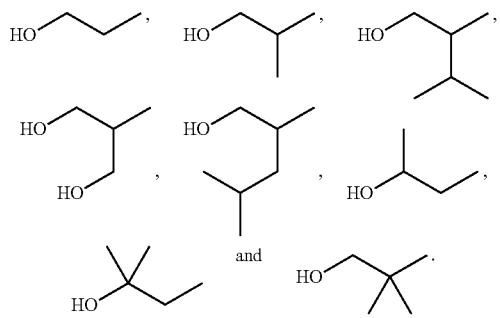

6. A compound according to claim 1 wherein the group -$L_1$-$R^3$ is selected from

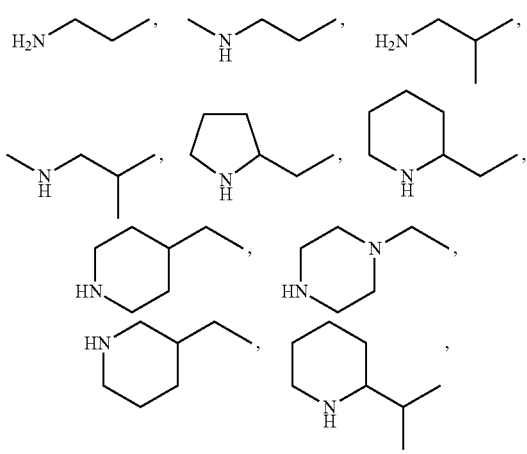

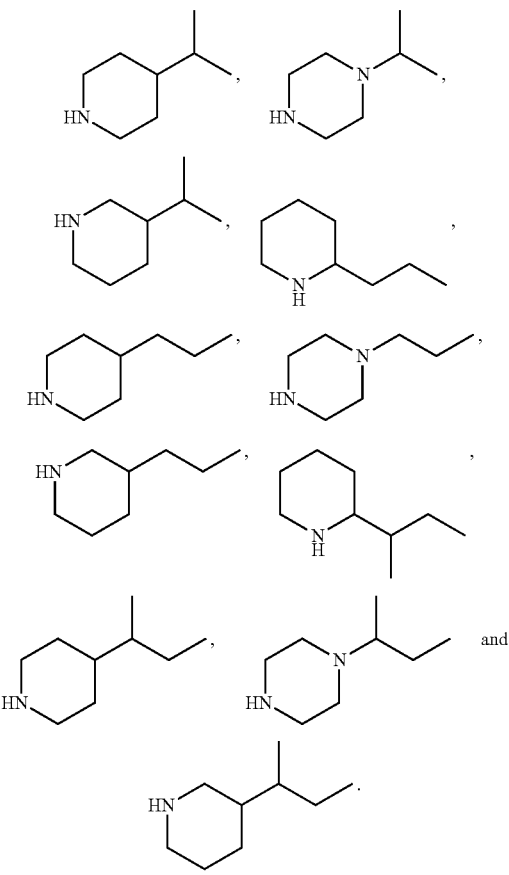

7. A compound according to claim 1 wherein the group -$L_1$-$R^3$ is selected from

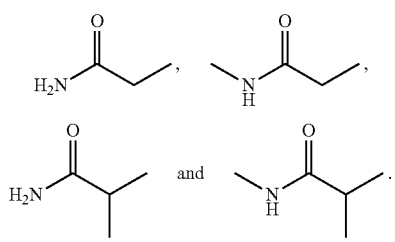

8. A compound according to claim 1 wherein the compound is according to formula IVa, IVb, IVc, IVd, IVe, IVf, IVg, or IVh:

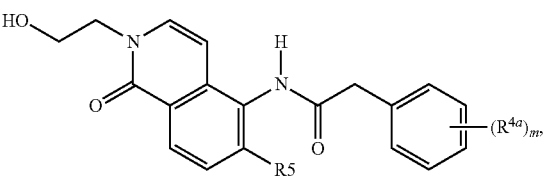

-continued

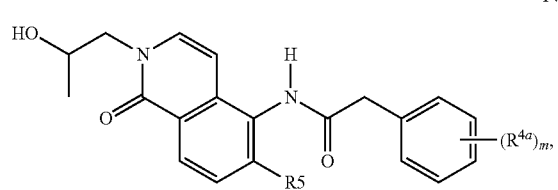
IVb

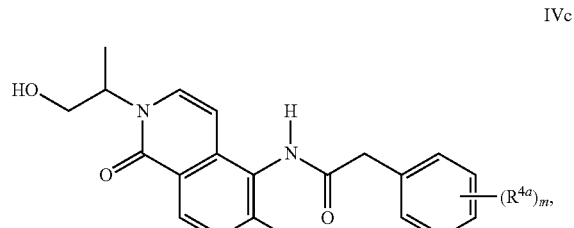
IVc

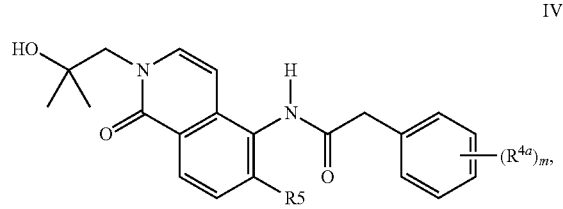
IVd

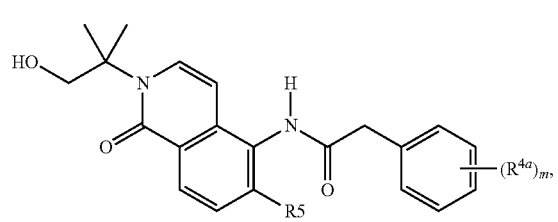
IVe

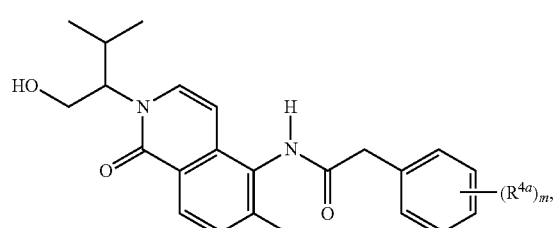
IVf

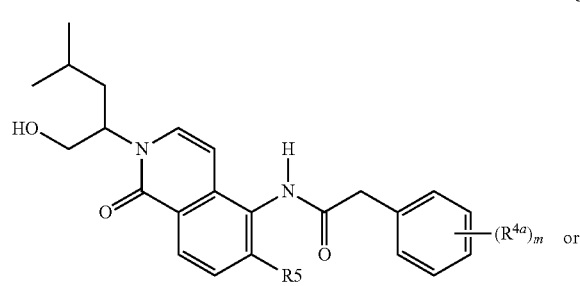
IVg or

-continued

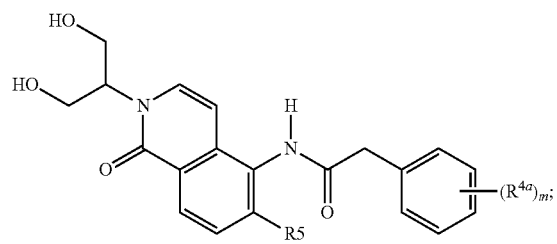
IVh wherein each $R^{4a}$ is independently selected from hydrogen, alkyl, substituted alkyl, substituted or unsubstituted alkoxy, cyano, halo, and hydroxy; and m is selected from 0-5;

and $R^5$ is selected from alkyl, cycloalkyl, or halo.

9. A compound according to claim 1 wherein the compound is according to formula Va, Vb, Vc, Vd, Ve, Vf, Vg, Vh, Vi or Vj:

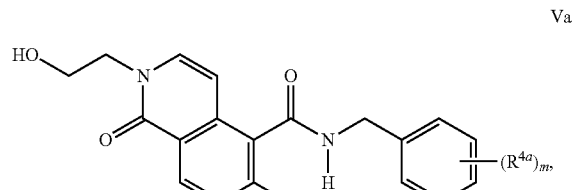
Va

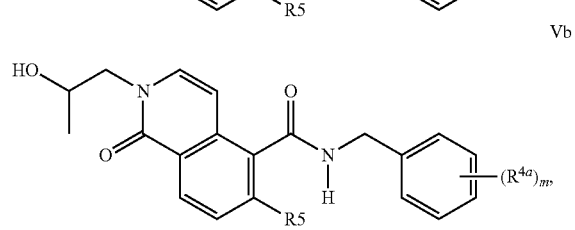
Vb

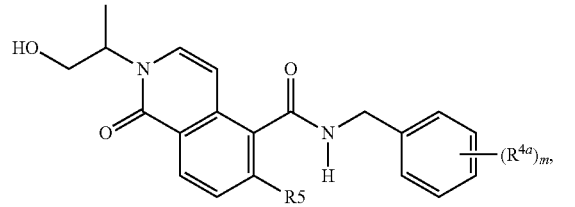
Vc

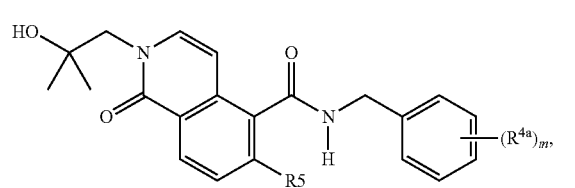
Vd

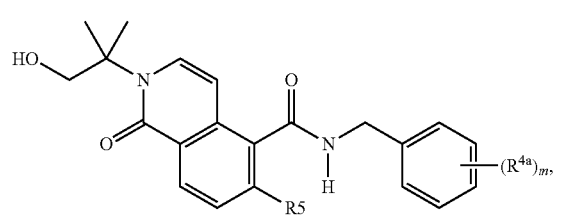
Ve

Vf

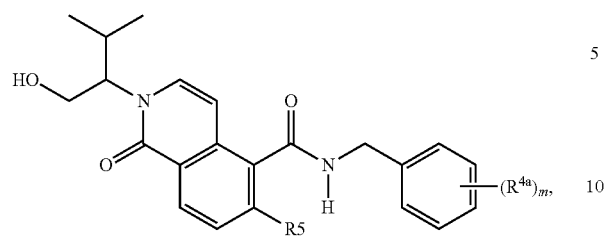

Vg

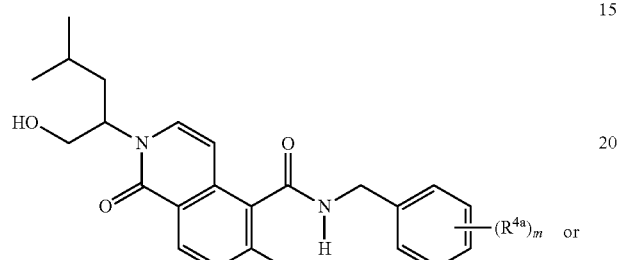    or

Vh

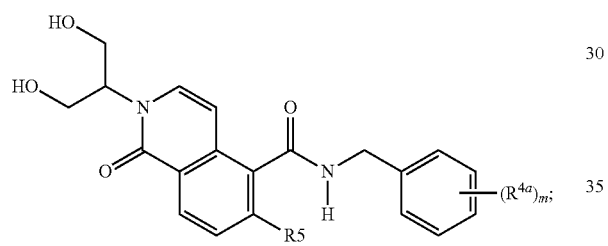;

wherein each $R^{4a}$ is independently selected from hydrogen, alkyl, substituted alkyl, substituted or unsubstituted alkoxy, cyano, halo and hydroxy; and m is selected from 0-5; and $R^5$ is selected from alkyl, cycloalkyl or halo.

10. A compound according to claim 1 wherein the compound is according to formula VIa, VIb, VIc, VId, VIe, VIf, VIg, VIh, VIi or VIj:

VIa

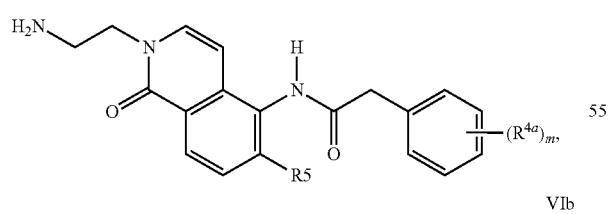

VIb

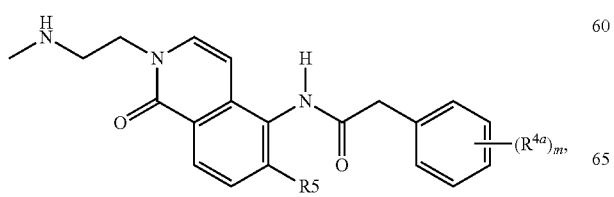

VIc

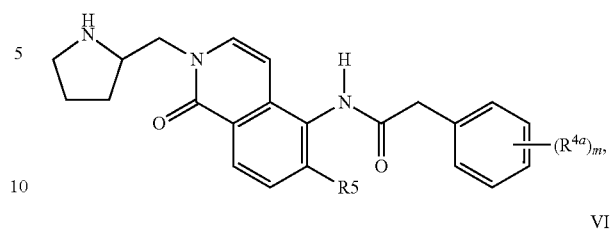

VId

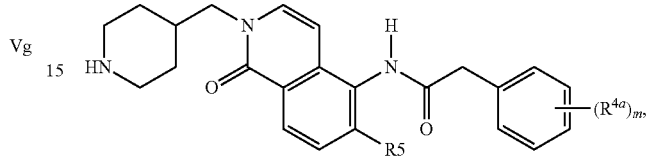

VIe

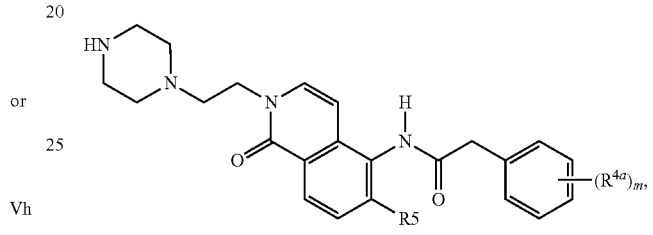

VIf

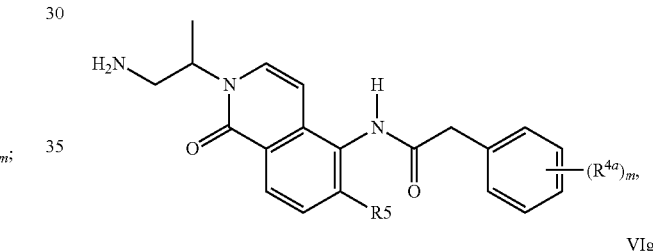

VIg

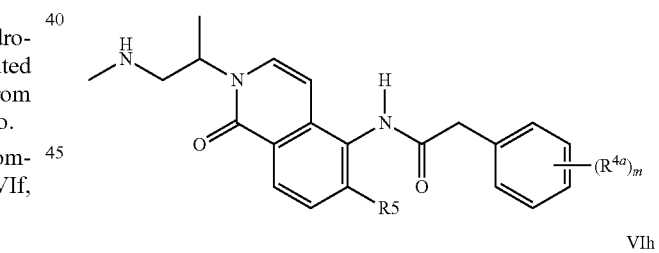

VIh

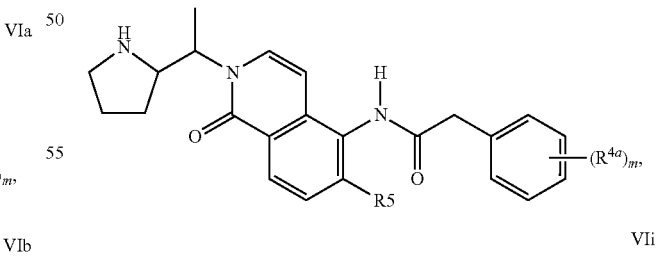

VIi

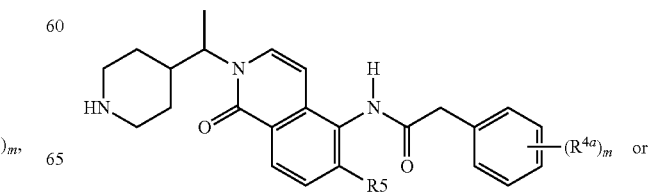    or

VIj

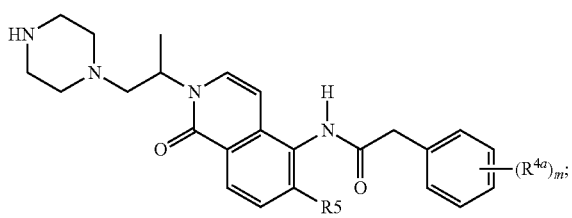

wherein each $R^{4a}$ is independently selected from hydrogen, alkyl, substituted alkyl, substituted or unsubstituted alkoxy, cyano, halo, and hydroxy; and m is selected from 0-5; and $R^5$ is selected from alkyl, cycloalkyl, or halo.

11. A compound according to claim 1 wherein the compound is according to formula VIIa, VIIb, VIIc, VIId, VIIe, VIIf, VIIg, VIIh, VIIi or VIIj:

VIIa

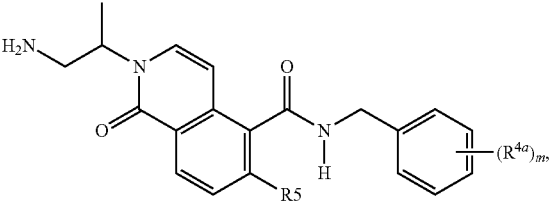

VIIb

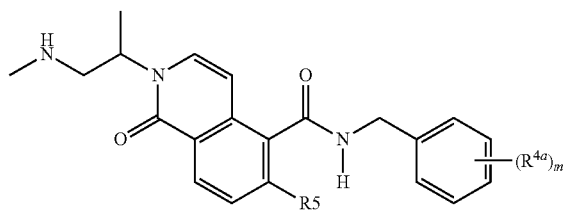

VIIc

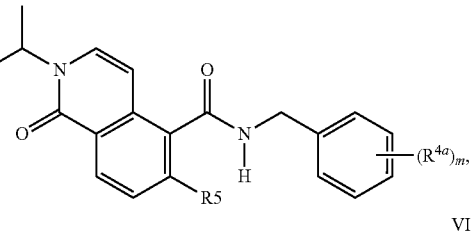

VIId

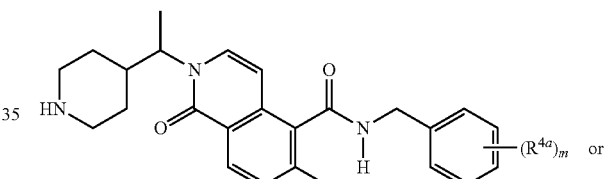

VIIe

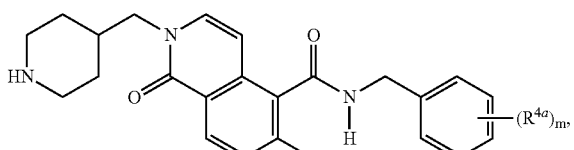

VIIf

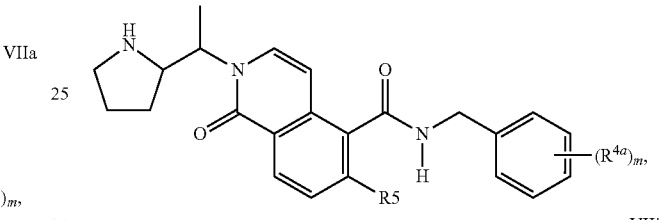

VIIg

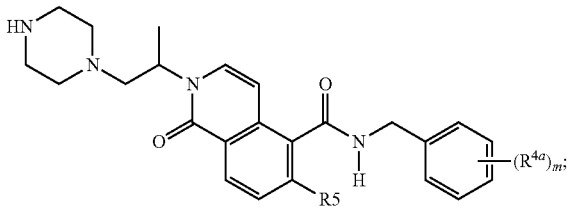

VIIh

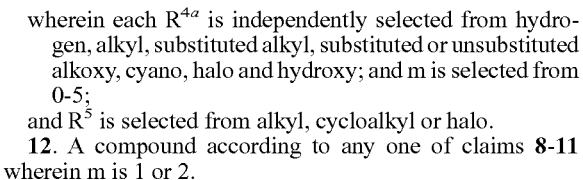

VIIi

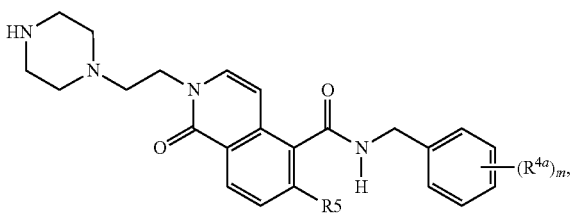

or

VIIj wherein each $R^{4a}$ is independently selected from hydrogen, alkyl, substituted alkyl, substituted or unsubstituted alkoxy, cyano, halo and hydroxy; and m is selected from 0-5;
and $R^5$ is selected from alkyl, cycloalkyl or halo.

12. A compound according to any one of claims 8-11 wherein m is 1 or 2.

13. A compound according to any one of claims 8-11 wherein each $R^{4a}$ is independently selected from H, Me, Et, Cl, F, CN, OH, OMe, OEt, $CF_3$, $CHF_2$, $OCF_3$, i-Pr, i-Bu and t-Bu.

14. A compound according to any one of claims 8-11 wherein m is 2; one $R^{4a}$ is F or Cl; and the other $R^{4a}$ is $CF_3$.

15. A compound according to any one of claims 8-11, wherein $R^5$ is Me, cyclopropyl, Cl, F or $CF_3$.

16. A compound according to claim 1 wherein the compound is selected from:
N-[6-Chloro-2-(2-hydroxy-ethyl)-1-oxo-1,2-dihydro-isoquinolin-5-yl]-2-(3,4-dichloro-phenyl)-acetamide;

(R)-2-{6-Chloro-1-oxo-5-[2-(4-trifluoromethyl-phenyl)-acetylamino]-1H-isoquinolin-2-yl}-propionamide;
(R)-2-{6-Chloro-5-[(S)-2-(4-chloro-phenyl)-propionylamino]-1-oxo-1H-isoquinolin-2-yl}-propionamide;
(R)-2-{6-Chloro-5-[2-(2-fluoro-3-trifluoromethyl-phenyl)-acetylamino]-1-oxo-1H-isoquinolin-2-yl}-propionamide;
(R)-2-{6-Chloro-5-[2-(4-chloro-2-fluoro-phenyl)-acetylamino]-1-oxo-1H-isoquinolin-2-yl}-propionamide
(R)-2-{6-Methoxy-1-oxo-5-[2-(4-trifluoromethyl-phenyl)-acetylamino]-1H-isoquinolin-2-yl}-propionamide;
(S)-2-{6-Chloro-1-oxo-5-[2-(4-trifluoromethyl-phenyl)-acetylamino]-1H-isoquinolin-2-yl}-propionamide;
2-(3-Fluoro-4-trifluoromethyl-phenyl)-N-[2-4(R)-2-hydroxy-1-methyl-ethyl)-6-methoxy-1-oxo-1,2-dihydro-isoquinolin-5-yl]-acetamide;
N-[6-Chloro-2-((R)-2-hydroxy-1-methyl-ethyl)-1-oxo-1,2-dihydro-isoquinolin-5-yl]-2-(4-trifluoromethyl-phenyl)-acetamide;
N-[6-Chloro-2-((R)-2-hydroxy-1-methyl-ethyl)-1-oxo-1,2-dihydro-isoquinolin-5-yl]-2-(3-fluoro-4-trifluoromethyl-phenyl)-acetamide;
N-[6-Chloro-2-((R)-2-hydroxy-1-methyl-ethyl)-1-oxo-1,2-dihydro-isoquinolin-5-yl]-2-(3,4-dichloro-phenyl)-acetamide;
N-[6-Chloro-2-((R)-2-hydroxy-1-methyl-ethyl)-1-oxo-1,2-dihydro-isoquinolin-5-yl]-2-(4-fluoro-3-trifluoromethyl-phenyl)-acetamide;
N-[6-Chloro-2-((R)-2-hydroxy-1-methyl-ethyl)-1-oxo-1,2-dihydro-isoquinolin-5-yl]-2-(2-fluoro-4-trifluoromethyl-phenyl)-acetamide;
2-(4-Chloro-3-fluoro-phenyl)-N-[6-chloro-2-((R)-2-hydroxy-1-methyl-ethyl)-1-oxo-1,2-dihydro-isoquinolin-5-yl]-acetamide;
N-[6-Chloro-2-(2-hydroxy-ethyl)-1-oxo-1,2-dihydro-isoquinolin-5-yl]-2-(3-fluoro-4-trifluoromethyl-phenyl)-acetamide;
N-[6-Cyclopropyl-2-4(R)-2-hydroxy-1-methyl-ethyl)-1-oxo-1,2-dihydro-isoquinolin-5-yl]-2-(3-fluoro-4-trifluoromethyl-phenyl)-acetamide;
2-(2-Fluoro-3-trifluoromethyl-phenyl)-N-[2-(2-hydroxy-ethyl)-6-(2-hydroxy-ethylamino)-1-oxo-1,2-dihydro-isoquinolin-5-yl]-acetamide;
N-[6-Chloro-2-(2-hydroxy-ethyl)-1-oxo-1,2-dihydro-isoquinolin-5-yl]-2-(4-fluoro-3-trifluoromethyl-phenyl)-acetamide;
N-[6-Chloro-2-(2-hydroxy-ethyl)-1-oxo-1,2-dihydro-isoquinolin-5-yl]-2-(2-fluoro-3-trifluoromethyl-phenyl)-acetamide;
2-(3-Fluoro-4-trifluoromethyl-phenyl)-N-[2-4(R)-2-hydroxy-1-methyl-ethyl)-6-methyl-1-oxo-1,2-dihydro-isoquinolin-5-yl]-acetamide;
2-(4-Fluoro-3-trifluoromethyl-phenyl)-N-[2-4(R)-2-hydroxy-1-methyl-ethyl)-6-methyl-1-oxo-1,2-dihydro-isoquinolin-5-yl]-acetamide;
2-(2-Fluoro-3-trifluoromethyl-phenyl)-N-[2-4(R)-2-hydroxy-1-methyl-ethyl)-6-methyl-1-oxo-1,2-dihydro-isoquinolin-5-yl]-acetamide;
2-(2-Fluoro-3-trifluoromethyl-phenyl)-N-[2-(2-hydroxy-ethyl)-6-methyl-1-oxo-1,2-dihydro-isoquinolin-5-yl]-acetamide;
N-[2-((R)-2-Hydroxy-1-methyl-ethyl)-6-methyl-1-oxo-1,2-dihydro-isoquinolin-5-yl]-2-(4-trifluoromethyl-phenyl)-acetamide;
2-(4-Chloro-3-fluoro-phenyl)-N-[2-((R)-2-hydroxy-1-methyl-ethyl)-6-methyl-1-oxo-1,2-dihydro-isoquinolin-5-yl]-acetamide;
2-(4-Fluoro-3-trifluoromethyl-phenyl)-N-[2-(2-hydroxy-ethyl)-6-methyl-1-oxo-1,2-dihydro-isoquinolin-5-yl]-acetamide;
2-(3-Fluoro-4-trifluoromethyl-phenyl)-N-[2-(2-hydroxy-ethyl)-6-methyl-1-oxo-1,2-dihydro-isoquinolin-5-yl]-acetamide;
2-(3-Fluoro-4-trifluoromethyl-phenyl)-N-((S)-6-methyl-1-oxo-2-pyrrolidin-3-yl-1,2-dihydro-isoquinolin-5-yl)-acetamide; and
2-(4-Fluoro-3-trifluoromethyl-phenyl)-N-((S)-6-methyl-1-oxo-2-pyrrolidin-3-yl-1,2-dihydro-isoquinolin-5-yl)-acetamide; or a pharmaceutically acceptable salt thereof;
or a stereoisomer, isotopic variant or a tautomer thereof.

17. A compound according to claim 1 wherein the compound is selected from:
2-(3-Fluoro-4-trifluoromethyl-phenyl)-N-[2-4(S)-2-hydroxy-1-methyl-ethyl)-6-methyl-1-oxo-1,2-dihydro-isoquinolin-5-yl]-acetamide;
N-[6-Chloro-2-((S)-2-hydroxy-1-methyl-ethyl)-1-oxo-1,2-dihydro-isoquinolin-5-yl]-2-(3-fluoro-4-trifluoromethyl-phenyl)-acetamide;
N-[2-((R)-2-Hydroxy-1-methyl-ethyl)-6-methyl-1-oxo-1,2-dihydro-isoquinolin-5-yl]-2-(3-trifluoromethyl-phenyl)-acetamide;
2-(3-Fluoro-4-trifluoromethyl-phenyl)-N-[6-methyl-2-(2-methylamino-ethyl)-1-oxo-1,2-dihydro-isoquinolin-5-yl]-acetamide;
N-[6-Chloro-2-((R)-2-hydroxy-1-methyl-ethyl)-1-oxo-1,2-dihydro-isoquinolin-5-yl]-2-(3-trifluoromethyl-phenyl)-acetamide;
2-((R)-2-Hydroxy-1-methyl-ethyl)-6-methyl-1-oxo-1,2-dihydro-isoquinoline-5-carboxylic acid 3-fluoro-4-trifluoromethyl-benzylamide;
6-Chloro-2-((R)-2-hydroxy-1-methyl-ethyl)-1-oxo-1,2-dihydro-isoquinoline-5-carboxylic acid 3-fluoro-4-trifluoromethyl-benzylamide;
2-((R)-2-Hydroxy-1-methyl-ethyl)-6-methyl-1-oxo-1,2-dihydro-isoquinoline-5-carboxylic acid 3-trifluoromethyl-benzylamide;
6-Chloro-2-((R)-2-hydroxy-1-methyl-ethyl)-1-oxo-1,2-dihydro-isoquinoline-5-carboxylic acid 3-trifluoromethyl-benzylamide;
6-Chloro-2-((R)-2-hydroxy-1-methyl-ethyl)-1-oxo-1,2-dihydro-isoquinoline-5-carboxylic acid 4-chloro-3-fluoro-benzylamide;
6-Chloro-2-((R)-2-hydroxy-1-methyl-ethyl)-1-oxo-1,2-dihydro-isoquinoline-5-carboxylic acid 2-trifluoromethyl-benzylamide;
2-((R)-2-Hydroxy-1-methyl-ethyl)-6-methyl-1-oxo-1,2-dihydro-isoquinoline-5-carboxylic acid 4-chloro-3-fluoro-benzylamide;
(R)-2-{5-[2-(3-Fluoro-4-trifluoromethyl-phenyl)-acetylamino]-6-methyl-1-oxo-1H-isoquinolin-2-yl}-propionamide;
N-[2-((R)-2-Amino-1-methyl-ethyl)-6-methyl-1-oxo-1,2-dihydro-isoquinolin-5-yl]-2-(3-fluoro-4-trifluoromethyl-phenyl)-acetamide;
2-(3-Fluoro-4-trifluoromethyl-phenyl)-N-[6-methyl-2-((R)-1-methyl-2-methylamino-ethyl)-1-oxo-1,2-dihydro-isoquinolin-5-yl]-acetamide;
2-(3-Fluoro-4-trifluoromethyl-phenyl)-N-[6-methyl-2-((R)-1-methyl-2-piperazin-1-yl-ethyl)-1-oxo-1,2-dihydro-isoquinolin-5-yl]-acetamide;

2-(3-Fluoro-4-trifluoromethyl-phenyl)-N-[2-(2-hydroxy-1-hydroxymethyl-ethyl)-6-methyl-1-oxo-1,2-dihydro-isoquinolin-5-yl]-acetamide;

2-(3-Fluoro-4-trifluoromethyl-phenyl)-N-{2-[(R)-2-(3-hydroxy-azetidin-1-yl)-1-methyl-ethyl]-6-methyl-1-oxo-1,2-dihydro-isoquinolin-5-yl}-acetamide; or a pharmaceutically acceptable salt thereof;

or a stereoisomer, isotopic variant or a tautomer thereof.

18. A compound according to claim 12 wherein each $R^{4a}$ is independently selected from H, Me, Et, Cl, F, CN, OH, OMe, OEt, $CF_3$, $CHF_2$, $OCF_3$, i-Pr, i-Bu and t-Bu.

19. A compound according to claim 1 wherein the compound is selected from:

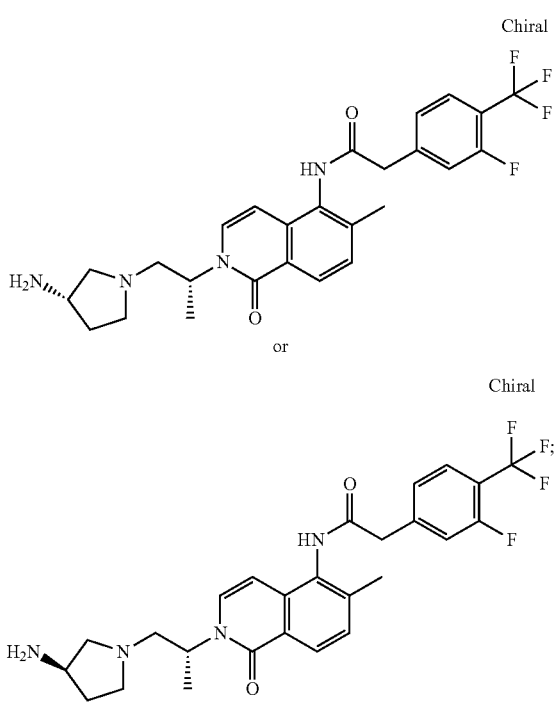

or a pharmaceutically acceptable salt thereof.

20. A pharmaceutical composition comprising a pharmaceutically acceptable carrier and a pharmaceutically effective amount of a compound of claim 1.

21. The pharmaceutical composition of claim 20, wherein the carrier is a parenteral, oral or topical carrier.

22. A method for treating in a mammal a disease or condition that is causally related to the aberrant activity of the $P2X_7$ receptor in vivo, which comprises administering to the mammal an effective disease-treating or condition-treating amount of a compound according to claim 1, or a pharmaceutical composition according to claim 20, wherein the disease or condition is selected from a pain condition, and an inflammatory disease or condition.

23. A method for treating in a mammal a disease or condition selected from: pain including acute, inflammatory and neuropathic pain, chronic pain, dental pain and headache including migraine, cluster headache and tension headache; and diseases and disorders which are mediated by or result in inflammation, arthritis, rheumatoid arthritis and osteoarthritis, diseases and disorders which are mediated by or result in neuroinflammation, and inflammatory bowel disease, which comprises administering to the mammal an effective disease-treating or condition-treating amount of a compound according to claim 1, or a pharmaceutical composition of claim 20.

24. The method of claim 23, wherein the disease or condition is rheumatoid arthritis.

25. The method of claim 23, wherein the disease or condition is osteoarthritis.

26. The method of claim 23, wherein the disease or condition is pain.

27. The method of claim 23, wherein the disease or condition is neuropathic pain.

28. The method of claim 27, wherein the pain is associated with a condition selected from the group consisting of post-mastectomy pain syndrome, stump pain, phantom limb pain, oral neuropathic pain, Charcot's pain, toothache, venomous snake bite, spider bite, insect sting, postherpetic neuralgia, diabetic neuropathy, reflex sympathetic dystrophy, trigeminal neuralgia, osteoarthritis, rheumatoid arthritis, fibromyalgis, Guillain-Barre syndrome, meralgia paresthetica, burning-mouth syndrome, bilateral peripheral neuropathy, causalgia, sciatic neuritis, peripheral neuritis, polyneuritis, segmental neuritis, Gombault's neuritis, neuronitis, cervicobrachial neuralgia, cranial neuralgia, egniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia splenopalatine neuralgia, supraorbital neuralgia, vidian neuralgia, sinus headache, tension headache, labor, childbirth, intestinal gas, menstruation, cancer, and trauma.

* * * * *